(12) United States Patent
Rouse et al.

(10) Patent No.: US 11,412,983 B2
(45) Date of Patent: Aug. 16, 2022

(54) COMPUTERIZED ORAL PRESCRIPTION ADMINISTRATION WITH REFILLABLE MEDICATION DISPENSING DEVICES AND ASSOCIATED SYSTEMS AND METHODS

(71) Applicant: Berkshire Biomedical, LLC, Dallas, TX (US)

(72) Inventors: Thomas M. Rouse, Dallas, TX (US); Susan B. Owen, Dallas, TX (US); Christy Corey, Fishers, IN (US); Carlton Chow, Dallas, TX (US); Michael Turi, Dallas, TX (US); Larry Bischoff, Dallas, TX (US); Steven Hartman, Dallas, TX (US); Robert Boyer, Dallas, TX (US); Richard Cronenberg, Dallas, TX (US); Michael Quinn, Dallas, TX (US); James Lynch, Dallas, TX (US)

(73) Assignee: BERKSHIRE BIOMEDICAL CORPORATION, Dallas, TX (US)

( * ) Notice: Subject to any disclaimer, the term of this patent is extended or adjusted under 35 U.S.C. 154(b) by 154 days.

(21) Appl. No.: 16/597,730

(22) Filed: Oct. 9, 2019

(65) Prior Publication Data
US 2020/0038295 A1    Feb. 6, 2020

Related U.S. Application Data

(62) Division of application No. 15/958,809, filed on Apr. 20, 2018, now Pat. No. 10,441,509.
(Continued)

(51) Int. Cl.
*A61J 7/00*    (2006.01)
*A61B 5/00*    (2006.01)
(Continued)

(52) U.S. Cl.
CPC ............ *A61B 5/682* (2013.01); *A61J 7/0053* (2013.01); *G16H 20/13* (2018.01); *A61B 2562/0214* (2013.01); *A61J 17/02* (2013.01)

(58) Field of Classification Search
CPC .......... A61B 2562/0214; A61B 5/1178; A61B 5/682; A61C 19/063; A61C 7/08;
(Continued)

(56) References Cited

U.S. PATENT DOCUMENTS 3,840,992 A * 10/1974 English ............. A61C 17/0211
                                                  604/77
4,116,195 A    9/1978 James
(Continued)

FOREIGN PATENT DOCUMENTS

CN         1997421        7/2007
CN       203417402        2/2014
(Continued)

OTHER PUBLICATIONS

International Search Report issued in PCT/US2018/013440 dated Mar. 9, 2018.
(Continued)

*Primary Examiner* — Quynh-Nhu H. Vu
(74) *Attorney, Agent, or Firm* — Haynes and Boone, LLP

(57) ABSTRACT

Computerized oral prescription administration with refillable medication dispensing devices and associated systems and methods are provided. In one embodiment, a method of dispensing a substance to an intended user is provided. The method comprises receiving an input from a biometric sensor; determining, based on the received input, whether an intended user's unique biometric attribute is detected by the biometric sensor; receiving an input from an environmental sensor; determining, based on the received input, whether a mouthpiece is positioned within a user's mouth; receiving an
(Continued)

input from a capacitive sensor array of the mouthpiece; determining, based on the received input, whether an intended user's unique dentition is positioned within a recess of the mouthpiece; and dispensing a substance from a reservoir to a mouth of the intended user in response to determining that the intended user's unique biometric attribute is detected by the biometric sensor.

25 Claims, 26 Drawing Sheets

Related U.S. Application Data

(60) Provisional application No. 62/644,145, filed on Mar. 16, 2018.

(51) Int. Cl.
 *G16H 20/13* (2018.01)
 *A61J 17/02* (2006.01)

(58) Field of Classification Search
 CPC ........... A61C 7/14; A61C 7/146; A61C 15/00; A61C 15/043; A61C 17/00; A61C 17/02; A61C 17/0202; A61C 17/0205; G06K 9/00885; G16H 20/13; G16H 20/17; G16H 40/63
 See application file for complete search history.

(56) References Cited

U.S. PATENT DOCUMENTS

| | | | |
|---|---|---|---|
| 4,237,884 A | 12/1980 | Erickson et al. | |
| 4,353,365 A | 10/1982 | Hallworth et al. | |
| 4,428,502 A | 1/1984 | Veltri | |
| 4,474,308 A | 10/1984 | Bergeron | |
| 4,717,042 A | 1/1988 | McLaughlin | |
| 4,784,288 A | 11/1988 | Jennings | |
| 5,040,223 A * | 8/1991 | Kamiya | G07C 9/257 |
| | | | 382/227 |
| 5,159,581 A | 10/1992 | Agans | |
| 5,583,831 A | 12/1996 | Churchill et al. | |
| 5,791,515 A | 8/1998 | Khan et al. | |
| 5,852,590 A | 12/1998 | de la Huerga | |
| H0001782 H | 2/1999 | Wicks et al. | |
| 5,881,721 A | 3/1999 | Bunce et al. | |
| 5,947,329 A | 9/1999 | Bailey | |
| 5,954,697 A * | 9/1999 | Srisathapat | A61M 5/1456 |
| | | | 604/154 |
| 5,960,085 A | 9/1999 | de la Huerga | |
| 5,971,594 A | 10/1999 | Sahai et al. | |
| 5,990,782 A | 11/1999 | Lee | |
| 6,018,289 A | 1/2000 | Sekura et al. | |
| 6,032,155 A | 2/2000 | de la Huerga | |
| 6,082,363 A | 7/2000 | Washburn | |
| 6,089,864 A | 7/2000 | Buckner et al. | |
| 6,112,942 A | 9/2000 | Deacon | |
| 6,119,684 A | 9/2000 | Nohl et al. | |
| 6,145,697 A | 11/2000 | Gudish | |
| 6,163,736 A | 12/2000 | Halfacre | |
| 6,198,383 B1 | 3/2001 | Sekura et al. | |
| 6,259,654 B1 | 7/2001 | de la Huerga | |
| 6,304,797 B1 | 10/2001 | Shusterman | |
| 6,332,100 B1 | 12/2001 | Sahai et al. | |
| 6,335,907 B1 | 1/2002 | Momich et al. | |
| 6,408,330 B1 | 6/2002 | DeLaHuerga | |
| 6,431,399 B2 | 8/2002 | Gabel et al. | |
| 6,529,446 B1 | 3/2003 | de la Huerga | |
| 6,604,650 B2 | 8/2003 | Sagar | |
| 6,611,733 B1 | 8/2003 | De La Huerga | |
| 6,702,146 B2 | 3/2004 | Varis | |
| 6,779,024 B2 | 8/2004 | DeLaHuerga | |
| 6,834,775 B1 | 12/2004 | Collins | |
| 6,958,691 B1 | 10/2005 | Anderson et al. | |
| 6,988,634 B2 | 1/2006 | Varis | |
| 7,006,894 B2 | 2/2006 | de la Huerga | |
| 7,042,807 B1 | 5/2006 | Breen | |
| 7,048,141 B2 | 5/2006 | Abdulhay et al. | |
| 7,061,831 B2 | 6/2006 | De La Huerga | |
| 7,072,738 B2 | 7/2006 | Bonney et al. | |
| 7,073,685 B1 | 7/2006 | Giraud et al. | |
| 7,100,797 B2 | 9/2006 | Kahn et al. | |
| 7,104,417 B2 | 9/2006 | Hilliard | |
| 7,128,240 B1 | 10/2006 | Oesch | |
| 7,147,127 B2 | 12/2006 | Lepke et al. | |
| 7,178,688 B2 | 2/2007 | Naufel et al. | |
| 7,182,955 B2 | 2/2007 | Hart et al. | |
| 7,213,721 B2 | 5/2007 | Abdulhay et al. | |
| 7,216,802 B1 | 5/2007 | De La Huerga | |
| 7,269,476 B2 | 9/2007 | Ratnakar | |
| 7,295,890 B2 | 11/2007 | Jean-Pierre | |
| 7,302,311 B2 | 11/2007 | Varis | |
| 7,328,859 B2 * | 2/2008 | Hornsby | B05B 1/3436 |
| | | | 222/481.5 |
| 7,359,765 B2 | 4/2008 | Varvarelis et al. | |
| 7,366,675 B1 | 4/2008 | Walker et al. | |
| 7,392,918 B2 | 7/2008 | Holloway et al. | |
| 7,404,500 B2 | 7/2008 | Marteau et al. | |
| 7,648,093 B2 | 1/2010 | Kruger | |
| 7,711,449 B2 | 5/2010 | Abdulhay et al. | |
| 7,715,277 B2 | 5/2010 | de la Huerga | |
| 7,719,927 B1 | 5/2010 | Robinson et al. | |
| 7,801,745 B2 | 9/2010 | Walker et al. | |
| 7,810,673 B2 | 10/2010 | Lancesseur et al. | |
| 7,831,336 B2 | 11/2010 | Gumpert | |
| 7,844,361 B2 | 11/2010 | Jean-Pierre | |
| 7,885,725 B2 | 2/2011 | Dunn | |
| 7,941,534 B2 | 5/2011 | de la Huerga | |
| 7,978,564 B2 | 7/2011 | De La Huerga | |
| 7,988,016 B2 | 8/2011 | Klein et al. | |
| 7,996,106 B2 | 8/2011 | Ervin | |
| 8,019,471 B2 | 9/2011 | Bogash et al. | |
| 8,028,856 B2 | 10/2011 | Erdelyi et al. | |
| 8,029,538 B2 | 10/2011 | Burroughs et al. | |
| 8,033,422 B2 | 10/2011 | Estrada | |
| 8,055,509 B1 | 11/2011 | Walker et al. | |
| 8,062,248 B2 | 11/2011 | Kindel | |
| 8,069,056 B2 | 11/2011 | Walker et al. | |
| 8,135,497 B2 | 3/2012 | Joslyn | |
| 8,195,330 B2 | 6/2012 | Coe | |
| 8,212,677 B2 | 7/2012 | Ferguson | |
| 8,226,978 B2 | 7/2012 | Palmer et al. | |
| 8,269,613 B2 | 9/2012 | Lazar | |
| 8,279,076 B2 | 10/2012 | Johnson | |
| 8,284,068 B2 | 10/2012 | Johnson | |
| 8,295,506 B2 * | 10/2012 | Kassayan | H04R 25/606 |
| | | | 381/326 |
| 8,319,613 B2 | 11/2012 | Lazar | |
| 8,326,455 B2 | 12/2012 | Dunn | |
| 8,357,114 B2 | 1/2013 | Poutiatine et al. | |
| 8,391,104 B2 | 3/2013 | de la Huerga | |
| 8,392,020 B2 | 3/2013 | Terzini | |
| 8,417,378 B2 | 4/2013 | Joslyn | |
| 8,454,557 B1 * | 6/2013 | Qi | A61M 5/14244 |
| | | | 604/67 |
| 8,483,872 B2 | 7/2013 | Ratnakar | |
| 8,499,966 B2 | 8/2013 | Palmer et al. | |
| 8,502,671 B2 | 8/2013 | Marcovici | |
| 8,502,692 B2 | 8/2013 | Johnson | |
| 8,511,478 B2 | 8/2013 | Terzini | |
| 8,548,623 B2 | 10/2013 | Poutiatine et al. | |
| 8,552,868 B1 | 10/2013 | Ferguson | |
| 8,574,189 B2 | 11/2013 | Poutiatine et al. | |
| 8,600,548 B2 | 12/2013 | Bossi et al. | |
| 8,636,172 B2 | 1/2014 | Dunn | |
| 8,666,539 B2 | 3/2014 | Ervin | |
| 8,666,543 B2 | 3/2014 | MacVittie et al. | |
| 8,669,863 B2 | 3/2014 | Alhuwaishel | |
| 8,670,865 B2 | 3/2014 | Coe | |
| 8,725,291 B2 | 5/2014 | Czaja et al. | |
| 8,727,180 B2 | 5/2014 | Zonana et al. | |
| 8,734,061 B2 | 5/2014 | Terzini | |

(56) References Cited

U.S. PATENT DOCUMENTS

| | | |
|---|---|---|
| 8,753,308 B2 | 6/2014 | Palmer et al. |
| 8,778,393 B2 | 7/2014 | Palmer et al. |
| 8,807,131 B1 | 8/2014 | Tunnell et al. |
| 8,821,454 B2 | 9/2014 | Kriesel et al. |
| 8,854,225 B2 | 10/2014 | Johnson |
| 8,874,260 B2 | 10/2014 | Saltsov |
| 8,905,964 B2 | 12/2014 | Poutiatine et al. |
| 8,922,367 B2 | 12/2014 | Denny et al. |
| 8,973,338 B2 | 3/2015 | Terzini |
| 8,976,036 B2 | 3/2015 | Johnson |
| 8,985,388 B2 | 3/2015 | Ratnakar |
| 9,010,584 B2 | 4/2015 | Law et al. |
| 9,014,847 B2 | 4/2015 | Dunn |
| 9,019,097 B2 | 4/2015 | Choi et al. |
| 9,037,291 B2 | 5/2015 | Terzini |
| 9,043,015 B2 | 5/2015 | Ratnakar |
| 9,066,847 B2 | 6/2015 | Poutiatine et al. |
| 9,066,849 B2 | 6/2015 | Fung et al. |
| 9,155,682 B2 | 10/2015 | Boyd |
| 9,161,885 B1 | 10/2015 | Zhou |
| 9,211,559 B2 | 12/2015 | Law et al. |
| 9,218,458 B2 | 12/2015 | Baarman et al. |
| 9,235,689 B2 | 1/2016 | Ervin |
| 9,283,363 B1 | 3/2016 | Scorzelli et al. |
| 9,289,583 B2 | 3/2016 | Palmer et al. |
| 9,346,068 B2 | 5/2016 | Knight et al. |
| 9,361,772 B2 | 6/2016 | Johnson |
| 9,381,139 B2 | 7/2016 | Fung et al. |
| 9,414,899 B2 * | 8/2016 | Altounian ............ A61J 7/0015 |
| 9,418,207 B1 | 8/2016 | Patton et al. |
| 9,436,298 B2 | 9/2016 | Draper et al. |
| 9,439,835 B2 * | 9/2016 | DiMartino ............ A61J 7/0481 |
| 9,566,402 B2 | 2/2017 | Djupesland |
| 9,636,195 B2 | 5/2017 | Wolpo |
| 9,731,103 B1 | 8/2017 | Rouse et al. |
| 9,795,296 B2 | 10/2017 | Imran |
| 9,839,500 B2 * | 12/2017 | Flyash ................. A61C 17/20 |
| 9,968,777 B1 | 5/2018 | Demarest et al. |
| 2001/0009398 A1 | 7/2001 | Sekura et al. |
| 2001/0022758 A1 | 9/2001 | Howard |
| 2003/0174554 A1 | 9/2003 | Dunstone et al. |
| 2004/0008123 A1 | 1/2004 | Carrender et al. |
| 2004/0117062 A1 | 6/2004 | Bonney et al. |
| 2004/0158194 A1 | 8/2004 | Wolff et al. |
| 2004/0158349 A1 | 8/2004 | Bonney et al. |
| 2005/0230409 A1 | 10/2005 | von Schuckmann |
| 2006/0138162 A1 | 6/2006 | Anderson et al. |
| 2006/0166157 A1 * | 7/2006 | Rahman ............ A61B 5/4833 |
| | | 433/6 |
| 2006/0184271 A1 | 8/2006 | Loveless |
| 2006/0213921 A1 | 9/2006 | Abdulhay et al. |
| 2006/0218015 A1 | 9/2006 | Walker et al. |
| 2006/0282010 A1 | 12/2006 | Martin |
| 2007/0075842 A1 | 4/2007 | Russell et al. |
| 2007/0093932 A1 | 4/2007 | Abdulhay et al. |
| 2007/0095851 A1 | 5/2007 | Anderson et al. |
| 2007/0135790 A1 | 6/2007 | Auerbach |
| 2007/0138195 A1 | 6/2007 | Anderson et al. |
| 2007/0145065 A1 | 6/2007 | Anderson et al. |
| 2007/0170199 A1 | 7/2007 | York |
| 2007/0228065 A1 | 10/2007 | Anderson et al. |
| 2007/0261985 A1 | 11/2007 | Allen |
| 2007/0271001 A1 | 11/2007 | Ratnakar |
| 2008/0017658 A1 | 1/2008 | Wright |
| 2008/0027291 A1 | 1/2008 | Williams-Hartman |
| 2008/0027579 A1 | 1/2008 | van der Hoop |
| 2008/0054008 A1 | 3/2008 | Wright |
| 2008/0059228 A1 | 3/2008 | Bossi et al. |
| 2008/0140250 A1 | 6/2008 | Dave |
| 2008/0251530 A1 | 10/2008 | Holloway et al. |
| 2008/0283542 A1 | 11/2008 | Lanka et al. |
| 2009/0127157 A1 | 5/2009 | Costa et al. |
| 2009/0208898 A1 * | 8/2009 | Kaplan ................. A46B 9/045 |
| | | 433/80 |
| 2009/0210032 A1 | 8/2009 | Beiski et al. |
| 2009/0223994 A1 | 9/2009 | Getz |
| 2009/0277461 A1 | 11/2009 | Gallagher, Jr. |
| 2009/0277921 A1 | 11/2009 | Angelucci et al. |
| 2010/0006589 A1 | 1/2010 | Klein |
| 2010/0096399 A1 | 4/2010 | Ratnakar |
| 2010/0100237 A1 | 4/2010 | Ratnakar |
| 2010/0110725 A1 | 5/2010 | Chang |
| 2010/0174229 A1 | 7/2010 | Hsu et al. |
| 2010/0185456 A1 | 7/2010 | Kansal |
| 2010/0318218 A1 | 12/2010 | Muncy, Jr. et al. |
| 2010/0332023 A1 | 12/2010 | Tripathi et al. |
| 2011/0011883 A1 | 1/2011 | Nakkouri |
| 2011/0021983 A1 * | 1/2011 | Jurson ................. A61M 5/172 |
| | | 604/93.01 |
| 2011/0027746 A1 | 2/2011 | McDonough |
| 2011/0060455 A1 | 3/2011 | Bogash et al. |
| 2011/0060457 A1 | 3/2011 | De Vrught et al. |
| 2011/0142554 A1 | 6/2011 | Terzini |
| 2011/0146835 A1 | 6/2011 | Terzini |
| 2011/0152757 A1 * | 6/2011 | Beck ................. A61M 5/1452 |
| | | 604/67 |
| 2011/0160901 A1 | 6/2011 | Abrams, Jr. et al. |
| 2011/0202174 A1 | 8/2011 | Bogash et al. |
| 2011/0259910 A1 | 10/2011 | Knudsen |
| 2011/0295416 A1 | 12/2011 | Aquilonius et al. |
| 2011/0307592 A1 | 12/2011 | de la Huerga |
| 2012/0055948 A1 | 3/2012 | Leifeld et al. |
| 2012/0160716 A1 | 6/2012 | Chan et al. |
| 2012/0165975 A1 | 6/2012 | Yi et al. |
| 2012/0172679 A1 * | 7/2012 | Logan .................. A61B 5/01 |
| | | 600/301 |
| 2012/0289905 A1 | 11/2012 | Julian |
| 2013/0025607 A1 | 1/2013 | Altounian |
| 2013/0088328 A1 | 4/2013 | DiMartino et al. |
| 2013/0116818 A1 | 5/2013 | Hamilton |
| 2013/0120115 A1 | 5/2013 | Valls Chaparro et al. |
| 2013/0165828 A1 | 6/2013 | Sullivan |
| 2013/0168405 A1 | 7/2013 | Yuyama et al. |
| 2013/0211270 A1 * | 8/2013 | St. Laurent ........ A61B 5/4875 |
| | | 600/595 |
| 2013/0236851 A1 * | 9/2013 | McDonough ........ A61C 17/028 |
| | | 433/89 |
| 2013/0253286 A1 | 9/2013 | Fridman |
| 2013/0256331 A1 | 10/2013 | Giraud et al. |
| 2013/0280671 A1 | 10/2013 | Brawn et al. |
| 2013/0304255 A1 | 11/2013 | Ratnakar |
| 2013/0345859 A1 | 12/2013 | Omura et al. |
| 2014/0031975 A1 | 1/2014 | Poutiatine et al. |
| 2014/0046676 A1 | 2/2014 | Kibler et al. |
| 2014/0072932 A1 | 3/2014 | Brawn |
| 2014/0074283 A1 | 3/2014 | Blackbum |
| 2014/0114472 A1 | 4/2014 | Bossi et al. |
| 2014/0195043 A1 | 7/2014 | Ervin |
| 2014/0203021 A1 | 7/2014 | Zill |
| 2014/0207278 A1 | 7/2014 | Czaja et al. |
| 2014/0257051 A1 | 9/2014 | Cam |
| 2014/0263423 A1 | 9/2014 | Akdogan et al. |
| 2014/0263425 A1 | 9/2014 | Akdogan et al. |
| 2014/0267719 A1 | 9/2014 | Akdogan et al. |
| 2014/0277705 A1 | 9/2014 | Czaja et al. |
| 2014/0277707 A1 | 9/2014 | Akdogan et al. |
| 2014/0277710 A1 | 9/2014 | Akdogan et al. |
| 2014/0278508 A1 | 9/2014 | Akdogan et al. |
| 2014/0278510 A1 | 9/2014 | McLean et al. |
| 2014/0303989 A1 | 10/2014 | Ferguson |
| 2014/0305963 A1 | 10/2014 | Zonana et al. |
| 2014/0316799 A1 | 10/2014 | Cosgrove et al. |
| 2014/0324216 A1 | 10/2014 | Beg et al. |
| 2014/0326744 A1 | 11/2014 | Ratnakar |
| 2014/0339248 A1 | 11/2014 | Reddy et al. |
| 2014/0339249 A1 | 11/2014 | Reddy et al. |
| 2014/0346184 A1 | 11/2014 | Bae et al. |
| 2014/0346186 A1 | 11/2014 | Reddy et al. |
| 2014/0350720 A1 | 11/2014 | Lehmann et al. |
| 2014/0371904 A1 | 12/2014 | Parviainen |
| 2015/0012131 A1 | 1/2015 | Saltsov |
| 2015/0021349 A1 | 1/2015 | Sanders |
| 2015/0038898 A1 | 2/2015 | Palmer et al. |
| 2015/0044628 A1 | 2/2015 | Flyash |

(56) References Cited

U.S. PATENT DOCUMENTS

| | | |
|---|---|---|
| 2015/0048101 A1 | 2/2015 | Reddy et al. |
| 2015/0072300 A1* | 3/2015 | Wolpo .............. A61C 17/0217 433/32 |
| 2015/0072306 A1* | 3/2015 | Barnard .............. A61C 17/228 433/119 |
| 2015/0079533 A1 | 3/2015 | Lowe |
| 2015/0174348 A1 | 6/2015 | Tunnell et al. |
| 2015/0174349 A1 | 6/2015 | Tunnell et al. |
| 2015/0191268 A1 | 7/2015 | Paz |
| 2015/0191294 A1 | 7/2015 | Paz |
| 2015/0221086 A1 | 8/2015 | Bertram |
| 2015/0232256 A1 | 8/2015 | Hoover et al. |
| 2015/0257980 A1 | 9/2015 | Fung et al. |
| 2015/0259110 A1 | 9/2015 | Blackbum |
| 2015/0266654 A1 | 9/2015 | Baarman et al. |
| 2015/0272825 A1 | 10/2015 | Lim et al. |
| 2015/0273165 A1 | 10/2015 | Hadash |
| 2015/0291344 A1 | 10/2015 | Macvittie et al. |
| 2015/0305671 A1* | 10/2015 | Yoon ..................... A61M 21/02 600/301 |
| 2015/0317455 A1 | 11/2015 | Lehmann et al. |
| 2015/0320643 A1 | 11/2015 | Zhou |
| 2015/0328084 A1* | 11/2015 | Cash ..................... A61J 7/0092 604/79 |
| 2015/0342830 A1 | 12/2015 | Bujalski et al. |
| 2015/0347713 A1 | 12/2015 | Seeger |
| 2015/0359667 A1 | 12/2015 | Brue |
| 2016/0012249 A1 | 1/2016 | Keppler |
| 2016/0016720 A2 | 1/2016 | Paz |
| 2016/0022542 A1 | 1/2016 | Lehmann et al. |
| 2016/0029962 A1 | 2/2016 | Hyde |
| 2016/0037916 A1 | 2/2016 | Hermann |
| 2016/0038377 A1 | 2/2016 | Tegborg et al. |
| 2016/0042150 A1 | 2/2016 | Moloughney |
| 2016/0066776 A1 | 3/2016 | Weiss et al. |
| 2016/0096014 A1 | 4/2016 | Ajiki |
| 2016/0107820 A1 | 4/2016 | Macvittie et al. |
| 2016/0113747 A1 | 4/2016 | Almutairi |
| 2016/0117480 A1 | 4/2016 | Ervin |
| 2016/0128906 A1 | 5/2016 | Baarman et al. |
| 2016/0132660 A1 | 5/2016 | Barajas et al. |
| 2016/0136056 A1 | 5/2016 | Lapham |
| 2016/0145031 A1 | 5/2016 | Reinhold et al. |
| 2016/0158107 A1 | 6/2016 | Dvorak et al. |
| 2016/0166766 A1 | 6/2016 | Schuster et al. |
| 2016/0180693 A1 | 6/2016 | Johnson |
| 2016/0203292 A1 | 7/2016 | Kamen et al. |
| 2016/0211693 A1 | 7/2016 | Stevens et al. |
| 2016/0213606 A1 | 7/2016 | Palmer et al. |
| 2016/0213843 A1 | 7/2016 | Despa |
| 2016/0228333 A1 | 8/2016 | Bukstein et al. |
| 2016/0278899 A1* | 9/2016 | Heller ..................... A61P 25/16 |
| 2016/0331025 A1* | 11/2016 | Cameron ................. A24F 40/65 |
| 2017/0027675 A1 | 2/2017 | Nahshon |
| 2017/0028178 A1* | 2/2017 | Skoda ..................... A61B 5/4064 |
| 2017/0181475 A1 | 6/2017 | Cameron |
| 2017/0197025 A1* | 7/2017 | Adams ..................... G16H 20/17 |
| 2017/0265978 A1* | 9/2017 | Borotto ..................... A61C 19/05 |
| 2017/0290699 A1* | 10/2017 | Radmand .............. A61B 5/4557 |
| 2017/0304854 A1* | 10/2017 | Jacquemart ............ B05B 12/002 |
| 2017/0312181 A1 | 11/2017 | Davis et al. |
| 2017/0333649 A1 | 11/2017 | Djupesland |
| 2018/0110939 A1 | 4/2018 | Lanzkowsky |
| 2018/0333239 A1* | 11/2018 | Wen ..................... A61C 19/063 |

FOREIGN PATENT DOCUMENTS

| | | |
|---|---|---|
| CN | 105263552 | 1/2016 |
| CN | 105873631 | 8/2016 |
| DE | 102014114601 A1 | 4/2016 |
| JP | 2008-517646 A | 5/2008 |
| JP | 2009-526553 A | 7/2009 |
| JP | 2010-240189 A | 10/2010 |
| KR | 101221415 B1 | 1/2013 |
| WO | WO2004062717 A1 | 7/2004 |
| WO | WO 2010062675 | 6/2010 |
| WO | WO2011151056 A1 | 12/2011 |
| WO | WO 2013062785 | 5/2013 |
| WO | WO2015150240 A1 | 10/2015 |
| WO | WO2015172962 A1 | 11/2015 |
| WO | WO2015181693 A1 | 12/2015 |
| WO | WO2015196293 A1 | 12/2015 |
| WO | WO2015196336 A1 | 12/2015 |
| WO | WO2016064592 A1 | 4/2016 |
| WO | WO2016064688 A1 | 4/2016 |
| WO | WO2016064786 A1 | 4/2016 |
| WO | WO2016064906 A1 | 4/2016 |
| WO | WO2016064908 A1 | 4/2016 |
| WO | WO2016116591 A1 | 7/2016 |
| WO | WO2017064709 A1 | 4/2017 |
| WO | WO2017218947 A1 | 12/2017 |
| WO | WO 2018/075979 A1 | 4/2018 |
| WO | WO 2018/075981 A2 | 4/2018 |
| WO | WO 2019178367 | 9/2019 |

OTHER PUBLICATIONS

Written Opinion issued in PCT/US2018/013440 dated Mar. 9, 2018.
International Search Report issued in PCT/US2019/022287 dated Jul. 16, 2019.
Written Opinion issued in PCT/US2019/022287 dated Jul. 16, 2019.
Australian Office Action, Application No. 2019235911, dated Mar. 25, 2021, 3 pages.
Chinese Office Action, Application No. 201880013266.6, dated Dec. 18, 2020, 7 pages.
Australian Office Action, Application No. 2019235911, dated Jan. 13, 2021, 6 pages.
New Zealand Patent Office, Examination Report, Application No. 767645, dated Aug. 5, 2021, 4 pages.
Australian Patent Office, Australian Office Action—Notice of Acceptance, for Application No. 2019235911, dated Nov. 3, 2021, 3 pages.
Australian Patent Office, Examination Report, Application No. 2019235911, dated Jul. 14, 2021, 5 pages.
Japanese Patent Office, Japanese Office Action—for Application No. 2020-548946, dated Nov. 9, 2021, with Translation, 7 pages.
European Patent Office, European Office Action, for Application No. 19768054.9-1113, dated Oct. 22, 2021, 7 pages.

* cited by examiner

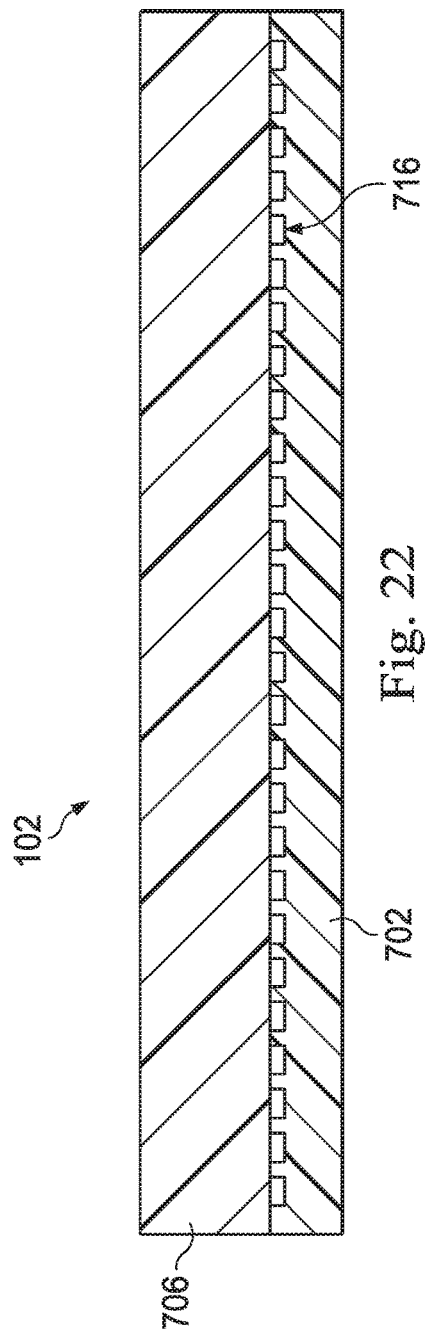
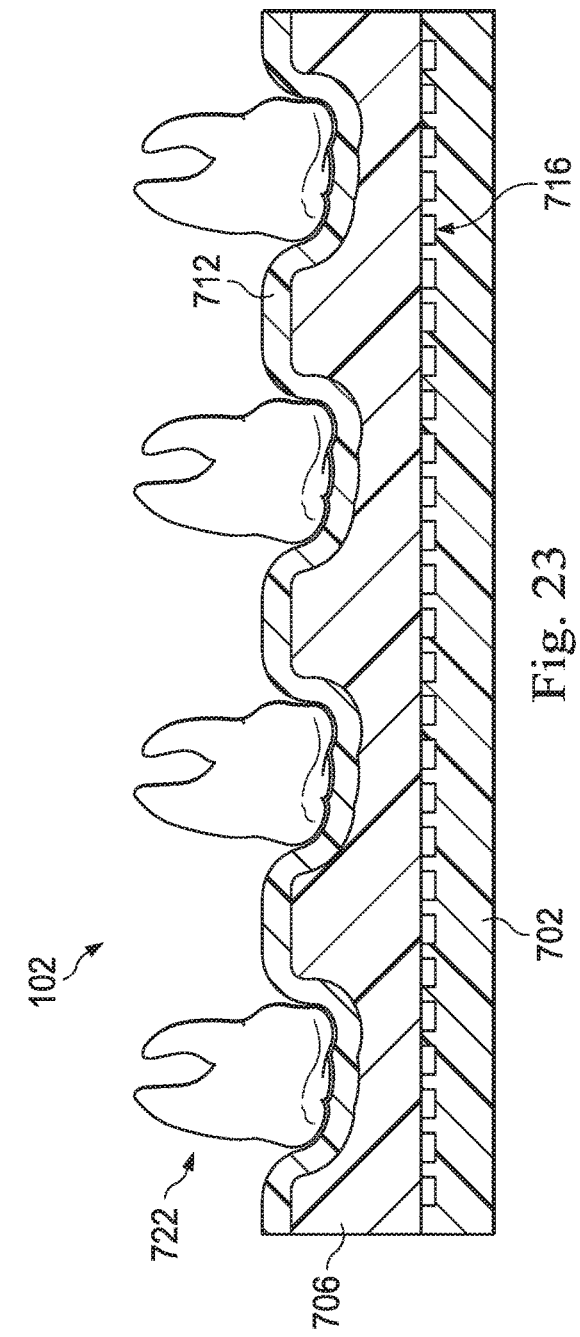

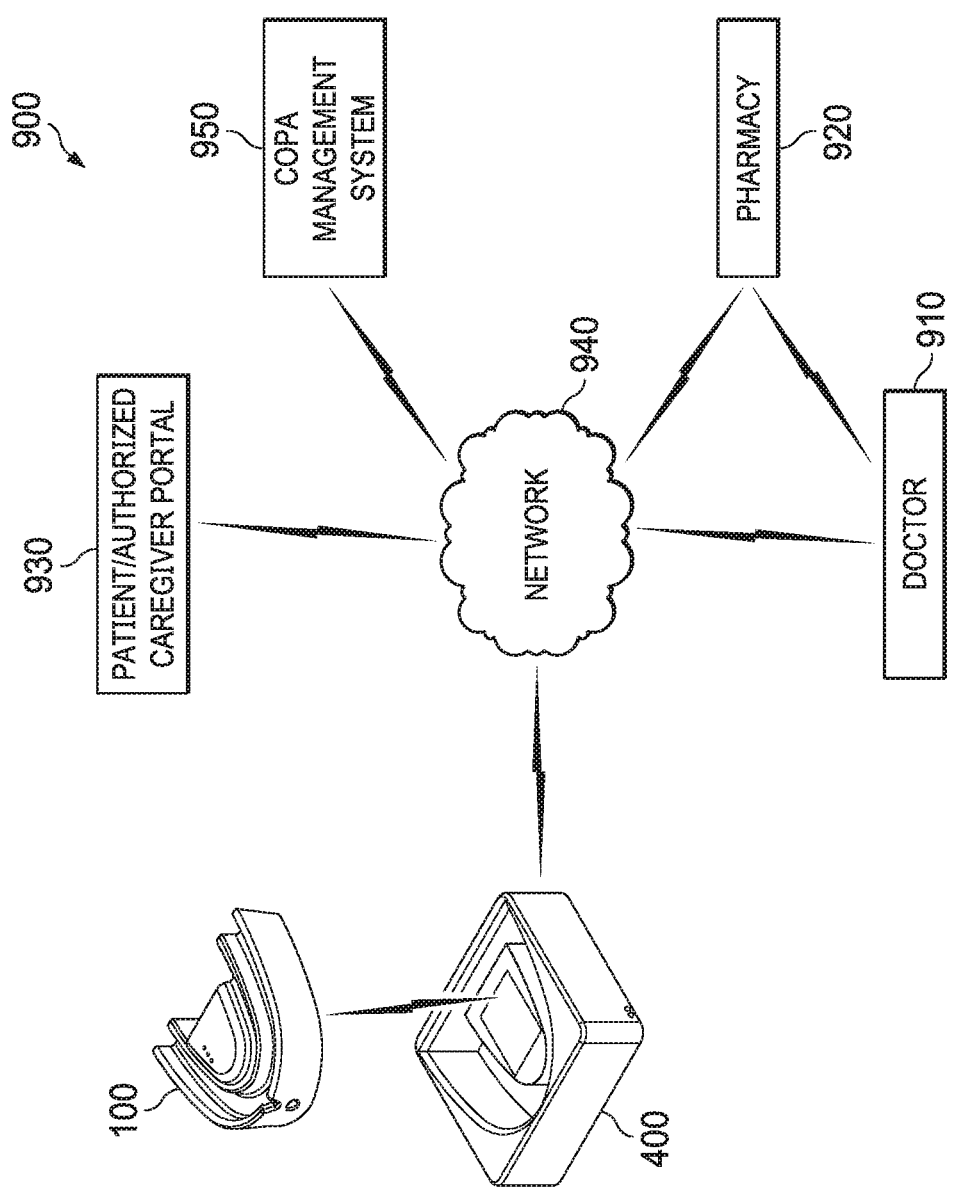

COMPUTERIZED ORAL PRESCRIPTION ADMINISTRATION WITH REFILLABLE MEDICATION DISPENSING DEVICES AND ASSOCIATED SYSTEMS AND METHODS

CROSS REFERENCE TO RELATED APPLICATIONS

The present application is a divisional application of U.S. patent application Ser. No. 15/958,809, filed Apr. 20, 2018, which claims priority to and the benefit of the U.S. Provisional Patent Application No. 62/644,145, filed Mar. 16, 2018, each of which is hereby incorporated by reference in its entirety.

TECHNICAL FIELD

The present disclosure relates generally to pharmaceutical oral dose administration devices and computerized oral prescription administration (COPA) devices. For example, capacitance sensor(s), environmental sensor(s), and biometric sensor(s) can be implemented in COPA devices for sensing the position of a patient's dentition, sensing when the COPA device is inside the patient's mouth, and/or sensing biometric attributes of the patient.

INTRODUCTION

The history of pharmacology has produced a continual evolution of routes of administration, pharmaceutical formulations, dosage forms, and dosing devices in a continuing quest towards maximizing the effective benefit and relative costs of prescription medications. Administration of prescribed substances may begin in controlled healthcare settings, for example, at a healthcare facility or by a physician at a patient's home. Early-stage formulations may include liquid forms for parenteral (e.g., into a blood stream) and enteral (e.g., into a gastro-intestine) administration including elixirs, tonics, solutions, suspensions, syrups and eventually injections, intravenous (IVs), and epidurals. The early-stage formulations may be developed to produce advanced forms, for example, via mechanization and formulation research. The early-stage formulations, the advanced forms, and further research and clinical studies such as patient acceptances of the early-stage formulations and/or the advanced forms may contribute to the routes of administration, pharmaceutical formulations, dosage forms, and dosing devices.

As the healthcare treatment transitioned from limited emergency involvement into longer term chronic illness care, higher percentages of the prescribed medication administration shifted from the controlled healthcare settings to patient managed settings. In a patient managed setting, outside the control of a trained healthcare staff, the administration of liquid formulations may be difficult due to non-specific dosing instructions. Dosing based on teaspoon and/or tablespoon measurements may be vague and variable. Dosing cups may have different measurement formats, and thus may cause confusion in a patient managed setting. In addition, dosing cups are often separated from initial prescription bottles, and thus may lead to erroneous administration.

The advancements of mechanical manufacturing systems and pharmacology research enabled patient managed administrations of prescribed substances to shift from liquid formulations to pills (e.g., tablets or capsule-formulations), which may have increased shelf life and allow for patient ease of use, dosing exactness, and production cost reductions. Thus, a majority of oral medications in patient managed settings are now pills. Additionally, there is an increased interest in microparticulate formulations including pellets, granules, micro particles, mini tablets, and the like. However, patients, such as infants, elderly, or impaired patients, that cannot or prefer not to swallow tablets or capsule-formulations may be given enteral oral liquid prescriptions through dosing syringes in patient managed settings. In addition, parenteral liquid formulations are still commonly administered in controlled healthcare settings since the parenteral liquid formulations often have the fastest rate of absorption and the most expedient success in the desired result and can improve localized administration, inventory control, fraud prevention, and administration path audit capability.

Depending on the entity managing the administration of a drug, various forms of the drug may be developed to meet expectations, needs, and challenges of different entities. While there are some exceptions based on effectiveness and toxicity, most pharmaceutical manufacturers may produce multiple formulations of drugs to support different routes of administration and dosing.

There is a growing demand for drug administration in patient controlled or managed settings as consumers increasingly engage in preventative or resultative treatment plans, which involve drug administration in patient controlled settings. For example, outpatient surgeries and/or one-day inpatient surgery stays are increasingly common for significant medical procedures, which may involve subsequent drug administrations at a patient's home. In addition, as the population ages, the demand for prescription management increases. Consumers may take multiple over-the-counter and/or prescribed medicines daily, where the medicines are commonly in the form of pills. Unfortunately, the ease-of-use of pills and the increasing number of consumers engaged in chronic patient managed treatment plans has led to misuse and mismanagement of many drug classes.

For example, pill forms are lightweight, portable, recipient non-specific, difficult for inventory management, don't carry individual identification numbers, have extensive shelf life, and are inexpensive to produce. Thus, the intakes or usages of pills are difficult to control once outside of healthcare managed environments. In addition, to achieve the economy of scale in the manufacturing process, pill production is scheduled based on maximizing the output of the machines, materials, and/or ingredients available instead of based on future demands. With a few exceptions, a minimal amount of the pills produced are wasted since pills remain active for a long time. Pills proliferate our society and have become conduits to addiction and abuse.

One such patient managed treatment that is highly susceptible to prescription misuse and mismanagement is opioid pain treatment. For example, according to the Food and Drug Administration (FDA), approximately 100 million people in the United States (US) suffer from pain in a given year. About 9 to 12 million of the pain sufferers have chronic or persistent pain, while the remaining pain sufferers have short-term pain from injuries, illnesses, or medical procedures. In 2014, the Centers for Disease Control and Prevention reported that the number of annual opioid prescriptions in the US is about equal to the number of adults in the US population. While pain sufferers should benefit from skillful and appropriate pain management, the misuse or addiction of opioids needs to be controlled. FDA leaders and physicians attempt to address the opioid epidemic by balancing two complementary principles: deal aggressively with opioid misuse and addiction while protecting the well-being of people experiencing acute or chronic pains. However, the pain sufferers in areas where reforms, policies, and restrictions aimed at opioid misuse have been implemented may not experience the balance. Some states have implemented additional known addict or misuser databases that must be checked by providers prior to prescribing. However, physicians may not check the databases prior to prescribing due to the burden of using the systems and/or they may not want to restrict access by true chronic pain sufferers. Other states have implemented reporting and audit trails to track physicians that have prescribed from the opioid family. However, to avoid the additional steps and potentials for audit scrutiny, some physicians may refuse to offer pain management or short-term pain prescriptions, and may refer all cases to pain clinics.

Attempts at improved patient education, enhanced labeling, and restrictive prescribing have led to higher costs for providers, patients, pharmacies, and insurance companies and less overall effectiveness for the patients. In the end, true pain sufferers struggle to have access to opioids while opioid misusers continue to manipulate the available avenues for access regardless of the apparent oversights put in place. Policies and plans at various levels have not been successful and are not sufficient to control or reduce the misuse of prescription drugs. Accordingly, improved devices, systems, and methods for drug administration are needed.

SUMMARY

The following summarizes some aspects of the present disclosure to provide a basic understanding of the discussed technology. This summary is not an extensive overview of all contemplated features of the disclosure, and is intended neither to identify key or critical elements of all aspects of the disclosure nor to delineate the scope of any or all aspects of the disclosure. Its sole purpose is to present some concepts of one or more aspects of the disclosure in summary form as a prelude to the more detailed description that is presented later.

The present disclosure provides computerized oral prescription administration (COPA) devices, systems, and methods with capacitive dentition sensing, environmental sensing, and refill and dosage management. These COPA devices, systems, and methods facilitate the controlled dispensing of medication to an intended user. In this regard, the identification of the intended user can be verified based on a capacitive map of the user's dentition before dispensing the medication. The capacitive map can be detected by a capacitive sensor array coupled to or embedded in a mouthpiece that is positioned inside the intended user's mouth. Additionally, environmental sensor(s) can detect whether the COPA device is positioned within the intended user's mouth. Additional verification devices, systems, and methods may also be used to authenticate the intended user. For example, a biometric sensor may be used to detect a biometric attribute of the intended user, such as the intended user's fingerprint, to authenticate the intended user. Parameters associated with the dispensing of medication (e.g., medication, dosage amount, timing, intended user information, etc.) can be tracked, stored in a COPA management system, and/or communicated throughout the healthcare continuum, including medical personnel, pharmaceutical personnel, patient, authorized caregivers, and/or insurers, such that patient's compliance with a treatment plan can be evaluated and/or the effectiveness of the treatment plan can be evaluated. Additionally, the COPA management system can send out alerts to participants of the healthcare continuum to serve as notices, reminders, and/or issues.

In one embodiment, a substance dispensing apparatus is provided. The apparatus includes a mouthpiece having a recess and a first capacitive sensor array adjacent to the recess; a processor in communication with the first capacitive sensor array, the processor configured to determine whether an intended user's unique dentition is positioned within the recess of the mouthpiece based on input received from the first capacitive sensor array; and an actuator in communication with the processor, the actuator configured to dispense a substance from a reservoir to a mouth of the intended user in response to the processor determining that the intended user's unique dentition is positioned within the recess of the mouthpiece.

In some embodiments, the mouthpiece comprises a first side having a first outer layer adjacent to the recess, a first intermediate layer positioned under and in contact with the first outer layer, and a base layer positioned under and in contact with the first intermediate layer. In some embodiments, the first outer layer comprises a capacitive material. In some embodiments, the mouthpiece further comprises a second side having a second outer layer adjacent to a second recess of the mouthpiece and a second intermediate layer positioned under and in contact with the second outer layer. In some embodiments, the second outer layer comprises a capacitive material. In some embodiments, the mouthpiece further comprises a second capacitive sensor array adjacent to the second recess, where the second capacitive sensor array is embedded within the base layer. In some embodiments, the second outer layer is removably coupled to the second intermediate layer. In some embodiments, the base layer is positioned under and in contact with the second intermediate layer, the base layer being positioned between the first and second intermediate layers. In some embodiments, the first outer layer is removably coupled to the first intermediate layer. In some embodiments, the first capacitive sensor array is embedded within the base layer.

In some embodiments, the mouthpiece comprises a first side having a first intermediate layer adjacent to the recess and a base layer connected to the first intermediate layer. In some embodiments, the recess of the mouthpiece is sized and shaped to receive a plurality of users' dentitions, where the plurality of users' dentitions comprises different sizes. In some embodiments, the first capacitive sensor array includes one or more capacitive sensors. In some embodiments, the processor is positioned within the mouthpiece. In some embodiments, the processor is spaced from the mouthpiece. In some embodiments, the processor is positioned within a computing device spaced from the mouthpiece. In some embodiments, the actuator is positioned within the mouthpiece. In some embodiments, the actuator is spaced from the mouthpiece. In some embodiments, the mouthpiece is coupled to a housing, the actuator being positioned within the housing. In some embodiments, the reservoir is positioned within the mouthpiece. In some embodiments, the reservoir is spaced from the mouthpiece. In some embodiments, the reservoir is a pharmaceutical medication bottle.

In one embodiment, a method of dispensing a substance to an intended user is provided. The method includes receiving an input from a capacitive sensor array of a mouthpiece; determining, based on the received input, whether an intended user's unique dentition is positioned within a recess of the mouthpiece; and dispensing a substance from a reservoir to a mouth of the intended user in response to determining that the intended user's unique dentition is positioned within the recess of the mouthpiece.

In some embodiments, capacitance data associated with the input received from the capacitive sensor array is compared to predetermined capacitance data associated with the intended user's unique dentition. In some embodiments, the reservoir is positioned outside the mouth, and the substance is dispensed to the mouth from the reservoir outside the mouth. In some embodiments, the reservoir is positioned inside the mouth, and the substance is dispensed to the mouth from the reservoir inside the mouth.

In one embodiment, a method of registering a substance dispensing apparatus to an intended user is provided. The method includes receiving, from a capacitive sensor array of a mouthpiece, an input associated with an intended user's unique dentition biting on the mouthpiece; and registering, based on the received input, the intended user to the mouthpiece.

In some embodiments, the method further comprises storing the received input in memory integrated in the substance dispensing apparatus. In some embodiments, the received input is representative of a capacitive map of the intended user's unique dentition. In some embodiments, a plurality of inputs is received to define a range of acceptable matches associated with the intended user's unique dentition biting on the mouthpiece.

In one embodiment, a substance dispensing apparatus is provided. The apparatus includes a housing sized and shaped for handheld use, the housing having at least one wall and a biometric sensor coupled to the at least one wall; a processor in communication with the biometric sensor, the processor configured to determine whether an intended user's unique biometric attribute is detected by the biometric sensor based on input received from the biometric sensor; and a pump in communication with the processor, the pump configured to dispense a substance from a reservoir to a mouth of the intended user in response to the processor determining that the intended user's unique biometric attribute is detected by the biometric sensor.

In some embodiments, the biometric sensor is positioned on a first face of the at least one wall. In some embodiments, the biometric sensor is sized and shaped to receive biometric attributes of a plurality of users, where the biometric attributes of the plurality of users comprise different sizes. In some embodiments, the reservoir is a pharmaceutical medication bottle configured to hold a liquid. In some embodiments, the at least one wall comprises a surface texturing feature to facilitate a user's grip of the housing during the handheld use. In some embodiments, the at least one wall of the housing comprises a bottom wall and another wall coupled to the bottom wall.

In some embodiments, the apparatus further comprises a locking mechanism configured to securely seal the bottom wall to the another wall when the another wall is coupled to the bottom wall. In some embodiments, the housing further comprises a cavity defined by the at least one wall. In some embodiments, the pump is positioned within the cavity of the housing. In some embodiments, the apparatus further comprises the reservoir, wherein the reservoir is positioned within the cavity of the housing. In some embodiments, the housing further comprises a cap positioned above and in contact with the reservoir and a tubular member connecting the pump to a mouthpiece positioned outside of the housing, where the cap is connected to the pump via a connecting member. In some embodiments, the processor is coupled to the mouthpiece. In some embodiments, a distal end of the tubular member is connected to a proximal end of the pump, and a proximal end of the tubular member is connected to the mouthpiece.

In some embodiments, the cap comprises threads, and the reservoir comprises grooves configured to receive the threads to couple the cap and the reservoir. In some embodiments, at least one of the cap, the connecting member, or the tubular member is positioned within the cavity of the housing. In some embodiments, the cap comprises a valve and a dip tube positioned below and in contact with the valve, where the valve is configured to regulate an amount of the substance disposed within the tubular member and the connecting member. In some embodiments, the dip tube extends from a proximal end connected to the valve to a distal end terminating above a base of the reservoir. In some embodiments, substantially all of a length of the dip tube is positioned within the reservoir. In some embodiments, a distal end of the connecting member is coupled to a proximal end of the valve, and a proximal end of the connecting member is coupled to a distal end of the pump.

In one embodiment, a method of dispensing a substance to an intended user is provided. The method includes receiving an input from a biometric sensor; determining, based on the received input from the biometric sensor, whether an intended user's unique biometric attribute is detected by the biometric sensor; receiving an input from an environmental sensor; determining, based on the received input from the environmental sensor, whether a mouthpiece is positioned within a user's mouth; receiving an input from a capacitive sensor array of the mouthpiece; determining, based on the received input from the capacitive sensor array, whether an intended user's unique dentition is positioned within a recess of the mouthpiece; and dispensing a substance from a reservoir to a mouth of the intended user in response to determining that the intended user's unique biometric attribute is detected by the biometric sensor.

In some embodiments, the received input from the biometric sensor is representative of a fingerprint model of the intended user. In some embodiments, a fingerprint model associated with the input received from the biometric sensor is compared to a predetermined fingerprint model associated with the intended user's unique biometric attribute. In some embodiments, the method further comprises dispensing the substance from the reservoir to the mouth of the intended user in response to determining that the mouthpiece is positioned within the user's mouth. In some embodiments, the method further comprises dispensing the substance from the reservoir to the mouth of the intended user in response to determining that the intended user's unique dentition is positioned within the recess of the mouthpiece.

In some embodiments, the method further comprises registering, based on the received input from the biometric sensor, the intended user to a housing coupled to the biometric sensor. In some embodiments, the method further comprises storing the received input from the biometric sensor in memory coupled to the housing. In some embodiments, a plurality of inputs is received to define a range of acceptable matches associated with the intended user's unique biometric attribute contacting the housing. In some embodiments, the method further comprises receiving, from a capacitive sensor array of a mouthpiece, an input associated with an intended user's unique dentition being within the mouthpiece; and registering, based on the received input from the capacitive sensor array, the intended user to the mouthpiece. In some embodiments, a plurality of inputs is received to define a range of acceptable matches associated with the intended user's unique dentition being positioned within the recess of the mouthpiece. In some embodiments, the substance is dispensed from the reservoir to the mouth of the intended user automatically in response to determining that the intended user's unique biometric attribute is detected by the biometric sensor.

In one embodiment, a method of dispensing a substance to an intended user is provides. The method includes receiving an input from a biometric sensor coupled to at least one wall of a housing defining a cavity sized and shaped to receive at least a portion of a reservoir, the housing sized and shaped for handheld use; determining, based on the received input from the biometric sensor, whether an intended user's unique biometric attribute is detected by the biometric sensor; receiving an input from a dentition sensing element of a mouthpiece, the mouthpiece coupled to the housing; determining, based on the received input from the dentition sensing element, whether an intended user's unique dentition is positioned within a recess of the mouthpiece; and dispensing, by a pump coupled to the mouthpiece, a substance from the reservoir to a mouth of the intended user in response to determining that the intended user's unique biometric attribute is detected by the biometric sensor.

In some embodiments, the method further comprises receiving an input from an environmental sensor; and determining, based on the received input from the environmental sensor, whether the mouthpiece is positioned within a user's mouth. In some embodiments, the substance is dispensed from the reservoir to the mouth of the intended user in response to determining that the mouthpiece is positioned within the user's mouth. In some embodiments, the substance is dispensed from the reservoir to the mouth of the intended user in response to determining that the intended user's unique dentition is positioned within the recess of the mouthpiece. In some embodiments, the method further comprises registering, based on the received input from the biometric sensor, the intended user to the housing; and storing the received input from the biometric sensor in memory coupled to the housing.

In some embodiments, the substance is dispensed from the reservoir, through a cap positioned within the cavity of the housing, and to the mouth of the intended user. In some embodiments, the method further comprises registering, based on the received input from the dentition sensing element, the intended user to the mouthpiece. In some embodiments, the dentition sensing element is a capacitive sensor array. In some embodiments, the substance is dispensed from the reservoir to the mouth of the intended user automatically in response to determining that the intended user's unique biometric attribute is detected by the biometric sensor.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 22 is a cross-sectional view of a top side of a COPA device along section line 18-18 in FIG. 1 according to embodiments of the present disclosure.

FIG. 23 is a cross-sectional view of a top side of a COPA device in a deformed state along section line 18-18 in FIG. 1 according to embodiments of the present disclosure.

FIG. 26 is a schematic diagram of a COPA system according to embodiments of the present disclosure.

DETAILED DESCRIPTION

Figure 1:
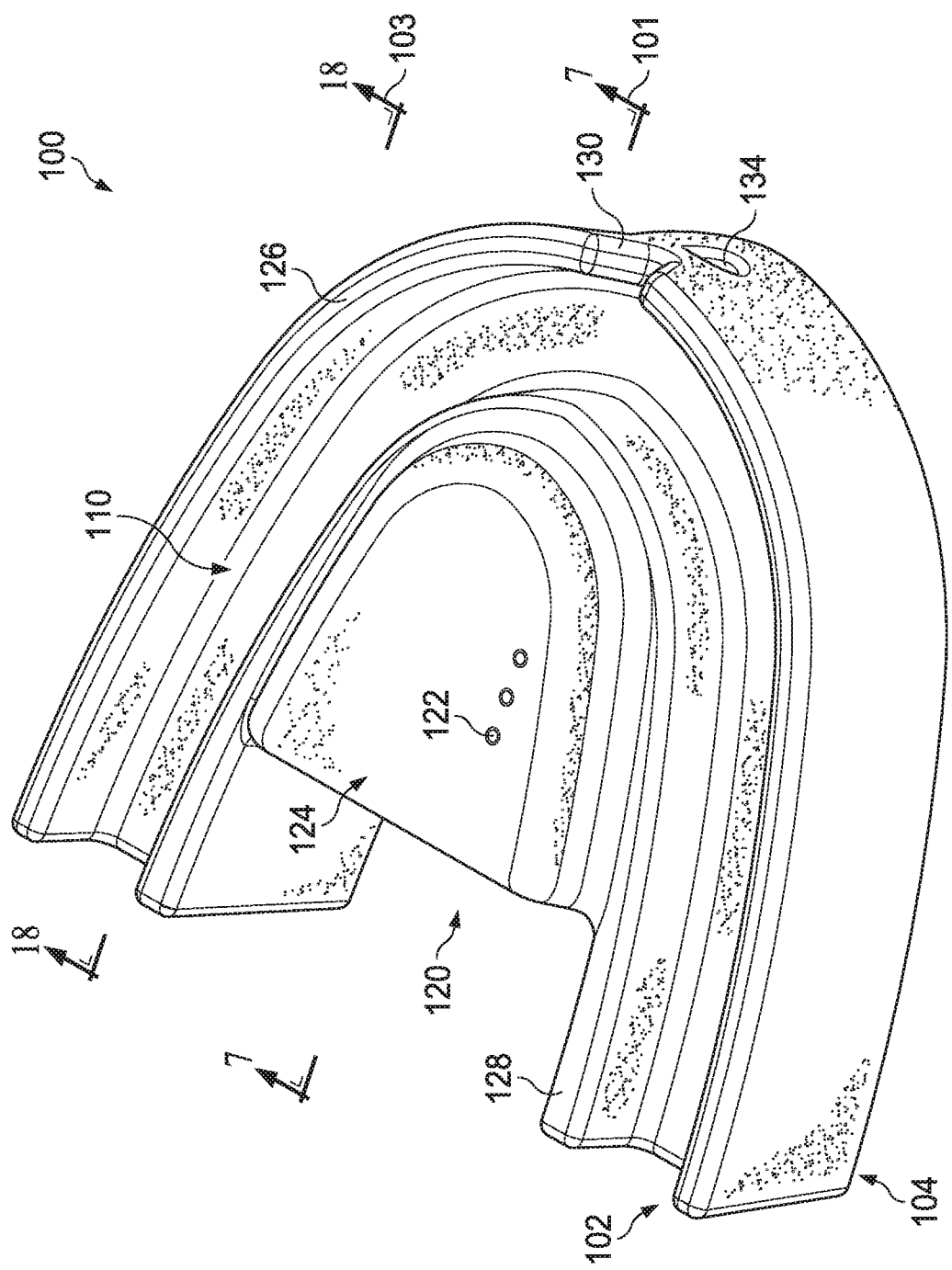
FIG. 1 is a top perspective view of a computerized oral prescription medication (COPA) device according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates.

Embodiments of the present disclosure provide mechanisms for administering enteral oral medications through an ID-specific device registered with a centralized management system. In an embodiment, a substance dispensing apparatus (e.g., a COPA device) includes a mouthpiece including a recess and a capacitive sensor array adjacent to the recess. The mouthpiece may include a capacitive sensor array including a plurality of capacitance sensors positioned at various locations within the recess. The mouthpiece may include an environmental sensor coupled to a mouthpiece, such as an environmental sensor positioned on a face of a wall of the mouthpiece. The mouthpiece may include a micro-pump unit including a processor, a reservoir, an actuator, flow channels, and exit valves. The reservoir may be filled with prescribed or over-the-counter medications. The processor may be in communication with the capacitive sensor array and the actuator. To administer the medications, the patient may insert the mouthpiece into the patient's mouth and close the mouth to bite on the mouthpiece. The capacitive sensor array may sense and measure the capacitance associated with the user's dentition and bite. The processor may determine whether a match is found between the measured capacitance and pre-recorded data of the intended recipient. The processor may determine whether the mouthpiece is positioned correctly. The environmental sensor may sense and measure attributes of the environment (e.g., the temperature) surrounding the mouthpiece. The processor may determine whether the mouthpiece is located within the user's mouth. Upon detecting a match and correct positioning and location, the processor may activate the actuator to release an exact dosage of the medications through the flow channels and exit valves into the patient's mouth for ingestion. In an embodiment, the centralized management system may track the creation and preparation of the mouthpiece, the filling of the prescribed medications, and/or the administration or dispensing of the prescribed medications through various identification mechanisms.

The disclosed embodiments may provide several benefits. For example, the employment of the individually registered mouthpiece with the embedded processor and the centralized management system can ensure that the prescribed medications are delivered to the intended recipient. Thus, the disclosed embodiments may avoid misuse and mismanagement of prescription medications. In addition, the disclosed embodiments may allow healthcare providers and insurance companies to better track the administering of the prescribed medications and evaluate the benefits, effects, and/or results of the prescribed medications more accurately. The disclosed embodiments may deliver a precise dosage of prescribed medications to patients and may especially benefit patients that are elderly, impaired, or have behavioral issues that may limit their abilities to self-administer prescribed medications. While the disclosed embodiments are described in the context of using a capacitive map as a form of verification for matching a prescription to an intended user, other biological markings (fingerprint, retina or iris scans, DNA, voice recognition, etc.) may also be applied or used in conjunction with and/or in lieu of the capacitive map. In addition, the employment of a capacitive sensor array can ensure that one mouthpiece may be used for several users (with only one intended user registered to the mouthpiece at a time). Thus, the disclosed embodiments may avoid burdensome production costs.

FIG. 1 is a top perspective view of a COPA device 100 according to embodiments of the present disclosure. The COPA device 100 may be used for delivering enteral oral liquid, multiparticulate, and/or other forms of drugs to an intended patient or user with controlled dosing. The COPA device 100 is a mouthpiece including a top side 102. The top side 102 may include a capacitive sensor array in one or more layers forming the top side. Exemplary arrangements of the one or more layers are described in FIGS. 18-25B. A top side outer layer of the top side 102 may be substantially planar. This may allow the COPA device 100 to fit within a plurality of different mouths with a plurality of different dentitions. In some embodiments, the capacitive sensor array may detect a capacitive map when the user bites down on the top side 102 of the COPA device 100. The capacitive map may be compared to a pre-determined capacitive map of the user's dentition as a form of verification to identify an intended recipient of a prescribed substance, as described in greater detail herein.

The COPA device 100 may also include a front wall portion 126 and a back wall portion 128. The front and back wall portions 126, 128 extend out from the COPA device 100 and define a recess 110. In some embodiments, the front and back wall portions 126, 128 may be perpendicular to a top surface of a top side outer layer of the COPA device 100. In other embodiments, the front and back wall portions 126, 128 may be angled (i.e., not perpendicular) relative to a top surface of a top side outer layer of the COPA device 100. The top side 102 may be configured to receive a corresponding first portion of the user's dentition (e.g., the user's upper teeth). Therefore, in some embodiments, the user may place the user's upper teeth in the recess 110. The recess 110 may be sized and shaped to receive a plurality of users' dentitions, and the plurality of users' dentitions may comprise different sizes. In some embodiments, the COPA device 100 may also include a cutout portion 130 to further accommodate different mouth shapes of different users. Additionally, the COPA device 100 may be constructed from a biocompatible impression material or polymer.

The COPA device 100 further includes a sealed prescription dispensing unit 120. The sealed prescription dispensing unit 120 may be positioned at the top center of the COPA device 100. In some embodiments, the sealed prescription dispensing unit 120 may not be coupled to the COPA device 100. The sealed prescription dispensing unit 120 may be located in an external housing that may be coupled to the COPA device 100. The sealed prescription dispensing unit 120 may include a sealed sleeve 124 and a plurality of access ports 122 extending from a top side of the sealed sleeve 124 into the prescription dispensing unit 120. The access ports 122 may be configured to receive prescribed substances. For example, a clinician or pharmacy technician may fill prescribed substances into the prescription dispensing unit 120 via the access ports. The prescribed substances may include formulations in various forms, such as liquid and/or multi-particulate. The prescription dispensing unit 120 may include other components, such as a processor, chambers, flow channels, actuators (e.g., micro-pumps), and exit valves, as described in greater detail herein.

The COPA device 100 may provide patient identification functionalities via the patient's capacitive map as detected by the capacitive sensor array. For example, each individual has a unique dental imprint, which corresponds to a unique capacitive map. While there are certain patterns for the ages at which certain teeth may erupt, mature, and be replaced with permanent teeth and for alignment of teeth types, the setting, size, angle, distance between certain points within a patient's mouth, and the resulting bite are different for different patients. In addition, damaged teeth, missing teeth, filled teeth, capped teeth, and prosthetics such as crowns, bridges, partial, and full dentures further the identifying nature or uniqueness of the mouths of different individuals. Thus, the use of the COPA device 100 with the dentition imprint corresponding to a unique capacitive map can be effective in identifying a particular individual. The COPA device 100 may provide further patient identification functionalities via various patient verification mechanisms implemented by a processor coupled to the mouthpiece (e.g., embedded within the sealed prescription dispensing unit 120), as described in greater detail herein.

The COPA device 100 further provides controlled prescription administration functionalities via the sealed prescription dispensing unit 120. For example, the processor may be in communication with the capacitive sensor array and configured to determine whether the COPA device 100 is correctly positioned within the intended user's mouth. Upon detecting a matching capacitive map, the processor may control the components within the sealed prescription dispensing unit 120 to release or deliver an exact dosage of the prescribed substances into the intended user's mouth, as described in greater detail herein.

Figure 2:
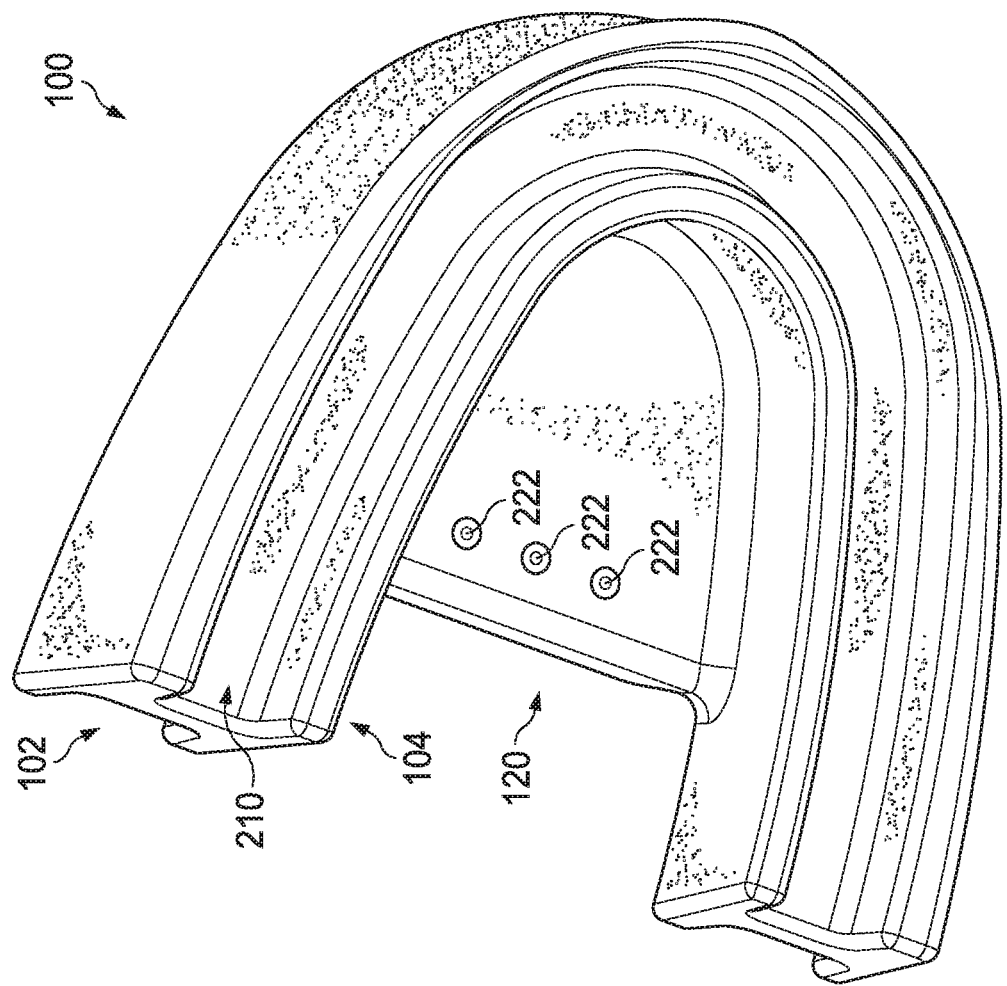
FIG. 2 is a bottom perspective view of a COPA device according to embodiments of the present disclosure.

FIG. 2 is a bottom perspective view of the COPA device 100 according to embodiments of the present disclosure. The bottom side 104 may include a capacitive sensor array in one or more layers forming the top side. Exemplary arrangements of the one or more layers are described in FIGS. 12-18B. A bottom side outer layer of the bottom side 104 may be substantially planar. This may allow the COPA device 100 to fit within a plurality of different mouths with a plurality of different dentitions. In some embodiments, the capacitive sensor array may detect a capacitive map when the user bites on the bottom side 104 of the COPA device 100. The prescription dispensing unit 120 includes a plurality of exit valves 222 on the bottom side 104, where prescribed substances may be released. Additionally, in some embodiments, the front and back wall portions 126, 128 (FIG. 1) extend out from the COPA device 100 and define a recess 210. In some embodiments, the front and back wall portions 126, 128 may be perpendicular to a top surface of a top side outer layer of the COPA device 100. In other embodiments, the front and back wall portions 126, 128 may be angled (i.e., not perpendicular) relative to a top surface of a top side outer layer of the COPA device 100. The bottom side 104 may be configured to receive a corresponding second portion of the user's dentition (e.g., the user's lower teeth). Therefore, in some embodiments, the user may place the user's lower teeth in the recess 210. The recess 210 may be sized and shaped to receive a plurality of users' dentitions, and the plurality of users' dentitions may comprise different sizes.

As discussed above, FIG. 1 and FIG. 2 illustrate embodiments of the COPA device 100 where the recesses 110, 210 and the front and back wall portions 126, 128 are configured to receive both upper teeth and lower teeth of a user. In some embodiments, though, the COPA device 100 only includes the recess 110 (see FIG. 18). For example, the front and back wall portions 126, 128 may be configured to fit around the user's upper teeth as the user's upper teeth are received in the recess 110. In other embodiments, the COPA device 100 only includes the recess 210 (see FIG. 20). For example, the front and back wall portions 126, 128 may be configured to fit around the user's lower teeth as the user's lower teeth are received in the recess 210. In further embodiments (e.g., the embodiments shown in FIG. 1 and FIG. 2), the COPA device 100 includes both of the recesses 110, 210. For example, the front and back wall portions 126, 128 may be configured to fit around the user's upper and lower teeth as the user's upper and lower teeth are received in the recesses 110 and 210, respectively.

Figure 3:
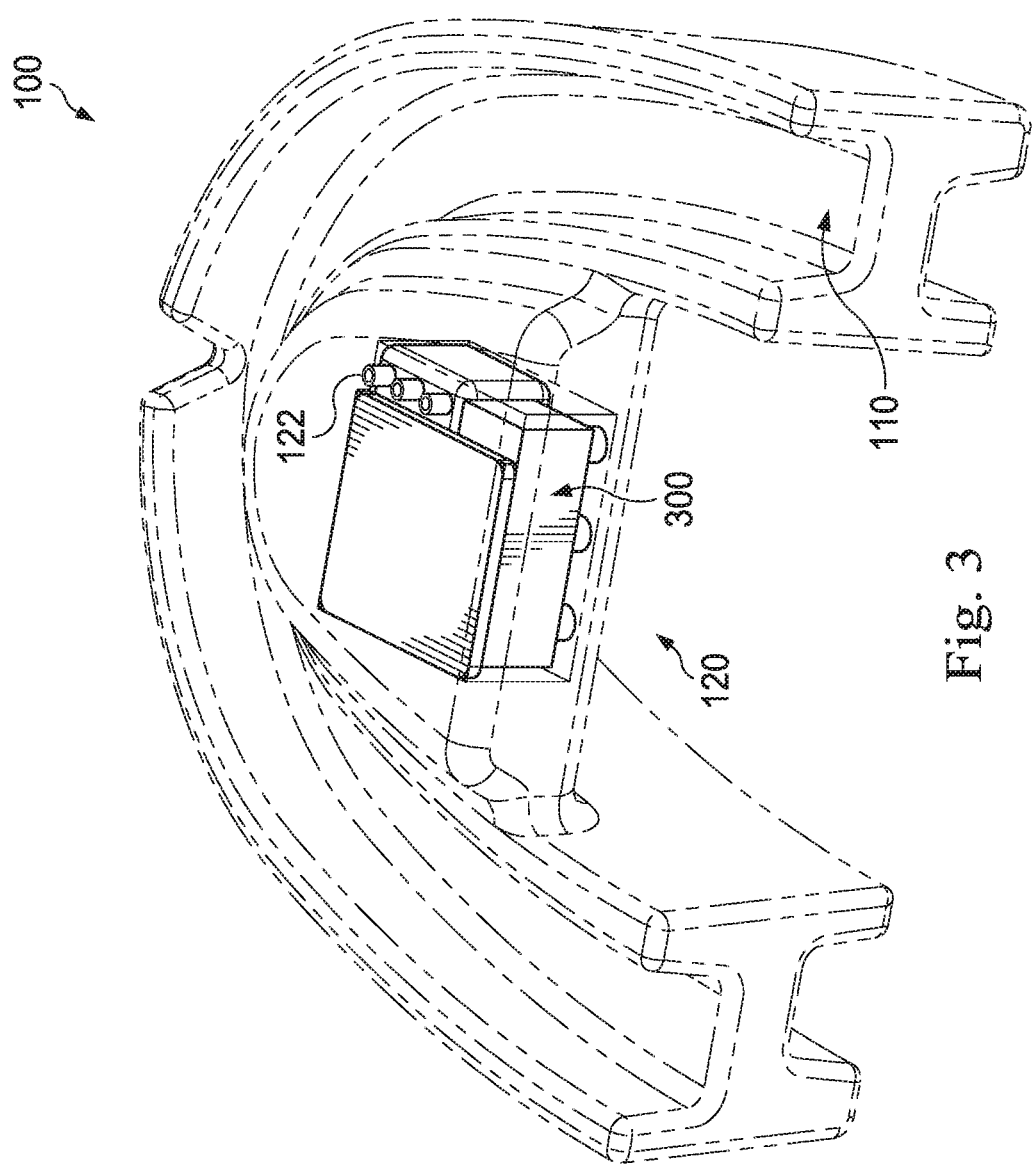
FIG. 3 is a perspective view of a COPA device coupled with a pre-packaged micro-pump unit according to embodiments of the present disclosure.

FIG. 3 is a perspective view of the COPA device 100 according to embodiments of the present disclosure. FIG. 3 illustrates the COPA device 100 with an upper portion of the sealed sleeve 124 (shown in FIG. 1) removed to provide a more detailed view of the prescription dispensing unit 120. As shown, the prescription dispensing unit 120 includes a micro-pump unit 300. The access ports 122 may be in communication with the micro-pump unit 300 to allow prescribed substances to be filled into the micro-pump unit 300.

Figure 4:
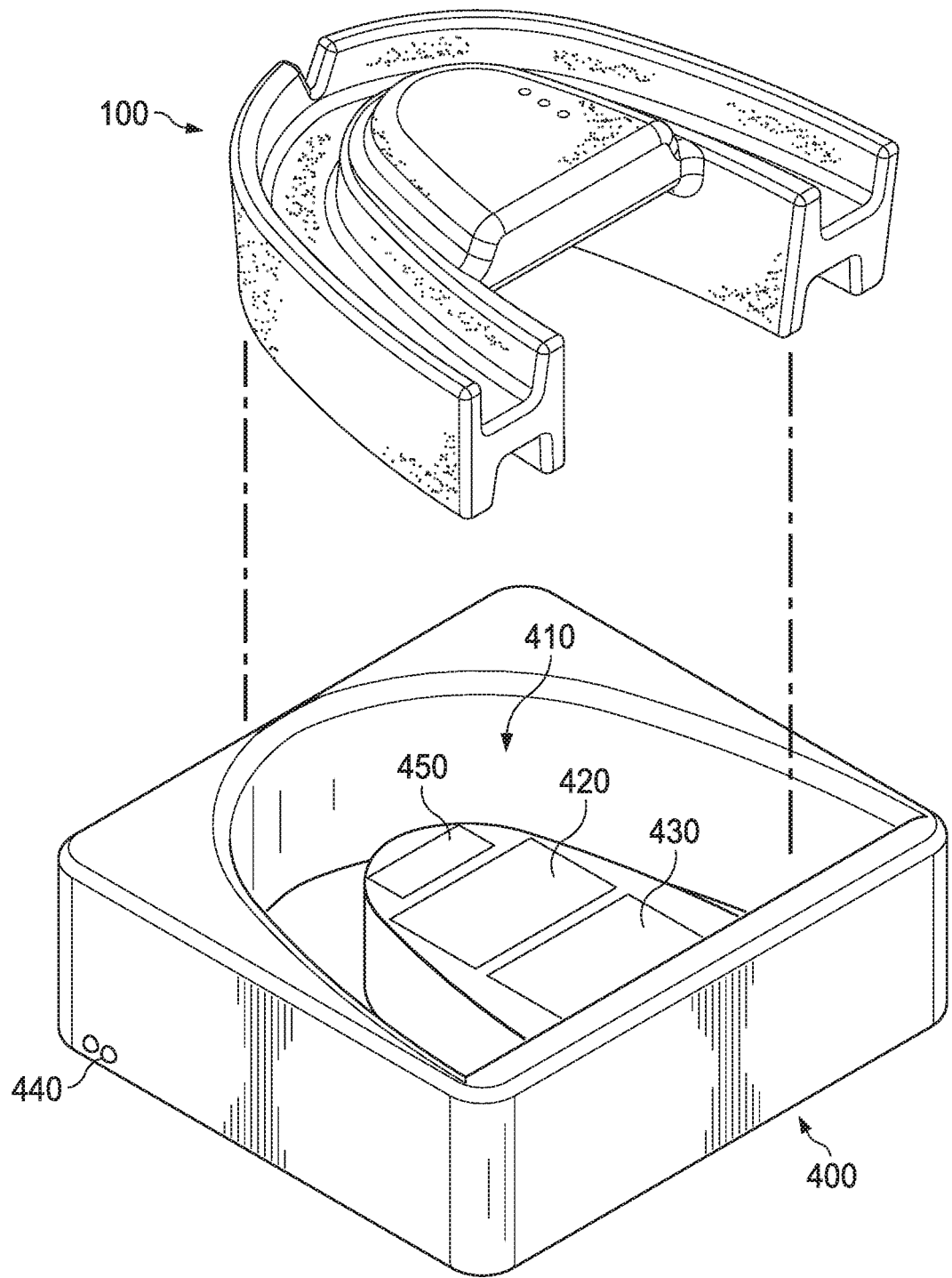
FIG. 4 is a perspective view of a COPA device positioned for docking at a docking station according to embodiments of the present disclosure.
Figure 5:
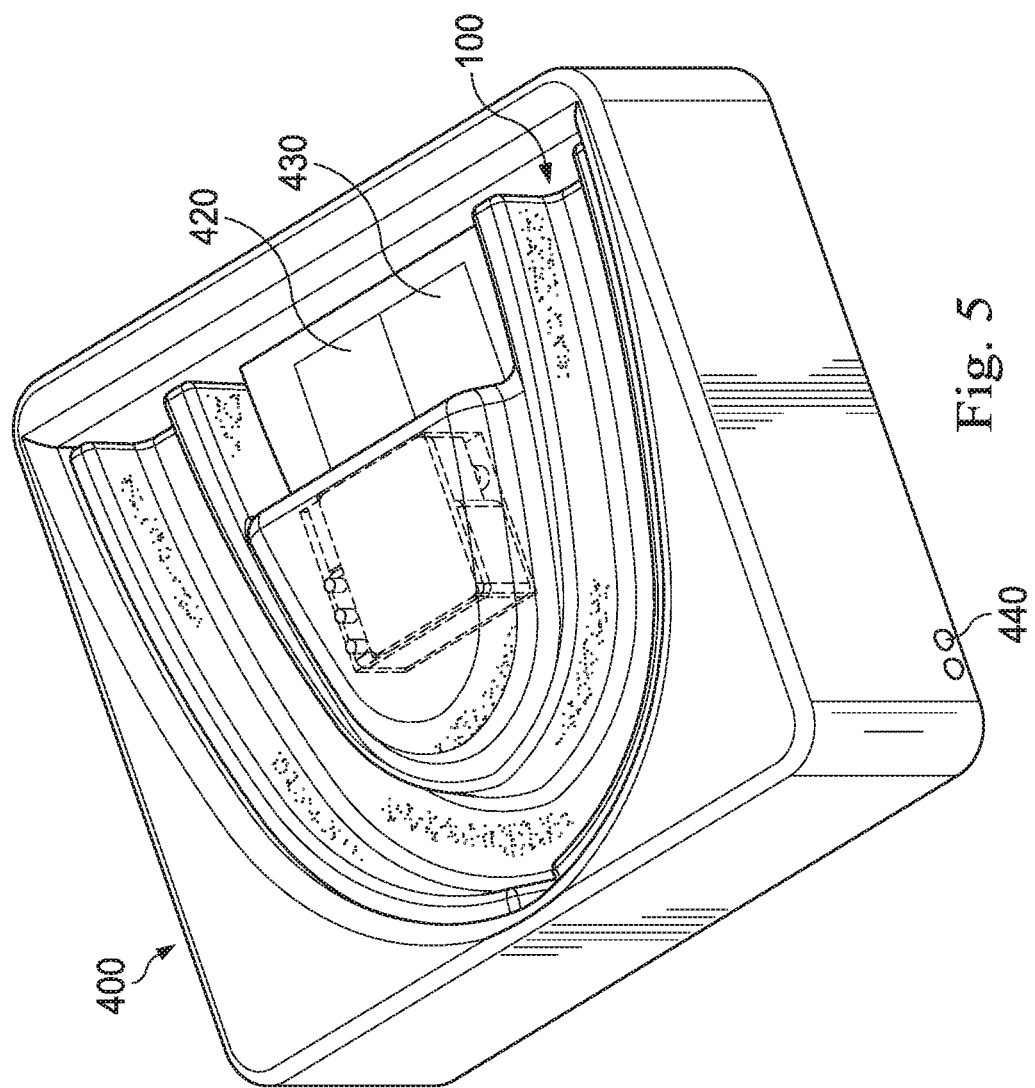
FIG. 5 is a perspective view of a COPA device docked at a docking station according to embodiments of the present disclosure.

FIG. 4 is a perspective view of the COPA device 100 positioned for docking at a docking station 400 according to embodiments of the present disclosure. FIG. 5 is a perspective view of the COPA device 100 docked at the docking station 400 according to embodiments of the present disclosure. The COPA device 100 may be positioned into the docking station 400 for storage, charging, and/or communicating over a communications network. The docking station 400 may include a docking compartment 410, a wireless transceiver 420, a charging component 430, a plurality of indicators 440, and a COPA device sensing component 450. The wireless transceiver 420, the charging component 430, the indicators 440, and the COPA device sensing component 450 may be arranged as shown or in any suitable configuration on the docking station 400.

The docking compartment 410 may be sized and shaped to house the COPA device 100. The wireless transceiver 420 may be configured to transmit and receive data while the COPA device 100 is docked at the docking station 400 via a patient private wireless network, as described in greater detail herein. The charging component 430 may include a haptic charging component (e.g., for charging batteries) and may be configured to charge the COPA device 100 while the COPA device 100 is docked at the docking station 400. For example, the operations of the processor, the actuators, and the releasing of the prescribed substances operate based on electrical power. The COPA device sensing component 450 may be configured to detect whether the COPA device 100 is docked correctly. For example, the bottom side 104 of the COPA device 100 may further include a docking station sensing component, where alignment between the COPA device 100 and the docking station 400 may be detected via the COPA device sensing component 450 and the docking station sensing component. After detecting alignment, the charging component 430 may begin to charge the COPA device 100. In addition, the COPA device 100 may upload prescription administration activities via the wireless transceiver 420 to a COPA management system, as described in greater detail herein. The indicators 440 may include light-emitting diodes (LEDs). The indicators 440 may be configured to indicate whether the COPA device 100 is positioned correctly within the docking compartment 410 for charging and wireless communications. The indicators 440 may be further configured to indicate the charging status (e.g., power on/off) of the COPA device 100 and/or the wireless transmission and/or reception activities of the wireless transceiver 420.

In some embodiments, the docking station 400 provides a closed loop control system that can sense and detect the presence of the COPA device 100 at various stages of use and/or storage and provide corresponding feedback and/or alerts to the user, caregiver, doctor, and/or pharmacy. For example, the indicators 440 may be configured to indicate that the COPA device 100 is within proximity of the docking station 400, properly docked within the docking station 400, improperly docked within the docking station 400, charging, fully charged, transferring data, operating properly, operating improperly, and/or other status indications. In some embodiments, the docking station 400 may include a sound generation component (e.g., a speaker) that can generate various tones and/or vibrations to indicate a current status, including the proximity or docking of the COPA device 100, charging activities, and/or communication activities. In some embodiments, the docking station 400 can be in communication with a computing device such as a smartphone, tablet, or computer (e.g., via a wireless transceiver 420 or via a wired connection) and may send the feedback and/or alerts (as well as logs of prescription administration activities obtained from the COPA device 100) to a COPA smartphone or tablet application.

The COPA device 100 may be placed in the docking station 400 between dosages for storage, charging, and/or communication as needed (e.g., multiple times per day, daily, nightly, weekly, etc.). The charging and/or power needs of the COPA device 100, including the prescription dispensing unit 120, may be minimal since the operations associated with dispensing the medications may typically span short durations (e.g., 1 minute or less). In addition to charging and wireless communications, the docking station 400 may help prevent the COPA device 100 from being lost, misplaced, or damaged. For example, the docking station 400 may further include locking mechanisms to provide additional protocols for matching the COPA device 100 to an intended user. In an embodiment, the docking station 400 may include a thumbprint or optical scanning component configured to unlock or release the COPA device 100 based on a thumbprint verification against the intended user's thumbprint or any other biological markings.

To prevent a successful matching and unlocking of the COPA device 100 by an unintended user for subsequent release of the prescription, the processor within the prescription dispensing unit 120 may be further configured to limit the activation time for the release of the prescription in conjunction with the locking mechanisms. For example, a charged COPA device 100 may be inserted into a patient's mouth for drug delivering or releasing at a designated time. When the administering of the medication is not time-specific, the controlling of the medication release time may begin after an initial use. For example, the processor may be configured to record the time of the initial use and control subsequent releases based on an elapsed time duration or an interval between prescribed dosages. The processor may be configured to release the drug at a designated time or designated time durations for subsequent deliveries.

Figure 6:
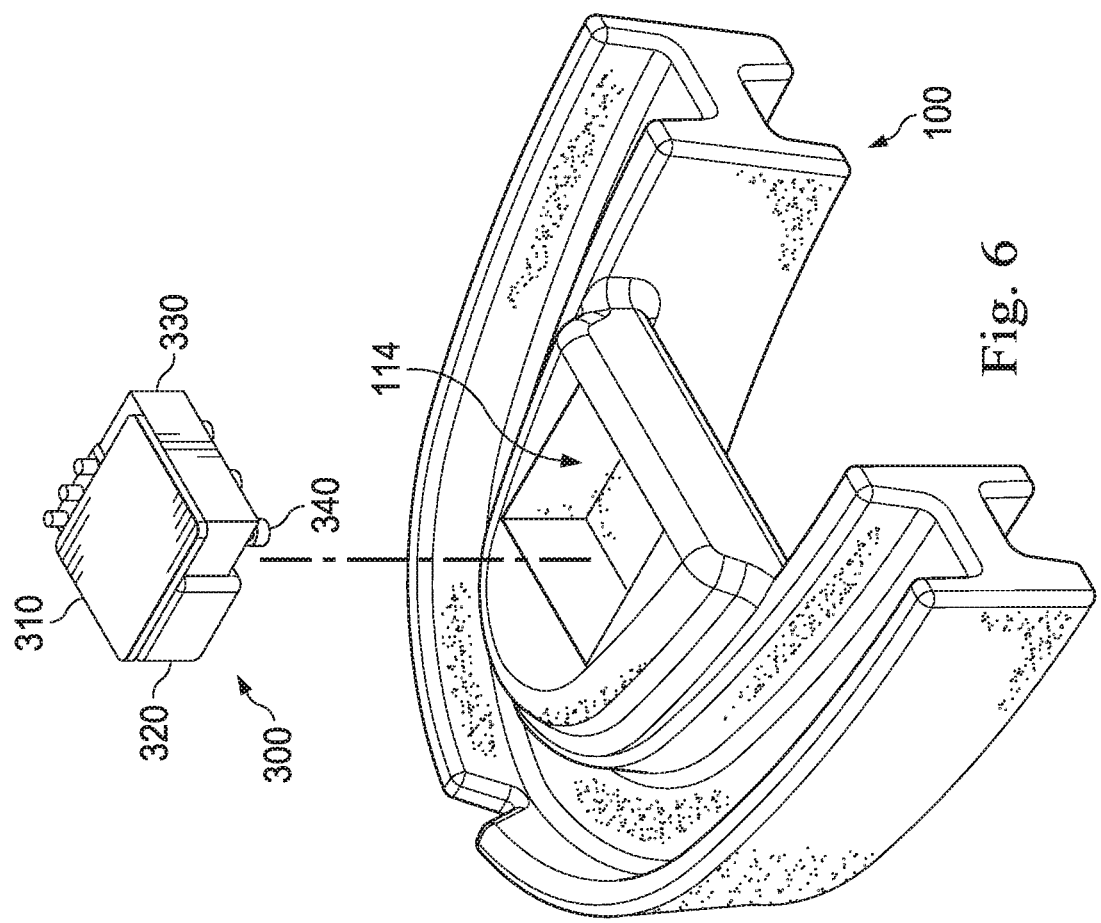
FIG. 6 is a perspective view of a COPA device and a pre-packaged micro-pump unit positioned for coupling according to embodiments of the present disclosure.
Figure 9:
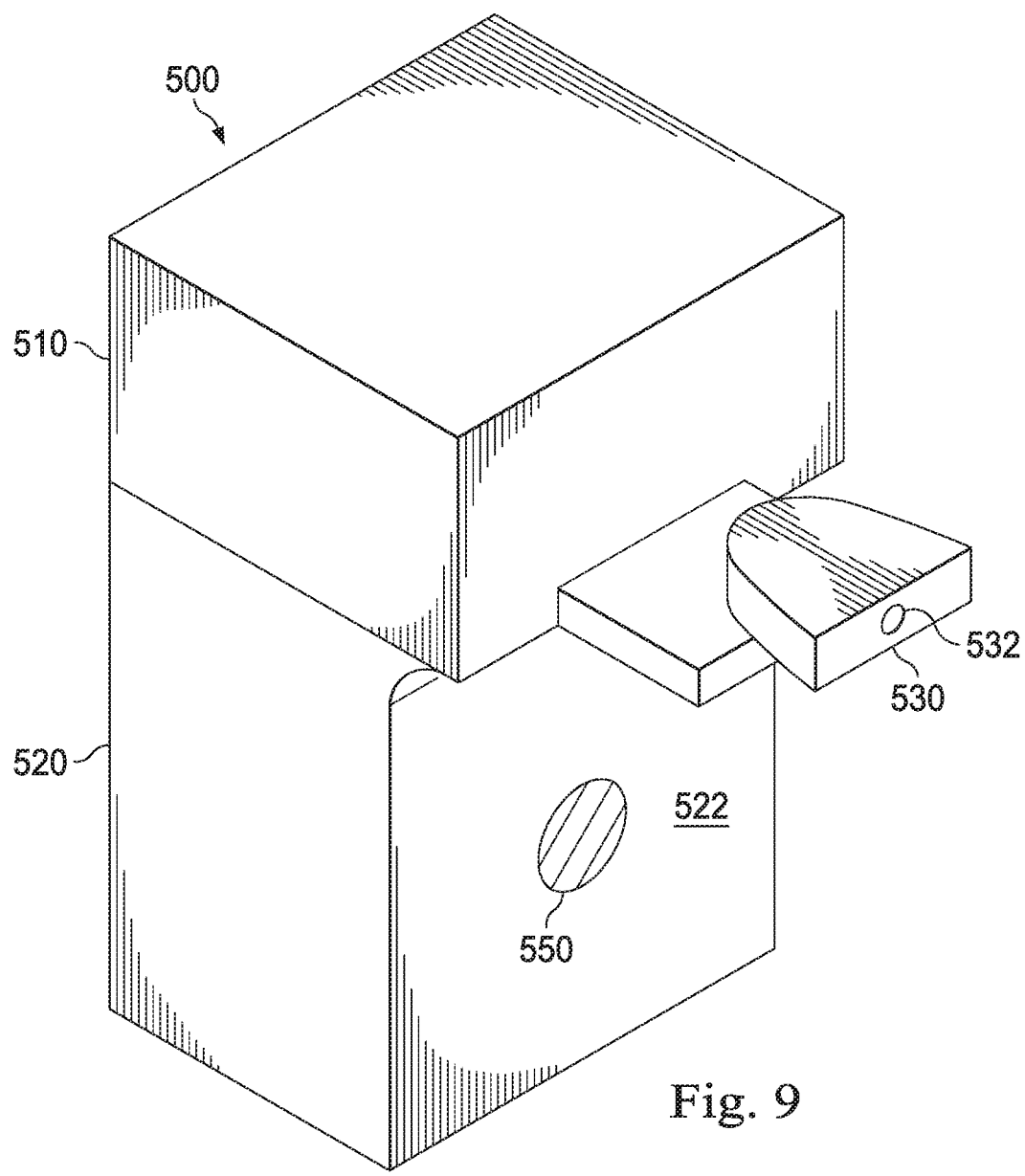
FIG. 9 is a perspective view of a housing according to embodiments of the present disclosure.
Figure 10:
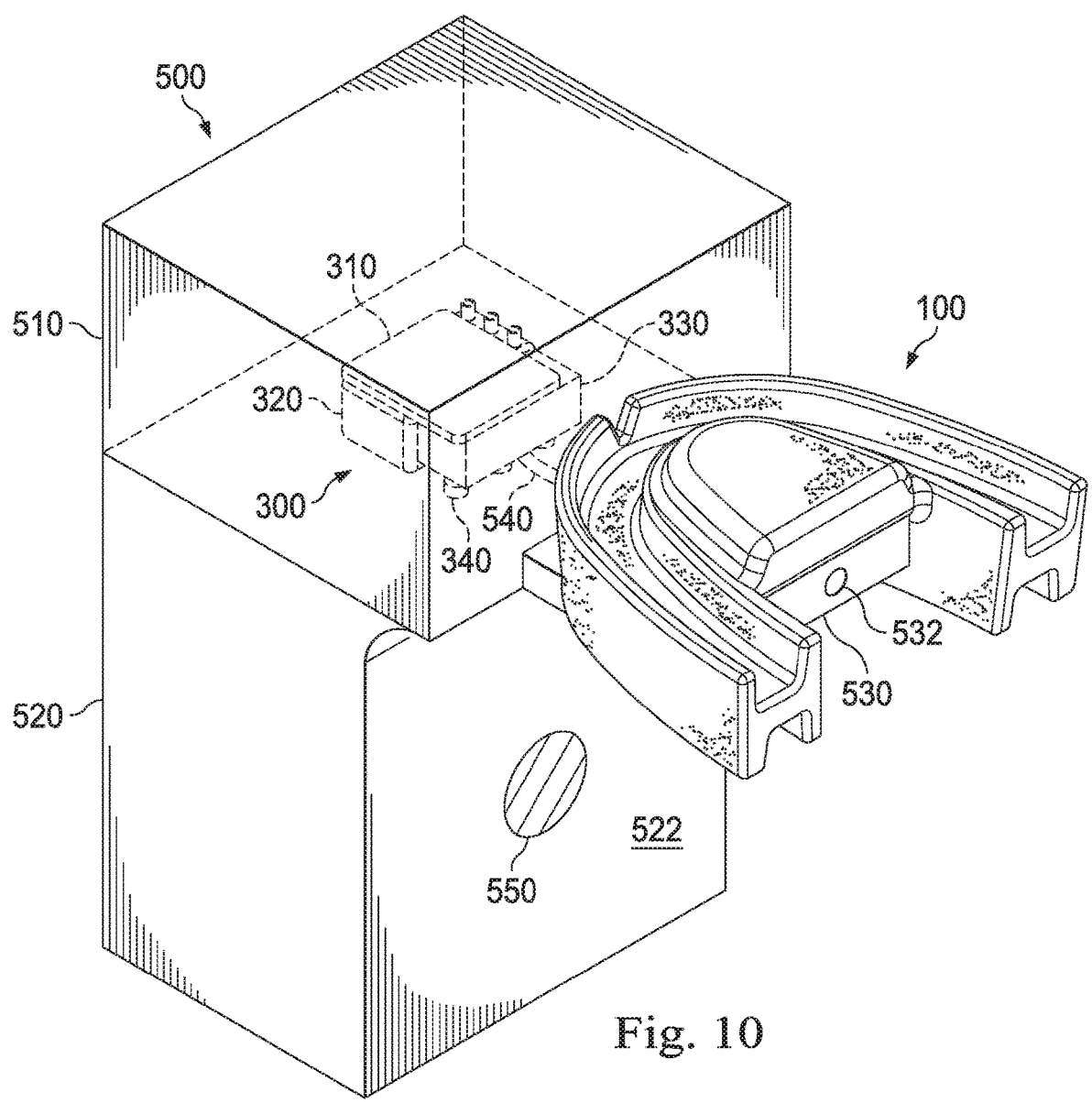
FIG. 10 is a perspective view of a COPA device coupled to a housing and a pre-packaged micro-pump unit positioned within the housing according to embodiments of the present disclosure.

FIG. 6 is a perspective view of the COPA device 100 and the micro-pump unit 300 positioned for coupling according to embodiments of the present disclosure. The micro-pump unit 300 is the core of the prescription dispensing unit 120. The micro-pump unit 300 includes a processor 310, a reservoir 320, an actuator 330, and a plurality of exit valves 340. The processor 310 is configured to control the micro-pump unit 300 and record activities associated with the COPA device 100, for example, dosage delivery time and amount, charged time, and/or wireless communication activities. The reservoir 320 is configured to hold a pre-scribed substance, for example, as formulated for delivery via the micro-pump unit 300. The actuator 330 is configured to push or deliver an exact dosage of the prescribed substance upon activation. The exit valves 340 are positioned at the bottom of the micro-pump unit 300 and are configured to release the prescribed substance for ingestion. More detailed views of the micro-pump unit 300 are shown in FIGS. 9 and 10 and the interactions among the components of the micro-pump unit 300 are described in greater detail below. The micro-pump unit 300 may be pre-packaged with a prescription through various mechanisms, as described in greater detail herein. As shown, the COPA device 100 may include a compartment 114 sized and shaped to receive the micro-pump unit 300. For example, the pre-packaged micro-pump unit 300 may be positioned within the compartment 114 and covered by the sealed sleeve 124 (shown in FIG. 1) to form the sealed prescription dispensing unit 120.

In some embodiments, the processor 310 may be located outside of the micro-pump unit 300. For example, the processor 310 may be removed from the micro-pump unit 300, spaced from the micro-pump unit 300, or coupled to the outside of the micro-pump unit 300. In other embodiments, the processor 310 may be located outside of the COPA device 100 altogether. For example, the processor 310 may be removed from the COPA device 100, spaced from the COPA device 100, or coupled to the outside of the COPA device 100. In exemplary embodiments, the processor 310 may be positioned in a computing device, such as a phone, a tablet, a computer, a server, or any other suitable computing device. In other embodiments, the processor 310 may be located within the micro-pump unit 300. For example, the processor 310 may be coupled to the micro-pump unit 300. In other embodiments, the processor 310 may be coupled to the COPA device 100.

In some embodiments, the processor 310 may communicate with a biometric sensor 550 (FIG. 9) via a wired connection. In other embodiments, the processor 310 may communicate with the biometric sensor 550 via a wireless connection. The processor 310 may receive a signal (e.g., an input) from the biometric sensor 550. The signal/input may be generated based on a physical interaction between the biometric sensor 550 and a biometric attribute of the user (e.g., the user's fingerprint), which will be discussed in greater detail with respect to FIG. 9.

In some embodiments, the processor 310 may communicate with an environmental sensor 560 (FIG. 12) via a wired connection. In other embodiments, the processor 310 may communicate with the environmental sensor 560 via a wireless connection. The processor 310 may receive a signal (e.g., an input) from the environmental sensor 560. The signal/input may be generated based on environmental attributes (e.g., temperature), which will be discussed in greater detail with respect to FIG. 12.

In some embodiments, the processor 310 may communicate with a top side capacitive sensor array 716 (FIG. 18) and/or a bottom side capacitive sensor array 718 (FIG. 19) via a wired connection. In other embodiments, the processor 310 may communicate with the top side capacitive sensor array 716 and/or the bottom side capacitive sensor array 718 via a wireless connection. The processor 310 may receive a signal (e.g., an input) from the top side capacitive sensor array 716 and/or the bottom side capacitive sensor array 718. The signal/input may be generated based on deformation of the top side 102 and/or the bottom side 104 of the COPA device 100 (which will be discussed in greater detail with respect to FIGS. 23 and 24).

In some embodiments, the actuator 330 may be located outside of the micro-pump unit 300. For example, the actuator 330 may be removed from the micro-pump unit 300, spaced from the micro-pump unit 300, or coupled to the outside of the micro-pump unit 300. In other embodiments, the actuator 330 may be located outside of the COPA device 100 altogether. For example, the actuator 330 may be removed from the COPA device 100, spaced from the COPA device 100, or coupled to the outside of the COPA device 100. In other embodiments, the actuator 330 may be located within the micro-pump unit 300. For example, the actuator 330 may be coupled to the micro-pump unit 300. In other embodiments, the actuator 330 may be coupled to the COPA device 100.

In some embodiments, the reservoir 320 may be located outside of the micro-pump unit 300. For example, the reservoir 320 may be removed from the micro-pump unit 300, spaced from the micro-pump unit 300, or coupled to the outside of the micro-pump unit 300. In other embodiments, the reservoir 320 may be located outside of the COPA device 100 altogether. For example, the reservoir 320 may be removed from the COPA device 100, spaced from the COPA device 100, or coupled to the outside of the COPA device 100. In other embodiments, the reservoir 320 may be located within the micro-pump unit 300. For example, the reservoir 320 may be coupled to the micro-pump unit 300. In other embodiments, the reservoir 320 may be coupled to the COPA device 100. In some embodiments, the reservoir 320 may be a pharmaceutical medication bottle. For example, the reservoir 320 may be a prescription pill bottle, a liquid pain medication bottle, or any other suitable container (which may be commercially available) to hold prescribed or over-the-counter medications.

Figure 7:
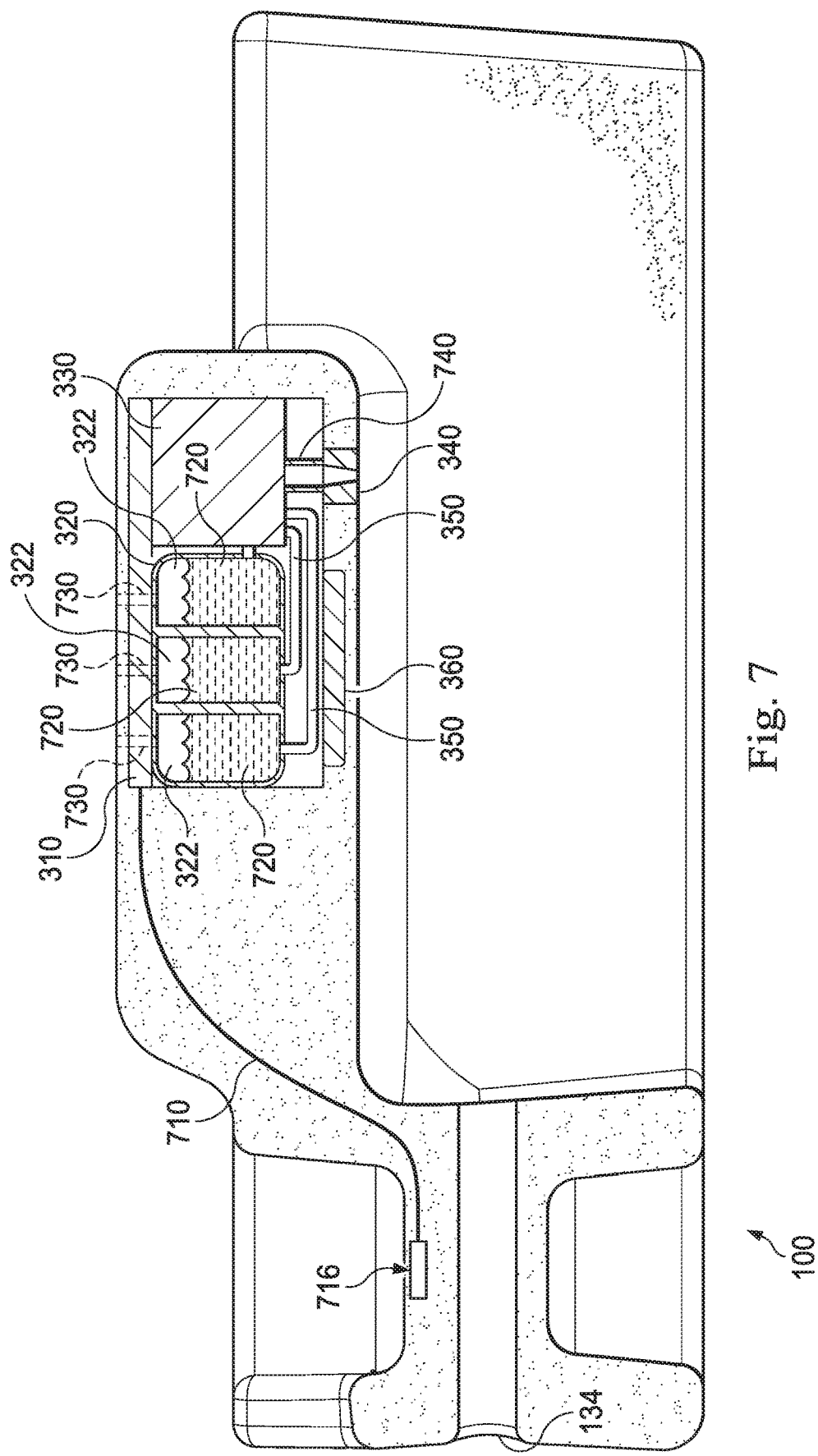
FIG. 7 is a cross-sectional view of a COPA device along section line 7-7 in FIG. 1 according to embodiments of the present disclosure.

FIG. 7 provides a detailed view of the internal components of the micro-pump unit 300 and the interactions among the internal components according to embodiments of the present disclosure. In this regard, FIG. 7 is a cross-sectional view of the COPA device 100 according to embodiments of the present disclosure. The cross-sectional view is taken along section line 7-7 of FIG. 1. The micro-pump unit is positioned within the compartment 114 (shown in FIG. 6) of the COPA device 100. The micro-pump unit 300 may further include a charging component 360 (e.g., batteries) and a memory 370 (shown in FIG. 8). The charging component 360 may be in communication with the processor 310 and the actuator 330. When the COPA device 100 is docked at the docking station 400 as shown in FIG. 5, the charging component 360 may be coupled to the charging component 430 of the docking station 400 and configured to charge the COPA device 100 (e.g., the processor 310 and the actuator 330) via battery charging or wireless charging. The memory 370 may include volatile memory and non-volatile memory of any suitable memory types, including random access memory (RAM), read-only memory (ROM), programmable read-only memory (PROM), erasable programmable read-only memory (EPROM), electrically erasable programmable read-only memory (EEPROM), dynamic random-access memory (DRAM), static random-access memory (SRAM), and combinations thereof. In some embodiments, the memory 370 may be coupled to the micro-pump unit 300. In some embodiments, the memory 370 may be disposed within the substance dispensing apparatus (e.g., the COPA device 100). The access opening 134 (FIG. 1) may extend through the COPA device 100, from an exterior face to an interior face, terminating at an outlet opening that may be within the user's mouth, in some embodiments. In some embodiments, the outlet opening may be within the user's mouth when the COPA device 100 is within the user's mouth. In other embodiments, the outlet opening may be outside of the user's mouth, such as when the COPA device 100 is outside of the user's mouth. The walls of the access opening 134 may define a hollow cavity, and the access opening 134 may be a cylinder, a rectangular prism, or any other suitable shape.

The processor 310 can be in communication with the top side capacitive sensor array 716 and/or the bottom side capacitive sensor array 718, for example, via the wire 710, and the actuator 330. While only the top side capacitive sensor array 716 and the wire 710 is illustrated in FIG. 7, it is understood that the processor 310 can be in communication with the bottom side capacitive sensor array 718 via one or more wires (e.g., the wire 710 and/or other wires). The actuator 330 can be in communication with the reservoir 320 and the exit valves 340 via flow channels 350. The reservoir 320 can be in communication with the access ports 122 (shown in FIG. 1) and the flow channels 350.

The reservoir 320 may include one or more chambers 322, for example, one, two, three, four, five, six, or any suitable number of chambers 322. The chambers 322 may be configured to hold a prescribed substance 720. In this regard, the number and size of the chambers 322 can be selected based on the number of prescribed substances, type(s) of prescribed substances, and/or dosage amounts to be used. The chambers 322 can be any size that will still allow the device to be positioned within the mouth of a patient. In some instances, the chambers 322 are in communication with corresponding chambers or channels formed in the COPA device 100 to allow an increased volume of storage for the prescribed substance(s). The chambers 322 may be in communication with the access ports 122. In some embodiments, each chamber 322 is in communication with one of the access ports 122 through access cannulas 730.

A clinician or a pharmacy technician may fill or refill the prescribed substance 720 via the access ports 122. The prescribed substance 720 may include liquid formulations, powder formulations, multiparticulate formulations, or any other suitable formulations. In some embodiments, all chambers 322 are filled with liquid formulations. In some other embodiments, one chamber 322 may be filled with a liquid formulation and another chamber 322 may be filled with a powder or multiparticulate formulation. The prescribed substance 720 in the different chambers 322 may be released at the same time to form a particular formulation or at different times to prevent certain active ingredients in the prescribed substances 720 from reacting with each other. In this regard, each chamber 322 may contain a different prescribed substance for the intended user.

The actuator 330 may be a micro-pump suitable for delivery of pharmaceutical formulations. The actuator 330 may be activated or triggered by the processor 310 to cause the prescribed substances 720 to flow through the flow channels 350 and exit cannulas 740 and release via the exit valves 340. The actuator 330 may be activated one or more times to release an exact dosage of the prescribed substances 720. The flow channels 350 may be constructed from suitable tubing materials. The exit valves 340 may be any suitable flow control valves, for example, with elastomeric membranes, configured to prevent leakage of the prescribed substances 720 into the user's mouth or backflow of the prescribed substance 720 from the user's mouth into the COPA device 100.

The processor 310 may be any suitable microcontroller or microprocessor configured to perform the functions described herein, including functions such as performing patient identification and verification, performing capacitance sensing (e.g., in conjunction with the top side and/or bottom side capacitive sensor arrays), instructing the actuator 330 to release a dose of the prescribed substance 720, controlling the opening of the exit valves 340, controlling operation of components of the micro-pump unit 300 in accordance with dosage instructions for an intended user, storing dispensing data, etc. The dosage instructions may include at least a dosage amount and timing for dispensing the substance to the intended user. The dosage instructions may be stored in the memory 370.

Figure 8:
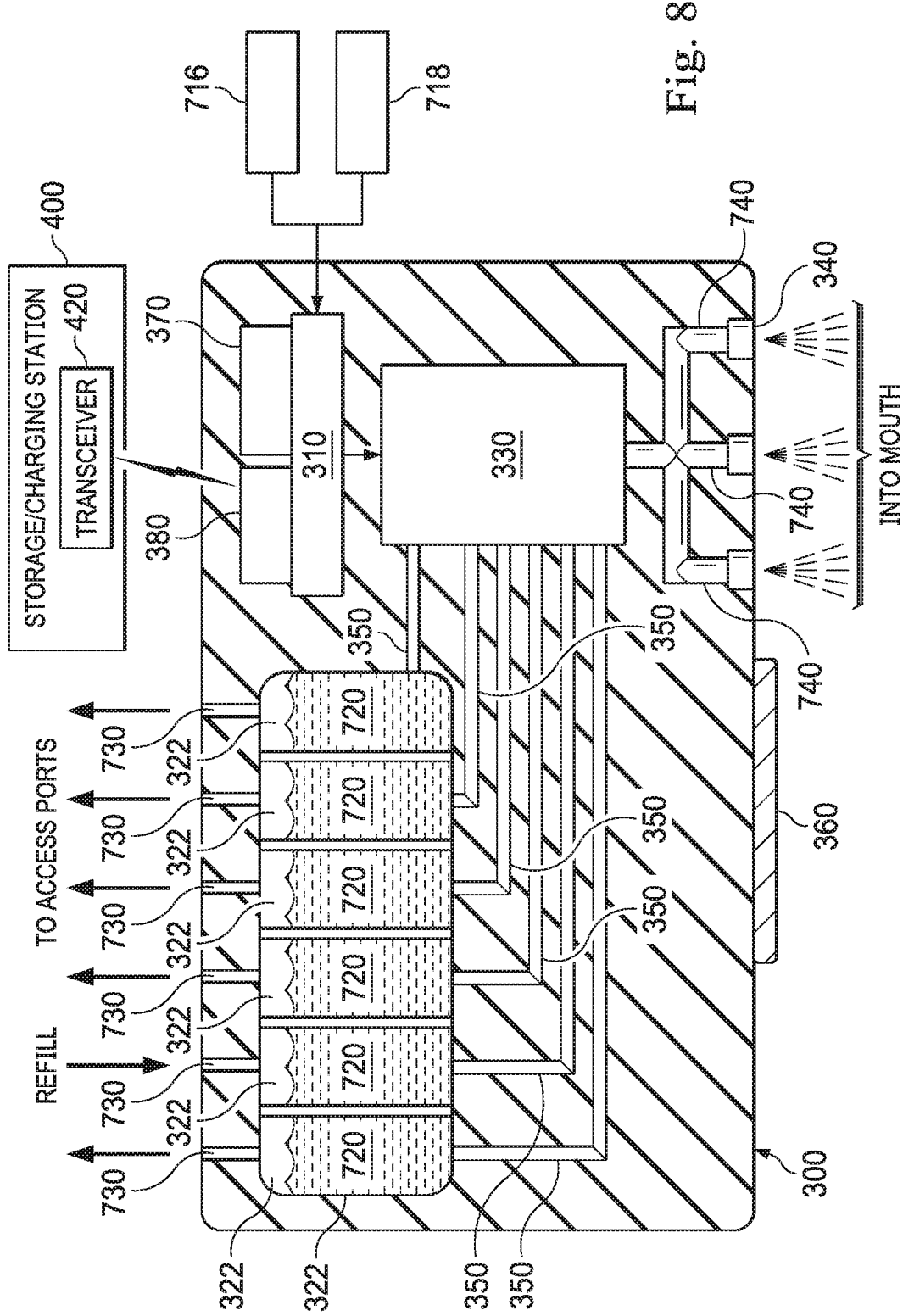
FIG. 8 is a schematic diagram of a micro-pump unit according to embodiments of the present disclosure.

FIG. 8 is a schematic diagram of the micro-pump unit 300 according to embodiments of the present disclosure. FIG. 8 provides a more detailed view of the micro-pump unit 300 and interactions with the top side and bottom side capacitive sensor arrays 716, 718 and the docking station 400. As shown, the micro-pump unit 300 may further include a wireless transceiver 380. The wireless transceiver 380 may implement any suitable wireless communication protocols. The wireless transceiver 380 may wirelessly communicate with the docking station 400, for example, to upload recorded activities or to download revised or new dosage instructions, as described in greater detail herein. Further, the wireless transceiver 380 may wirelessly communicate with other wireless communication devices, including a communication device (e.g., a computer, tablet, smartphone, etc.) of the intended user. In this regard, the processor of the micro-pump unit 300 can be configured to initiate alerts or reminders to the user (e.g., based on a dosage timing of the dosage instructions) by triggering the intended user's communication device to issue such an alert or reminder (e.g., by activating an audible and/or visual indicator). Similarly, the processor of the micro-pump unit 300 and/or the docking station 400 can be configured to initiate alerts or reminders through communications with a communication device of a medical provider. For example, the micro-pump unit 300 and/or the docking station may alert the medical provider based on a failure to dispense the substance in accordance with the dosage instructions (e.g., the patient is not taking the medication as prescribed) and/or multiple failed attempts to authenticate the intended user (e.g., indicating that someone other than the intended user is attempting to access the medication or that the intended user is having difficulties using the device).

FIG. 9 provides a perspective view of the housing 500 according to embodiments of the present disclosure. The housing 500 may include an upper portion 510 and a lower portion 520. The housing 500 may be sized and shaped for handheld use. For example, the housing 500 may be structurally arranged to be gripped by a single hand of a user by placing the user's fingers and palm around the housing 500. The housing 500 may be any suitable shape such as a cylinder, a rectangular prism, a cube, or any combination thereof. In some instances, the housing 500 may be formed of multiple walls. The housing 500 may include an inside cavity for receiving one or more components, such as a medication bottle 590, a cap 592, a dip tube 594, a valve 596, a pump 598, a tubular connector 580, the tubular member 540, and/or any other suitable components. The inside cavity may be defined by the walls of the housing 500. In some embodiments, the housing 500 can be contoured to have corresponding areas (e.g., depressions and/or raised portions) for the user's fingers. For example, the housing 500 can be contoured to have a grip disposed on all or a portion of the housing 500. An exterior surface of the housing 500 can include surface roughening features and/or surface texturing features, such as texturing, knurling, taping, etc. The housing 500 can be made of any suitable material such as a polymer, plastic, metal, metal alloy, etc. For example, the material of the housing 500 and/or the exterior surface of the housing 500 may be structurally arranged to facilitate easy gripping by a user, including patients with diminished hand strength, such as elderly patients.

In some embodiments, the housing 500 includes a biometric sensor 550. The biometric sensor 550 may be a fingerprint scanner, an optical scanner (e.g., a retina scanner, a cornea scanner, an iris recognition scanner, etc.), a DNA scanner (e.g., a saliva scanner, a perspiration scanner, a sebum (i.e., skin oil) scanner), a camera for detecting facial features (e.g., feature size, feature geometry, feature spacing, vein spacing, etc.), a voice print scanner, an auditory scanner, an olfactory scanner, a vibration scanner configured to detect a walking and/or running gait of the user, and/or a scanner enabled to recognize any other suitable biological marker. The biometric sensor 550 can include a camera, electromagnetic sensor, and/or optical sensor device for detecting electromagnetic radiation including visible, infrared, and/or ultraviolet light, for example. The electromagnetic sensor may sense reflected, refracted, or detected waves (e.g., visible light waves, infrared waves, ultraviolet waves, etc.) and may be used to detect one or more features, such as anatomical features, of the user. In some instances, the housing 500 can include one or more sources of electromagnetic radiation, such as an illumination source, to provide visible, infrared, and/or ultraviolet light, for example. In some examples, the biometric sensor 550 may be a signature verification device, such as an optical scanner, a camera, a digital scanner (e.g., a capacitive touch screen, a resistive touch screen, etc.), and/or any combination thereof. The signature verification device may scan an image of the user's signature using, for example, the optical scanner and/or the camera. In other instances, the signature verification device may obtain the user's signature in real-time using, for example, the digital scanner. The housing 500 may include one biometric sensor 550 or multiple biometric sensors, including the different types of biometric sensors described above.

In an exemplary embodiment, the biometric sensor 550 may be a fingerprint scanner that uses an optical sensor or an ultrasonic sensor. The biometric sensor 550 may be sized and shaped to match with the dimensions of a plurality of the user's fingers, or the biometric sensor 550 may be sized and shaped to match with the dimensions of only one of the user's fingers. For example, the biometric sensor 550 may be sized and shaped to match with the dimensions of the user's right thumb, right index finger, right middle finger, right ring finger, right pinky finger, and/or the corresponding fingers on the user's left hand, respectively. In some instances, the biometric sensor 550 may be a substantially circular shape. In other instances, the biometric sensor 550 may be a substantially elliptical shape. The biometric sensor 550 may be any other suitable shape. In some embodiments, the biometric sensor 550 may be sized and shaped so that the entire fingerprint of the user fits within an outside border of the biometric sensor 550. In other embodiments, the biometric sensor 550 may be sized and shaped so that only a portion of the user's fingerprint fits within the outside border of the biometric sensor 550.

The biometric sensor 550 may be located on the housing 500 in such a way that is ergonomic for the user. In an exemplary embodiment, the intended user holds the housing 500 while the COPA device 100 is in the intended user's mouth because the COPA device 100 is coupled to the housing 500 (see FIG. 10). Therefore, in such embodiments, it is beneficial to the user to have the biometric sensor 550 located in an ergonomic position when the user is holding the housing 500 so as to reduce strain on the user's hand, wrist, and/or arm.

In the embodiment in FIG. 9, the biometric sensor 550 is located on the lower portion 520 of the housing 500. In other embodiments, the biometric sensor 550 may be located on the upper portion 510 of the housing 500. Additionally, in the embodiment in FIG. 9, the biometric sensor 550 is located on a front face 522 of a front wall 524 the lower portion 520 of the housing 500. For example, the biometric sensor 550 may be coupled to the front wall 524, positioned on the surface of the front wall 524, or positioned partially or fully within the front wall 524. The front wall 524 may be coupled to the bottom wall 570 (FIG. 15) of the housing. The front face 522 of the housing 500 may be a surface that faces the user when the user grips and holds the housing 500 in his or her hand. This arrangement may advantageously permit the biometric sensor 550 to detect the user's thumb when the user's hand is positioned around the housing 500. In other embodiments, the biometric sensor 550 may be located on any other face of the lower portion 520 or any face of the upper portion 510 of the housing 500. For example, the biometric sensor 550 may be located on a back face of the lower portion 520 of the housing 500. This arrangement may advantageously permit the biometric sensor 550 to detect the user's index finger when the user's hand is positioned around the housing 500. In other instances, this arrangement may also permit the biometric sensor 550 to detect the user's middle finger, ring finger, and/or pinky finger when the user's hand is positioned around the housing 500. In other embodiments, the biometric sensor 550 is not located on the housing 500 at all. For example, the biometric sensor 550 may be removed from the housing 500 or spaced from the housing 500. As an additional example, the biometric sensor 550 may be located on a phone, tablet, or computer.

In some embodiments, the intended user may place the intended user's fingerprint on the biometric sensor 550. The biometric sensor 550 then detects a fingerprint model of the intended user's scanned fingerprint. The detected fingerprint model is unique to the intended user. In other embodiments, the biometric sensor 550 may detect multiple fingerprint models based on multiple inputs. For example, the intended user may place the intended user's fingerprint on the biometric sensor 550 in different orientations, directions, and/or locations. As an example, the intended user may place between 50% and 75% of the intended user's fingerprint on the biometric sensor 550. The above range of percentages is listed for exemplary purposes only. Percentages of less than 50% of the intended user's fingerprint and greater than 75% of the intended user's fingerprint are also contemplated by the present disclosure. The biometric sensor 550 may detect multiple fingerprint models based on the multiple inputs discussed above in order to define a range of acceptable fingerprint model matches associated with the intended user. This may require the user to place the user's fingerprint on the biometric sensor 550 multiple times in order for the biometric sensor 550 to detect multiple fingerprint models.

In some embodiments, the user may be required to keep the user's finger on the biometric sensor 550 for the duration of the dosage dispensing cycle. In other embodiments, the user may be able to remove the user's finger from the biometric sensor 550 after the biometric sensor 550 detects the user's fingerprint model and before the end of the dosage dispensing cycle.

In some embodiments, the processor 310 receives, from the biometric sensor 550, an input associated with the respective biometric attributes detected by the biometric sensor 550. The received input may be an electrical signal representative of the detected biometric attribute(s). Based on the input received by the processor 310, the processor 310 may determine whether the current detected biometric attribute matches a stored biometric attribute of the intended user. Upon detecting a matching biometric attribute, the processor 310 may continue the dosage dispensing process, as described in greater detail herein.

FIG. 10 provides a perspective view of the COPA device 100 coupled to a housing 500. In some embodiments, the COPA device 100 is coupled to the housing 500 via a docking port 530. The housing 500 may include an upper portion 510 and a lower portion 520. In FIG. 10, the micro-pump unit 300 is positioned within the upper portion 510 of the housing 500. The reservoir 320 of the micro-pump unit 300 may be connected to the COPA device 100 via a tubular member 540, which may be a hose structure in some embodiments. The tubular member 540 may be a flexible material, or the tubular member 540 may be rigid. When the actuator 330 is activated, the actuator 330 delivers an exact dosage of the prescribed substance (e.g., the prescribed substance 720) from the reservoir 320 to the intended user's mouth via the tubular member 540. The tubular member 540 may extend through the docking port 530, terminating at the exit port 532 within the intended user's mouth, to enable the prescribed substance to be delivered directly into the intended user's mouth for ingestion. In some embodiments, the COPA device 100 may include an access opening 134 (FIGS. 1 and 7). The tubular member 540 may enter the docking port 530 via the access opening 134 of the COPA device 100. In some embodiments, the micro-pump unit 300 may be positioned within the lower portion 520 of the housing 500.

Figure 14:
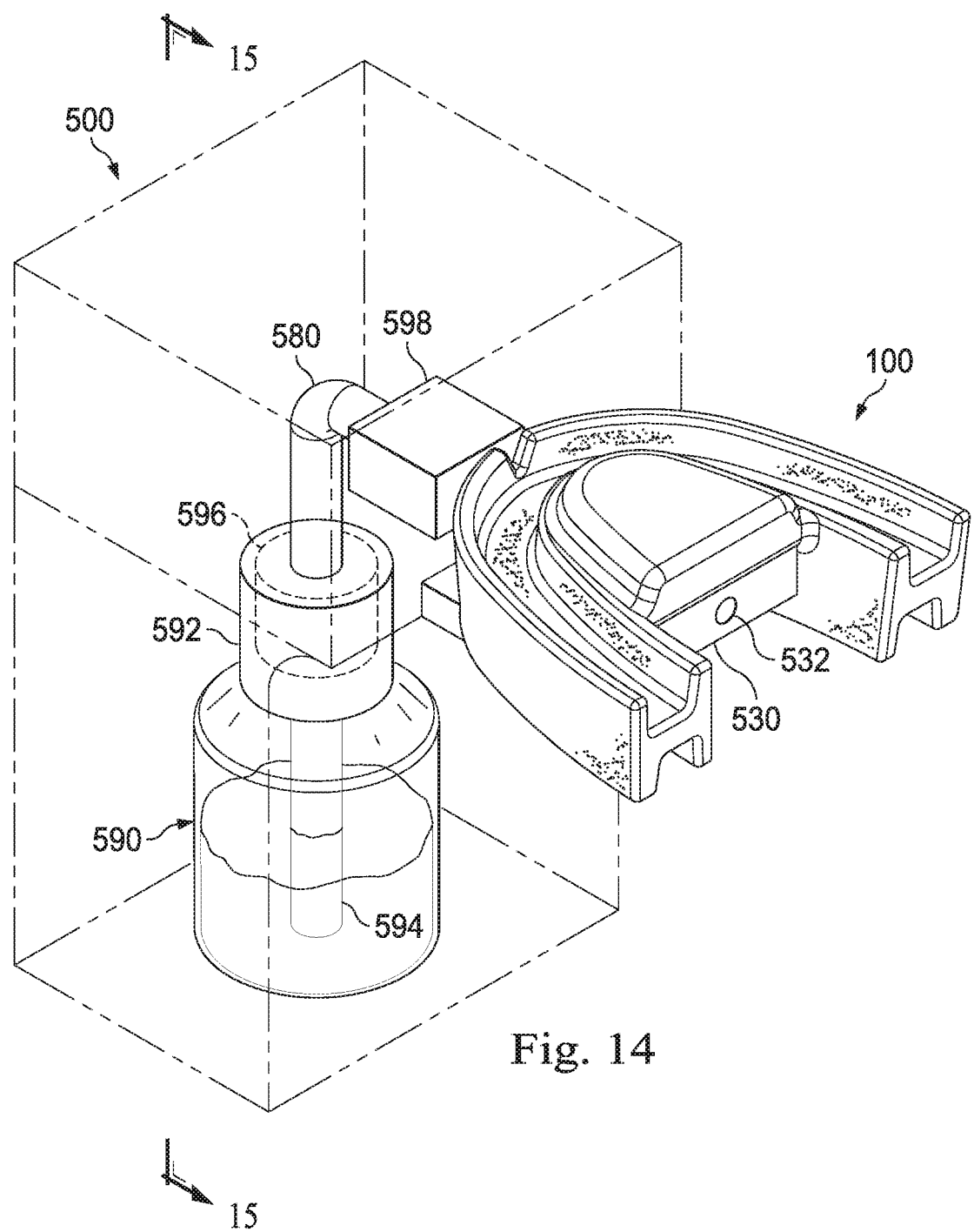
FIG. 14 is a perspective view of an interior of a housing according to embodiments of the present disclosure.

In some embodiments, the housing 500 is sized and shaped to allow a commercial prescription medication bottle to fit within the housing 500 (e.g., medication bottle 590 in FIG. 14). In these embodiments, the prescription medication bottle may constitute a reservoir (e.g., the reservoir 320) for the prescribed substance (e.g., a liquid, pills, etc.). The prescribed substance (e.g., the prescribed substance 720) may be delivered directly into the intended user's mouth via a transportation channel (e.g., tubular member 540). Similar to the micro-pump unit 300, upon activation, the actuator 330 may deliver an exact dosage of the prescribed substance to the intended user from the prescription medication bottle. The actuator 330 may be activated by the processor 310 in response to an indication that the COPA device 100 is within the intended user's mouth, the indication being determined by one or more processes described herein. In other embodiments, an actuator within the housing 500 (e.g., a different actuator than the actuator 330) may deliver an exact dosage of the prescribed substance to the intended user from the prescription medication bottle.

Figure 11:
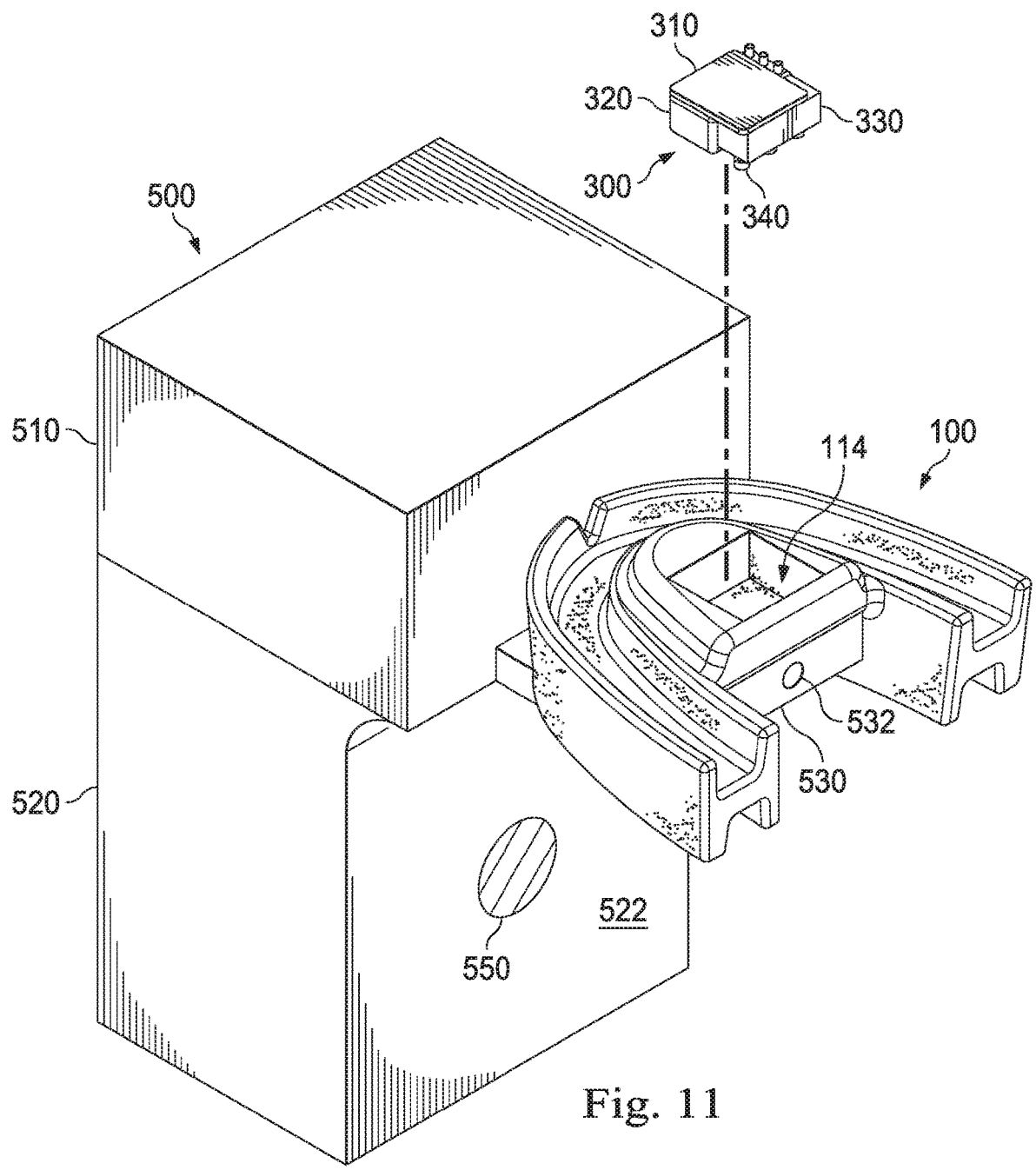
FIG. 11 is a perspective view of a COPA device coupled to a housing and a pre-packaged micro-pump unit positioned for coupling within the COPA device according to embodiments of the present disclosure.

FIG. 11 provides a perspective view of the COPA device 100 coupled to the housing 500. In the embodiment in FIG. 11, the micro-pump unit 300 is arranged to be positioned within the compartment 114 in the COPA device 100. During use, the micro-pump unit 300 is positioned within the COPA device 100. In some embodiments, the housing 500 may include a thumbprint or optical scanning component (e.g., biometric sensor 550, which is discussed above with respect to FIG. 9) to verify that the intended user is attempting to obtain a prescribed substance (e.g., the prescribed substance 720). Upon verification of the intended user, the actuator 330 may be activated. In other embodiments, the actuator 330 is activated by the processor 310 after the processor 310 determines, based on an input received from the top side capacitive sensor array 716 (FIG. 18) and/or the bottom side capacitive sensor array 718 (FIG. 19), that the COPA device 100 is within the intended user's mouth.

Similar to the discussion above with respect to FIG. 10, in some embodiments, the housing 500 is shaped to allow a commercial prescription medication bottle (e.g., the medication bottle 590 in FIG. 14) to fit within the housing 500. In this embodiment, the prescription medication bottle may constitute a reservoir (e.g., the reservoir 320) for the prescribed substance (e.g., a liquid, pills, etc.). The prescribed substance (e.g., the prescribed substance 720) may be delivered directly into the intended user's mouth via a transportation channel. Similar to the micro-pump unit 300, upon activation, the actuator 330 may deliver an exact dosage of the prescribed substance to the intended user from the prescription medication bottle. The actuator 330 may be activated by the processor 310 in response to an indication that the COPA device 100 is within the intended user's mouth, the indication being determined by one or more processes described herein. In other embodiments, an actuator within the housing 500 (e.g., a different actuator than the actuator 330) may deliver an exact dosage of the prescribed substance to the intended user from the prescription medication bottle.

Figure 12:
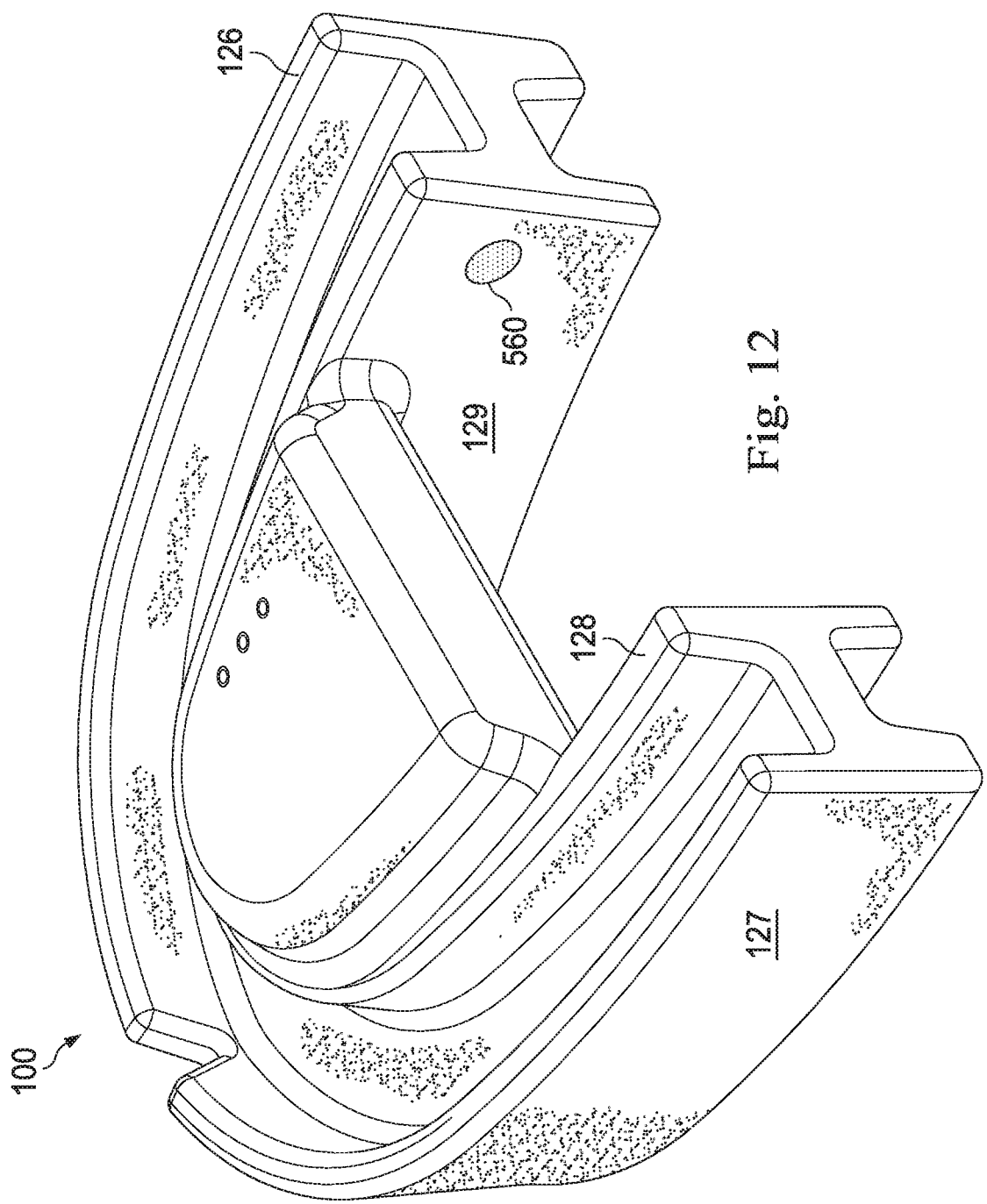
FIG. 12 is a perspective view of a COPA device according to embodiments of the present disclosure.

FIG. 12 provides a perspective view of the COPA device 100 including an environmental sensor 560 according to embodiments of the present disclosure. In some embodiments, the environmental sensor 560 is coupled to and/or integrated in the COPA device 100. For example, the environmental sensor 560 may be coupled to a wall of the COPA device 100, positioned on the surface of the wall of the COPA device 100, or positioned partially or fully within the wall of the COPA device 100. In some embodiments, the environmental sensor 560 is coupled to the back wall portion 128 or the front wall portion 126 of the COPA device 100. In other embodiments, the environmental sensor 560 may be coupled to an outer face 129 of the back wall portion 128, or the environmental sensor 560 may be positioned partially or fully within the back wall portion 128. In further embodiments, the environmental sensor 560 may be coupled to an outer face 127 of the front wall portion 126, or the environmental sensor 560 may be positioned partially or fully within the front wall portion 126.

The COPA device 100 may include one environmental sensor (e.g., the environmental sensor 560), or the COPA device 100 may include multiple environmental sensors, with one of the environmental sensors being the environmental sensor 560. All of the multiple environmental sensors may be duplicates of the environmental sensor 560. The multiple environmental sensors can be configured to detect different environmental attributes.

In some embodiments, the environmental sensor 560 may be configured to detect one or more environmental attributes such as temperature, humidity, carbon dioxide ($CO_2$), volatile organic compounds (VOCs), barometric pressure, the presence of saliva, and/or any other suitable environmental attribute. In other embodiments, the environmental sensor 560 may be configured to detect DNA (e.g., saliva) of the user. In some embodiments, the processor 310 receives, from the environmental sensor 560, an input associated with the respective environmental attributes detected by the environmental sensor 560. The received input may be an electrical signal representative of the detected environmental attribute(s). Based on the input received by the processor 310, the processor 310 may determine whether the COPA device 100 is positioned within the user's mouth.

In an exemplary embodiment, the environmental sensor 560 may detect the ambient temperature of the air surrounding the environmental sensor 560. Thus, when the COPA device 100 is placed within the user's mouth, the environmental sensor 560 detects the temperature of the air inside the user's mouth. The processor 310 may then receive the temperature value(s) detected by the environmental sensor 560. The processor 310 may receive the temperature value(s) by a wireless and/or a wired connection. In an exemplary embodiment, the processor 310 includes a stored, pre-defined range of temperature values, which may be stored in the memory 370 (FIG. 7). When the processor 310 receives a temperature value from the environmental sensor 560 that is within the pre-defined range of temperature values, the processor 310 may determine that the environmental sensor 560, and, therefore, the COPA device 100, is positioned within the user's mouth. The temperature values in the pre-defined range of temperature values may include values from 97 degrees Fahrenheit (° F.) to 99° F. The above range of temperatures is listed for exemplary purposes only. Temperatures of less than 97° F. and greater than 99° F. are also contemplated by the present disclosure.

While the embodiment in FIG. 12 depicts the environmental sensor 560 as one sensor, in some embodiments, the environmental sensor 560 may be multiple environmental sensors. For example, the COPA device 100 may include a separate temperature sensor, a separate humidity sensor, a separate $CO_2$ sensor, etc., and each of the above sensors may be located at different respective locations on the COPA device 100. For example, the temperature sensor may be located on the outer face 129 of the back wall portion 128 of the COPA device 100, and the humidity sensor may be located on the outer face 127 of the front wall portion 126 of the COPA device 100. In other embodiments, the COPA device 100 may include duplicates of the environmental sensor 560. Each of the duplicates of the environmental sensor 560 may be located at different respective locations on the COPA device 100. For example, one environmental sensor 560 may be located on the outer face 129 of the back wall portion 128 of the COPA device 100, and another environmental sensor may be located on the outer face 127 of the front wall portion 126 of the COPA device 100.

Figure 13:
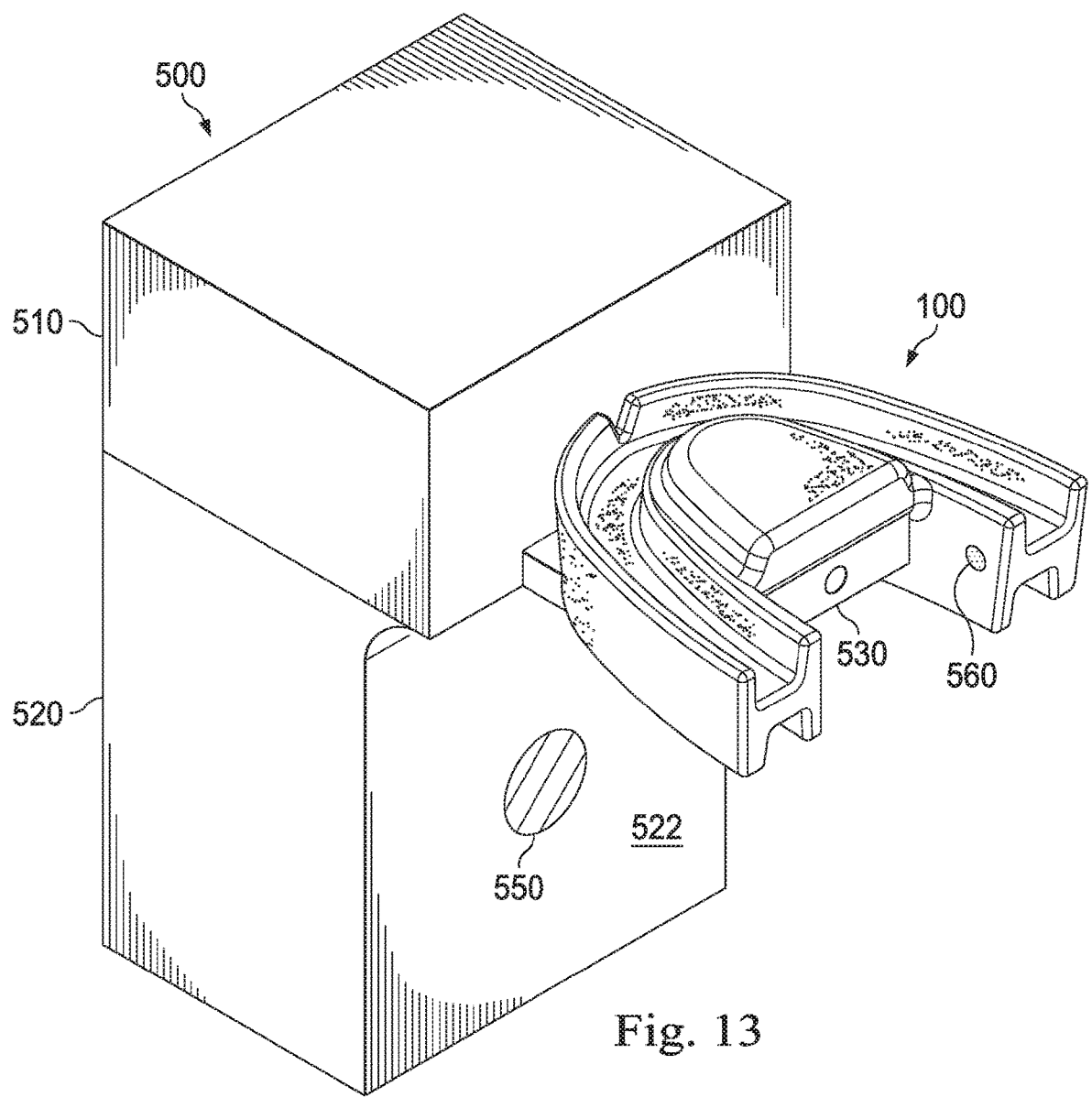
FIG. 13 is a perspective view of a COPA device coupled to a housing according to embodiments of the present disclosure.

FIG. 13 provides a perspective view of the COPA device 100 coupled to the housing 500 according to embodiments of the present disclosure. In some embodiments, the COPA device 100 may be mechanically coupled and fluidly coupled to the housing 500. The COPA device 100 is mechanically coupled to the housing 500 via the docking port 530 (FIG. 10) such that the COPA device 100 and the housing 500 move together. The COPA device 100 is fluidly coupled (or in fluid communication with) the housing 500 via the tubular member 540 such that a prescribed substance (e.g., the prescribed substance 720) travels from the housing 500 to the COPA device 100 via the tubular member 540. In the embodiment shown in FIG. 13, the housing 500 includes the biometric sensor 550 (FIG. 9). Further, the COPA device 100 includes the environmental sensor 560 (FIG. 12).

FIG. 14 provides a perspective view of an interior of the housing 500 according to embodiments of the present disclosure. In the embodiment shown in FIG. 14, the housing 500 includes a medication bottle 590, a cap 592, a dip tube 594, a valve 596, a pump 598, a tubular connector 580, and the tubular member 540 (see FIG. 15). The medication bottle 590 may be the reservoir 320 (FIG. 6). The pump 598 may be the actuator 330 (FIG. 6), and the valve 596 may be similar to the exit valves 340 (FIG. 6).

The medication bottle 590 may be used to hold a prescribed substance, which may be the prescribed substance 720. In some embodiments, the prescribed substance 720 may be in liquid form. For example, the prescribed substance 720 may be a liquid form of oxycodone Hydrochloride, morphine concentrate, lorazepam, Zoloft sertraline HCL, or any other suitable substance. In some examples, the prescribed substance 720 may be any of the substances listed above or any substance that has not yet been produced, created, developed, or manufactured, but may be produced, created, developed, or manufactured in the future. The prescribed substance 720 may be a combination of any of the substances listed above or a combination of the substances listed above with substances that have not yet been produced, created, developed, or manufactured, or with any other suitable substance. In other embodiments, the medication bottle 590 may include a prescribed substance in the form of pellets, granules, micro particles, mini tablets, powders, pills, etc. The medication bottle 590 may be sized to contain multiple doses (e.g., a day(s), week(s), month(s), etc.) of the prescribed substance based on the intended user's dosage information. In some instances, the volume of the medication bottle 590 is equal to or greater than 15 ml, 30 ml, 60 ml, 90 ml, 120 ml, 180 ml, 240 ml, 360 ml, 480 ml, or more. The volume of the medication bottle 590 may be sized based on expected dosage sizes, expected substance form (e.g., liquid, pellets, granules, micro particles, mini tablets, powders, pills, etc.), and/or combinations thereof.

The pump 598 can be utilized to dispense the prescribed substance from the medication bottle 590, through the COPA device 100, and into the intended user's mouth via a tubular connector 580 and the tubular member 540 (FIG. 10). In this regard, the components in the interior of the housing 500 may be similar to the micro-pump unit 300 described above (FIGS. 6-8). In some instances, the tubular connector 580 may be replaced by the tubular member 540, such that the tubular member 540 extends from the COPA device 100, through the pump 598, and connects to the valve 596. In other instances, the tubular member 540 may be replaced by the tubular connector 580, such that the tubular connector 580 extends from the valve 596, through the pump 598, and connects to the COPA device 100.

In some embodiments, a distal end 600 of the dip tube 594 is disposed within the medication bottle 590 so that the distal end 600 of the dip tube 594 terminates just above a base 591 of the medication bottle 590. Thus, substantially all of a length of the dip tube 594 may be positioned within the medication bottle 590. This may allow for the prescribed substance 720 to enter the distal end 600 of the dip tube 594 and flow through the dip tube 594, which may be a hollow tube. A proximal end 602 of the dip tube 594 may be connected to a distal end 604 of the valve 596. A proximal end 606 of the valve 596 may be connected to a distal end 608 of the tubular connector 580. A proximal end 610 of the tubular connector 580 may be connected to a distal end 612 of the pump 598, and a proximal end 614 of the pump 598 may be connected to a distal end 616 of the tubular member 540. A proximal end 618 of the tubular member 540 may terminate within the COPA device 100. In some embodiments, the tubular member 540 connects to the reservoir 320 (FIG. 7) of the micro-pump unit 300, which then delivers the prescribed substance 720 into the user's mouth via the exit valves 340 (FIG. 7). In other embodiments, the tubular member 540 extends through the COPA device 100 and into the docking port 530, and the prescribed substance 720 is delivered into the user's mouth via an exit port 532 in the docking port 530. In various examples, the tubular member 540 extends through the COPA device 100 and the docking port 530 and connects to the exit port 532. The prescribed substance 720 is then delivered into the user's mouth via the tubular member 540. Any one of the respective connections such as the connections between one or more of the dip tube 594, the valve 596, the tubular connector 580, the pump 598, the tubular member 540, the docking port 530, the exit port 532, and/or the COPA device 100 described above may be a male/female engagement, a snap fit, a press fit, a threaded engagement, an adhesive connection, a solder engagement, a fastened engagement, a welded connection, a brazing connection, or any other suitable coupling to facilitate transfer of the prescribed substance 720.

In some embodiments, the tubular member 540 may be in fluid communication and mechanical communication, such as physically coupled, with the pump 598 and the COPA device 100, respectively. In other embodiments, the dip tube 594 may be in fluid communication and mechanical communication, such as physically coupled, with the valve 596.

Figure 15:
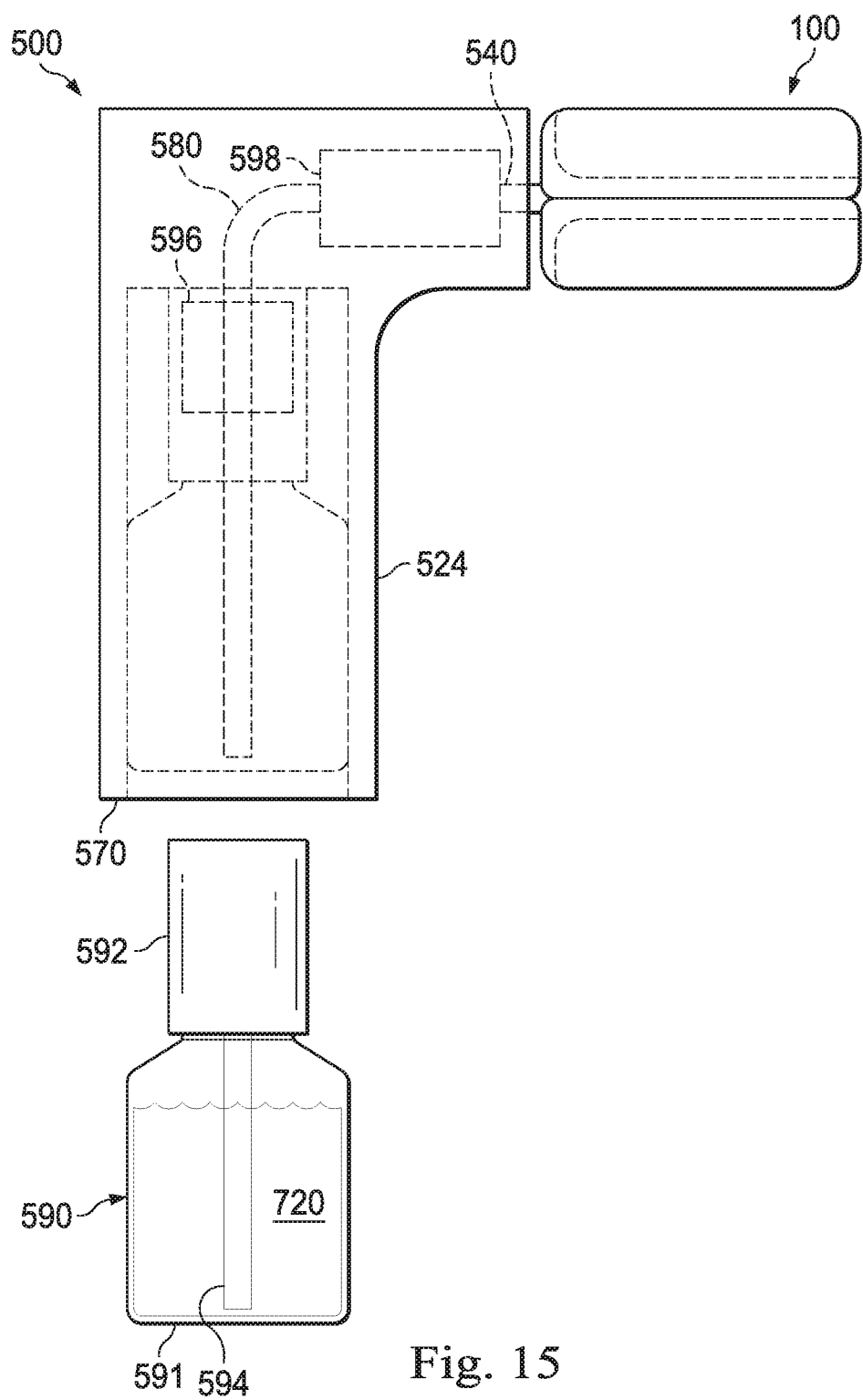
FIG. 15 is a cross-sectional view of a housing along section line 15-15 in FIG. 14 according to embodiments of the present disclosure.

FIG. 15 provides a detailed view of the housing 500 with the medication bottle 590 positioned outside of the housing 500. In this regard, FIG. 15 is a cross-sectional view of the housing 500 according to embodiments of the present disclosure. The cross-sectional view is taken along section line 15-15 of FIG. 14. In the embodiment of FIG. 15, the medication bottle 590 is positioned outside of the housing 500, and the medication bottle 590 is filled with the prescribed substance 720. The medication bottle 590 may only be directly handled by an authorized person, such as a pharmacist. The user may not directly handle the medication bottle 590 to prevent unauthorized access to the prescribed substance 720. In some instances, an authorized person may, after receiving the medication bottle 590 from a supplier, remove the original cap of the medication bottle 590 and replace the original cap with a custom cap, such as the cap 592. The cap 592 may include the dip tube 594 and the valve 596. In various examples, the cap 592 and/or the medication bottle 590 can include threads, and the medication bottle 590 and/or the cap 592 can include corresponding grooves to receive the threads. In this manner, the cap 592 and the medication bottle 590 can be threadingly coupled.

In some embodiments, after placing the cap 592 on the medication bottle 590, the authorized person may insert the medication bottle 590 into the housing 500. To insert the medication bottle 590 into the housing 500, the authorized person may first remove the bottom wall 570 of the housing 500. Then, the authorized person may insert the medication bottle 590 into the lower portion 520 of the housing 500. After inserting the medication bottle 590 into the lower portion 520, the authorized person may replace the bottom wall 570 and lock the bottom wall 570 in place with a locking mechanism to securely seal the bottom wall 570 onto the housing 500 in a manner that prevents unauthorized access to the medication bottle 590. In some embodiments, the locking mechanism may be a key lock, a magnetic lock, an electronic lock, a mechanical lock, a quick connect lock, or any other suitable locking mechanism. In some embodiments, the locking mechanism may securely seal the bottom wall 570 to the front wall 524 when the front wall 524 is coupled to the bottom wall 570.

Figure 16:
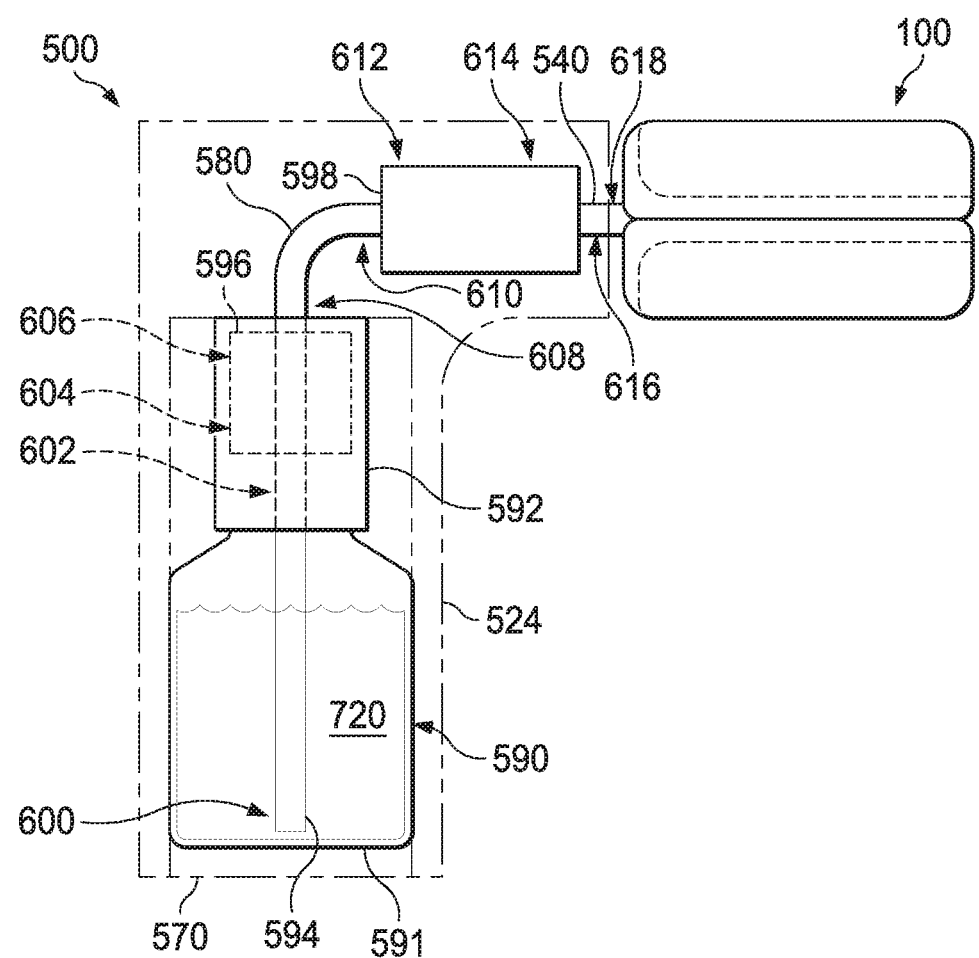
FIG. 16 is a cross-sectional view of a housing along section line 15-15 in FIG. 14 according to embodiments of the present disclosure.

FIG. 16 provides a detailed view of the housing 500 with the medication bottle 590 positioned inside of the housing 500. In this regard, FIG. 16 is a cross-sectional view of the housing 500 according to embodiments of the present disclosure. The cross-sectional view is taken along section line 15-15 of FIG. 14. In the embodiment of FIG. 16, the medication bottle 590 is positioned within the housing 500, and the medication bottle 590 is filled with the prescribed substance 720. In some embodiments, the pump 598 can be utilized to dispense the prescribed substance 720 from the medication bottle 590 into the intended user's mouth after the processor 310 determines that the intended user's fingerprint has been scanned by the biometric sensor 550 (FIG. 9), after the processor 310 determines that the COPA device 100 is within the intended user's mouth (as discussed above with respect to FIG. 12), and/or after the processor 310 determines that the intended user's mouth is within the recess of the COPA device 100 (which will be discussed in greater detail herein with respect to FIGS. 18-25B). In some instances, the prescribed substance 720 travels from the medication bottle 590 to the intended user's mouth via the dip tube 594, the valve 596, the tubular connector 580, the pump 598, the tubular member 540, the docking port 530, and the exit port 532.

In some embodiments, after a dosage has been delivered to the intended user, the valve 596 may purge the tubular connector 580, the pump 598, and the tubular member 540 with air. For example, the valve 596 may inject air into the tubular connector 580, the pump 598, and the tubular member 540. The injection of air may ensure that any remaining residue from the dosage of the prescribed substance 720 is removed from the tubular connector 580, the pump 598, and the tubular member 540. In some instances, the valve 596 may be a purge valve, a canister purge valve, a check valve, a pinch valve, a diaphragm valve, a solenoid valve, a ball valve, or any other suitable valve. In some embodiments, the pump 598 may continue to provide dosages, one at a time, of the prescribed substance 720 to the intended user according to a dosage time table and/or a dosage schedule. Doses may continue to be delivered for the prescribed period of time, for the prescribed number of doses, and/or until the amount of the prescribed substance 720 in the medication bottle 590 is depleted.

Figure 17:
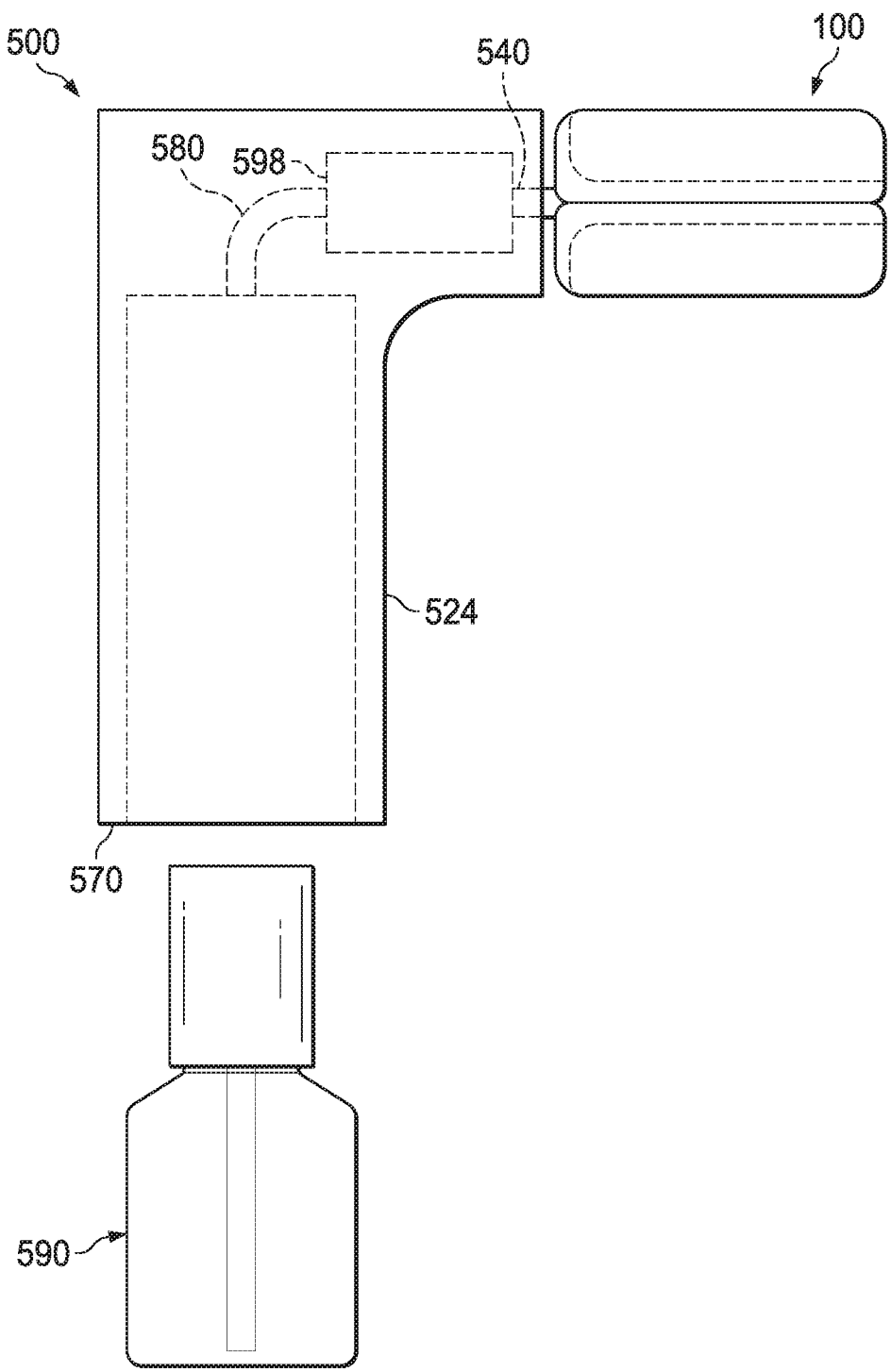
FIG. 17 is a cross-sectional view of a housing along section line 15-15 in FIG. 14 according to embodiments of the present disclosure.

FIG. 17 provides a detailed view of the housing 500 with an empty medication bottle 590 positioned outside of the housing 500. In this regard, FIG. 17 is a cross-sectional view of the housing 500 according to embodiments of the present disclosure. The cross-sectional view is taken along section line 15-15 of FIG. 14. In the embodiment of FIG. 17, the medication bottle 590 is positioned outside of the housing 500, and the medication bottle 590 is empty (i.e., all of the prescribed substance 720 is removed from the medication bottle 590). In some instances, after the medication bottle 590 is empty, the user may bring the housing 500 to an authorized person, such as a pharmacist. When the authorized person receives the housing 500 from the user, the authorized person may remove the bottom wall 570 from the housing 500. To remove the bottom wall 570, the authorized person may unlock the bottom wall 570 from the housing 500. Then, the authorized person may remove the empty medication bottle 590 from the housing 500. In some embodiments, the authorized person may refill the medication bottle 590 with the prescribed substance 720 and place the medication bottle 590 back into the housing 500. After placing the medication bottle 590 within the housing 500, the authorized person may lock the bottom wall 570 onto the housing 500.

In other embodiments, after the authorized person removes the empty medication bottle 590 from the housing 500, the authorized person may not need to refill the medication bottle 590 with the prescribed substance 720. For example, the authorized person may not need to refill the medication bottle 590 when the user's dosage schedule is complete. If the user's dosage schedule is complete, then the authorized person may keep the housing 500 with the attached COPA device 100 to be sterilized and then used for a subsequent user. In some embodiments, the authorized user may remove the medication bottle 590 from the housing 500 while the medication bottle is partially full of the prescribed substance 720. For example, the medication bottle 590 may be partially full even after the prescribed period of time has passed and/or after the prescribed number of doses have been administered.

While it has been discussed above with respect to FIGS. 15-17 that an authorized person may unlock and remove the bottom wall 570 of the housing 500 in order to access the medication bottle 590, it is understood that any other wall of the housing 500 may be removed in order to access the medication bottle 590. For example, the authorized person may unlock and remove a back wall or a side wall of the housing 500 to access the medication bottle 590.

Figure 18:
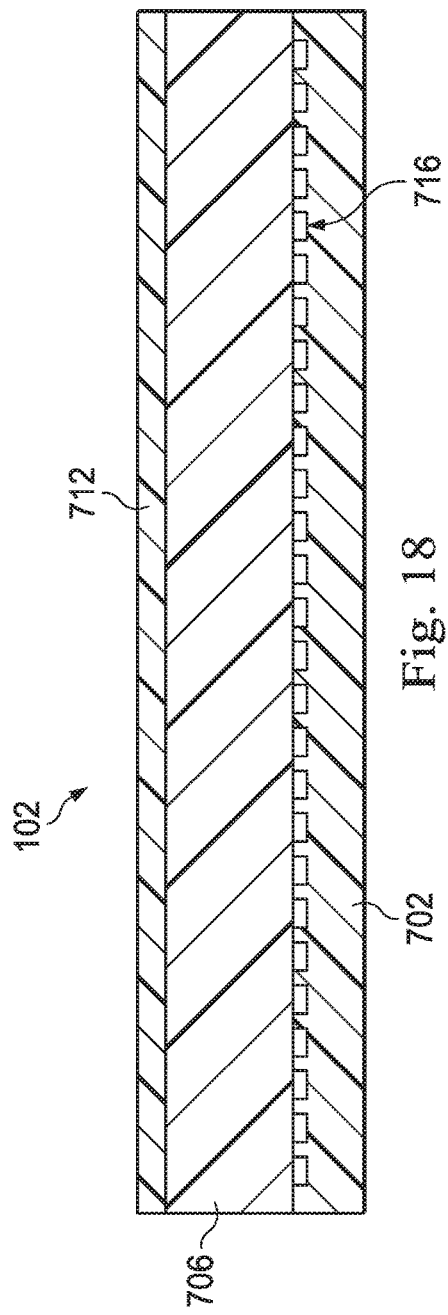
FIG. 18 is a cross-sectional view of a top side of a COPA device along section line 18-18 in FIG. 1 according to embodiments of the present disclosure.

FIG. 18 provides a detailed view of the top side 102 of the COPA device 100 according to embodiments of the present disclosure. In this regard, FIG. 18 is a cross-sectional view of the COPA device 100 according to embodiments of the present disclosure. The cross-sectional view is taken along section line 18-18 of FIG. 1. The top side 102 includes a top side outer layer 712, a top side intermediate layer 706, and a base layer 702. The top side outer layer 712 is adjacent to the top side intermediate layer 706, and the top side intermediate layer 706 is adjacent to the base layer 702. The top side outer layer 712 may be substantially planar. This may allow the COPA device 100 to fit within a plurality of different mouths with a plurality of different dentitions.

In some embodiments, the top side intermediate layer 706 may be positioned under and in contact with the top side outer layer 712. The top side intermediate layer 706 may be directly in contact with the top side outer layer 712. For example, a top surface of the top side intermediate layer 706 may be in contact with a bottom surface of the top side outer layer 712. In some embodiments, the top side intermediate layer 706 may be connected to the top side outer layer 712.

In some embodiments, the base layer 702 may be positioned under and in contact with the top side intermediate layer 706. The base layer 702 may be directly in contact with the top side intermediate layer 706. For example, a top surface of the base layer 702 may be in contact with a bottom surface of the top side intermediate layer 706. In some embodiments, the base layer 702 may be connected to the top side intermediate layer 706.

Additionally, a top side capacitive sensor array 716 may be embedded within the base layer 702. The top side capacitive sensor array 716 may be positioned within the base layer 702 to be adjacent to the top side intermediate layer 706 (e.g., adjacent to a bottom surface of the top side intermediate layer 706). In some embodiments, the top side capacitive sensor array 716 may be composed of a plurality of capacitance sensors. The plurality of capacitance sensors may be arranged in a straight line. In other embodiments, the plurality of capacitance sensors may be arranged in several rows of straight lines. In some embodiments, the plurality of capacitance sensors may be arranged in any other suitable pattern including curved patterns and/or non-linear patterns.

In some embodiments, both the top side outer layer 712 and the top side intermediate layer 706 are made of a biocompatible impression material or polymer. The base layer 702 may be made of a biocompatible impression material or polymer, or the base layer 702 may be made of a more rigid material. For example, the base layer 702 may be made of closed cell foam, nonconductive gel, rubber, paper, polyester, polystyrene, polypropylene, plastic, porcelain, Teflon, ceramic, fiberglass, or any other suitable material. The top side outer layer 712 and the top side intermediate layer 706 may be deformable so that the layers deform when a user bites down on the COPA device 100.

The plurality of capacitance sensors in the top side capacitive sensor array 716 may be any suitable type of capacitance sensors. For example, the plurality of capacitance sensors may be object detection sensors, level detection sensors, capacitive displacement sensors, capacitive proximity sensors, mutual capacitance sensors, self-capacitance sensors, and any other suitable capacitance sensors. A capacitor is a device that consists of two electrodes separated by an insulator (e.g., a dielectric). In some examples, the dielectric may be air, mica, Mylar, rubber, paper, polyester, polystyrene, polypropylene, plastic, porcelain, Teflon, ceramic, solder mask, fiberglass, glass, or any other suitable insulating material (e.g., a gas, liquid, or solid material). In some embodiments, the capacitance sensors may be integrated capacitors. In some examples, the integrated capacitors may take the form of plates/planar electrodes, rods, tubes, purchased sensors, modified sensors, custom sensors, or any combination of materials that results in the generation of an electric field that can be interacted with to modify the materials' capacitance. In some embodiments, the capacitance sensors in the top side capacitive sensor array 716 detect dentition positioning, arrangement, shape, and any other suitable dentition-related measurement.

The top side outer layer 712 may be made of a capacitive material (e.g., any suitable material containing at least one layer of electrically conductive material or any material that is impregnated and/or metalized with conductive material, such as anti-static conductive foam, for example). In some examples, the top side intermediate layer 706 may be made of a nonconductive material that will deform under pressure and then recover. For example, the top side intermediate layer 706 may be made of rubber, nonconductive gel, closed cell foam, or any other suitable material. In some embodiments, the top side outer layer 712 may be removably coupled to the top side intermediate layer 706. For example, in some embodiments, the top side outer layer 712 may be removed from the top side 102. The top side outer layer 712 may be removed when the user has a sufficient number of structural features (e.g., prosthetics, such as crowns, bridges, metallic fillings, etc.) on the user's teeth that a sufficient capacitive map of the user's dentition will be detected by the top side capacitive sensor array 716.

Figure 19:
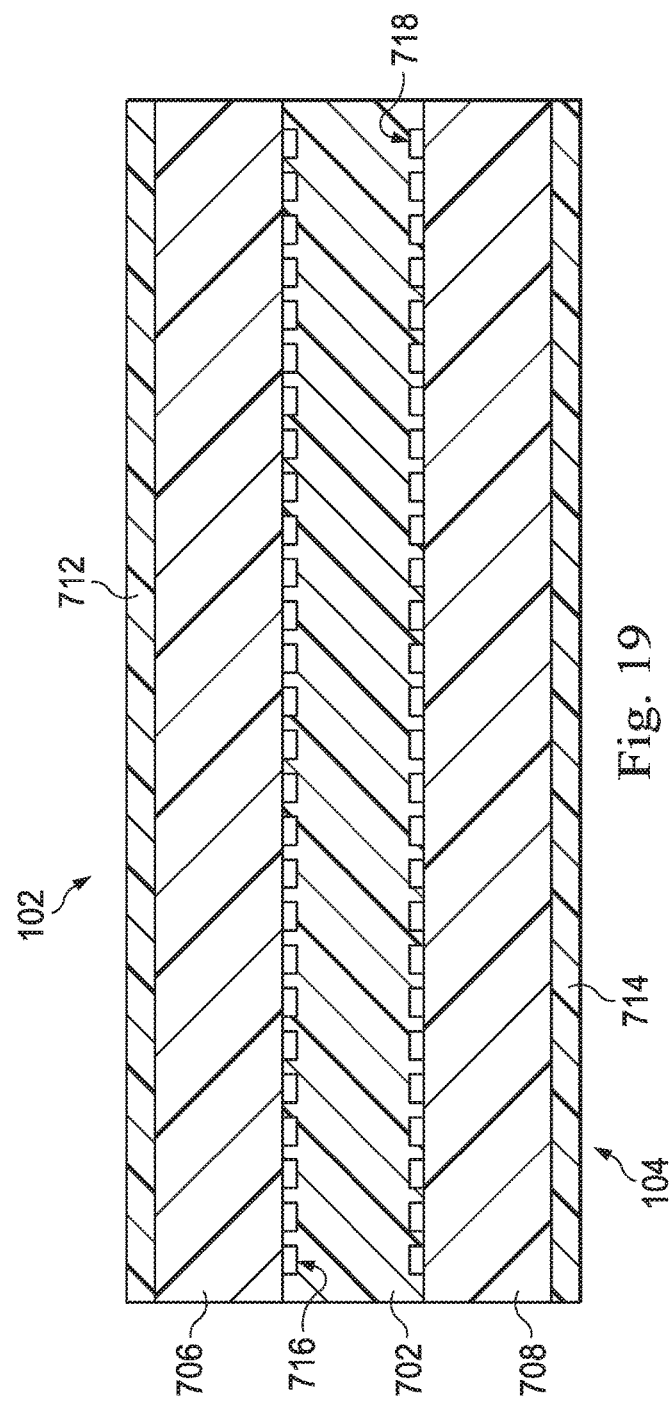
FIG. 19 is a cross-sectional view of a top and bottom side of a COPA device along section line 18-18 in FIG. 1 according to embodiments of the present disclosure.

FIG. 19 provides a detailed view of the top side 102 and the bottom side 104 of the COPA device 100 according to embodiments of the present disclosure. In this regard, FIG. 19 is a cross-sectional view of the COPA device 100 according to embodiments of the present disclosure. The cross-sectional view is taken along section line 18-18 of FIG. 1. As discussed above with respect to FIG. 1, the bottom side 104 includes a bottom side outer layer 714 and a bottom side intermediate layer 708. The bottom side outer layer 714 is adjacent to the bottom side intermediate layer 708, and the bottom side intermediate layer 708 is adjacent to the base layer 702. The bottom side outer layer 714 may be substantially planar. This may allow the COPA device 100 to fit within a plurality of different mouths with a plurality of different dentitions.

In some embodiments, the bottom side intermediate layer 708 may be positioned under and in contact with the bottom side outer layer 714. The bottom side intermediate layer 708 may be directly in contact with the bottom side outer layer 714. For example, a top surface of the bottom side intermediate layer 708 may be in contact with a bottom surface of the bottom side outer layer 714. In some embodiments, the bottom side intermediate layer 708 may be connected to the bottom side outer layer 714.

In some embodiments, the base layer 702 may be positioned under and in contact with the bottom side intermediate layer 708. The base layer 702 may be directly in contact with the bottom side intermediate layer 708. For example, a bottom surface of the base layer 702 may be in contact with a bottom surface of the bottom side intermediate layer 708. In some embodiments, the base layer 702 may be connected to the bottom side intermediate layer 708.

Additionally, a bottom side capacitive sensor array 718 may be embedded within the base layer 702. The bottom side capacitive sensor array 718 may be positioned within the base layer 702 to be adjacent to the bottom side intermediate layer 708 (e.g., adjacent to a bottom surface of the bottom side intermediate layer 708). As shown in FIG. 19, both the top side capacitive sensor array 716 and the bottom side capacitive sensor array 718 may each be embedded within the base layer 702. In some embodiments, the bottom side capacitive sensor array 718 may be composed of a plurality of capacitance sensors. The plurality of capacitance sensors may be arranged in a straight line. In other embodiments, the plurality of capacitance sensors may be arranged in several rows of straight lines. In some embodiments, the plurality of capacitance sensors may be arranged in any other suitable pattern including curved patterns and/or non-linear patterns.

In some embodiments, both the bottom side outer layer 714 and the bottom side intermediate layer 708 are made of a biocompatible impression material or polymer. For example, the base layer 702 may be made of closed cell foam, nonconductive gel, rubber, paper, polyester, polystyrene, polypropylene, plastic, porcelain, Teflon, ceramic, fiberglass, or any other suitable material. The bottom side outer layer 714 and the bottom side intermediate layer 708 may be deformable so that the layers deform when a user bites down on the COPA device 100.

The plurality of capacitance sensors in the bottom side capacitive sensor array 718 may be any suitable type of capacitance sensors. For example, the plurality of capacitance sensors may be object detection sensors, level detection sensors, capacitive displacement sensors, capacitive proximity sensors, mutual capacitance sensors, self-capacitance sensors, and any other suitable capacitance sensors. As discussed above with respect to FIG. 18, a capacitor is a device that consists of two electrodes separated by an insulator (e.g., a dielectric). In some examples, the dielectric may be air, mica, Mylar, rubber, paper, polyester, polystyrene, polypropylene, plastic, porcelain, Teflon, ceramic, solder mask, fiberglass, glass, or any other suitable insulating material (e.g., a gas, liquid, or solid material). In some embodiments, the capacitance sensors may be integrated capacitors. In some examples, the integrated capacitors may take the form of plates/planar electrodes, rods, tubes, purchased sensors, modified sensors, custom sensors, or any combination of materials that results in the generation of an electric field that can be interacted with to modify the materials' capacitance. In some embodiments, the capacitance sensors in the bottom side capacitive sensor array 718 detect dentition positioning, arrangement, shape, and any other suitable dentition-related measurement.

The bottom side outer layer 714 may be made of a capacitive material (e.g., any suitable material containing at least one layer of electrically conductive material or any material that is impregnated and/or metalized with conductive material, such as anti-static conductive foam, for example). In some examples, the bottom side intermediate layer 708 may be made of a nonconductive material that will deform under pressure and then recover. For example, the bottom side intermediate layer 708 may be made of rubber, nonconductive gel, closed cell foam, or any other suitable material. In some embodiments, the bottom side outer layer 714 may be removably coupled to the bottom side intermediate layer 708. For example, in some embodiments, the bottom side outer layer 714 may be removed from the bottom side 104. The bottom side outer layer 714 may be removed when the user has a sufficient number of structural features (e.g., prosthetics, such as crowns, bridges, metallic fillings, etc.) on the user's teeth that a sufficient capacitive map of the user's dentition will be detected by the bottom side capacitive sensor array 718.

Figure 20:
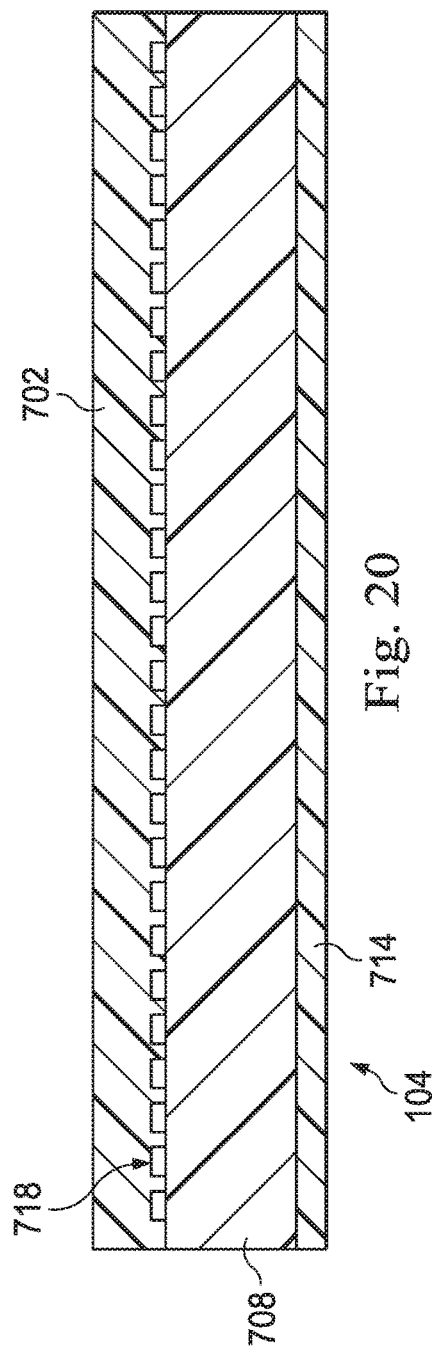
FIG. 20 is a cross-sectional view of a bottom side of a COPA device along section line 18-18 in FIG. 1 according to embodiments of the present disclosure.
Figure 24:
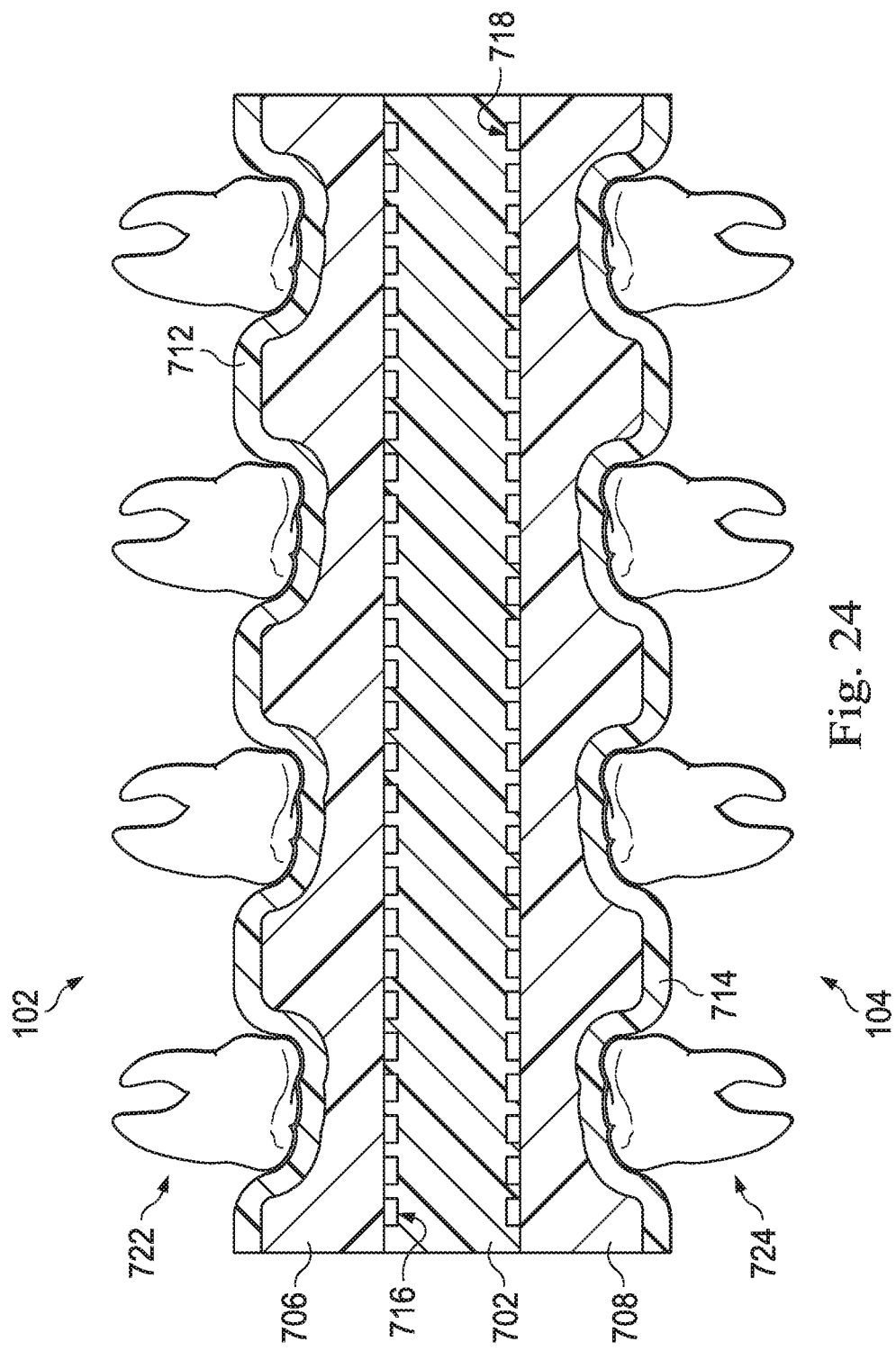
FIG. 24 is a cross-sectional view of a top and bottom side of a COPA device in a deformed state along section line 18-18 in FIG. 1 according to embodiments of the present disclosure.

FIG. 20 provides a detailed view of the bottom side 104 of the COPA device 100 according to embodiments of the present disclosure. In this regard, FIG. 20 is a cross-sectional view of the COPA device 100 according to embodiments of the present disclosure. The cross-sectional view is taken along section line 18-18 of FIG. 1. In some embodiments, the COPA device includes a capacitive sensor array only on the top side 102 (FIG. 18). In other embodiments, the COPA device includes a capacitive sensor array only on the bottom side 104 (FIG. 20). In still other embodiments, the COPA device includes a capacitive sensor array on both the top side 102 and the bottom side 104 (FIGS. 19, 21, 24).

Figure 21:
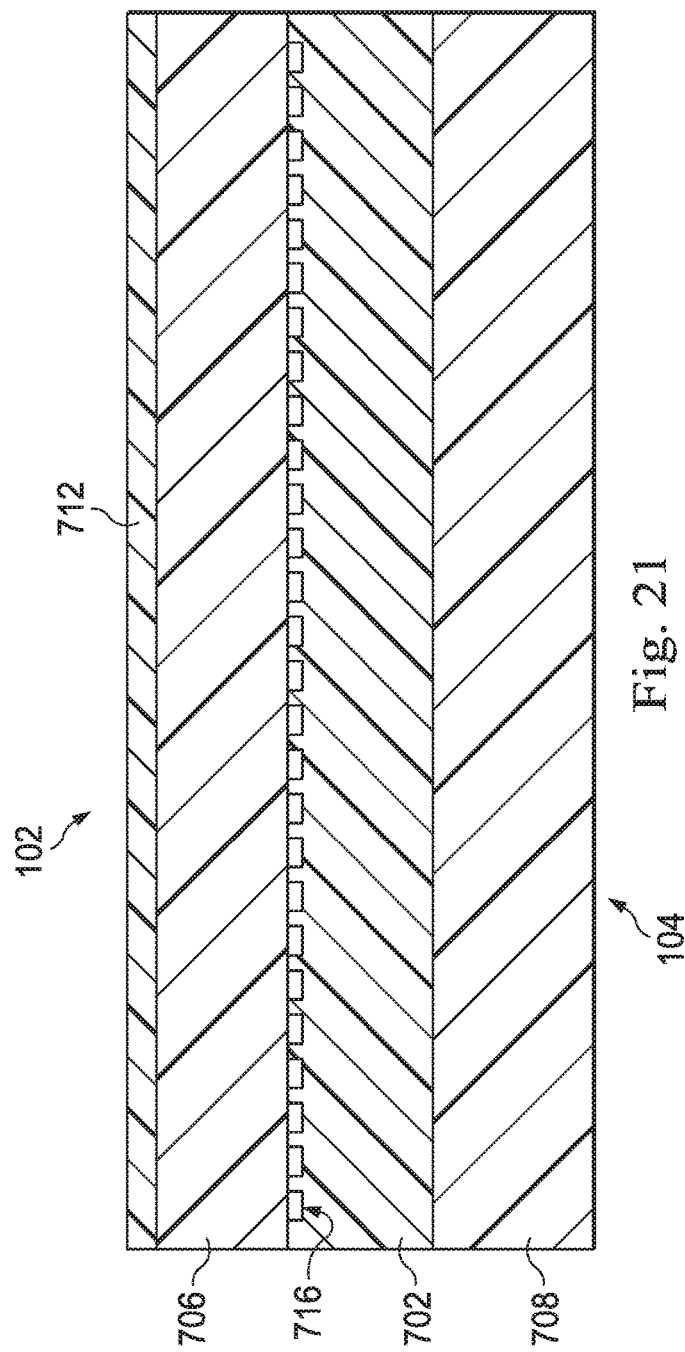
FIG. 21 is a cross-sectional view of a top and bottom side of a COPA device along section line 18-18 in FIG. 1 according to embodiments of the present disclosure.

FIG. 21 provides a detailed view of the top side 102 and the bottom side 104 of the COPA device 100 according to embodiments of the present disclosure. In this regard, FIG. 21 is a cross-sectional view of the COPA device 100 according to embodiments of the present disclosure. The cross-sectional view is taken along section line 18-18 of FIG. 1. In the embodiment shown in FIG. 21, the top side 102 includes the top side outer layer 712 and the top side intermediate layer 706. Compared to FIG. 19, the embodiment of FIG. 21 omits the bottom side capacitive sensor array 718 and the bottom side outer layer 714. The base layer 702 includes only the top side capacitive sensor array 716, and the bottom side 104 includes only the bottom side intermediate layer 708. The embodiment shown in FIG. 21 may result in lower manufacturing costs for manufacturing the COPA device 100 because the COPA device 100 in FIG. 21 includes fewer layers than, for example, the COPA device 100 in FIG. 19. Additionally, the COPA device 100 shown in FIG. 21 may provide more comfort to the user due to there being fewer layers.

FIG. 22 provides a detailed view of the top side 102 of the COPA device 100 according to embodiments of the present disclosure. In this regard, FIG. 22 is a cross-sectional view of the COPA device 100 according to embodiments of the present disclosure. The cross-sectional view is taken along section line 18-18 of FIG. 1. Compared to FIG. 18, the embodiment of FIG. 22 omits the top side outer layer 712. In the embodiment shown in FIG. 22, the top side 102 includes only the top side intermediate layer 706 and the base layer 702 (which includes the top side capacitive sensor array 716). The embodiment shown in FIG. 22 may result in lower manufacturing costs for manufacturing the COPA device 100 because the COPA device 100 in FIG. 22 includes fewer layers than, for example, the COPA device 100 in FIG. 18. Additionally, the COPA device 100 shown in FIG. 22 may provide more comfort to the user due to there being fewer layers.

The COPA device 100 can be formed of any combination of layers and capacitive sensor arrays as discussed above according to embodiments of the present disclosure. The COPA device 100 can also be formed of any combination of layers and capacitive sensor arrays that may not have been discussed above but would be a suitable combination.

FIG. 23 provides a detailed view of the top side 102 of the COPA device 100 according to embodiments of the present disclosure. In this regard, FIG. 23 is a cross-sectional view of the COPA device 100 according to embodiments of the present disclosure. The cross-sectional view is taken along section line 18-18 of FIG. 1. In the embodiment shown in FIG. 22, the top side 102 is depicted in a state of deformation. The deformation of the top side 102 is caused by a plurality of upper teeth 722 of the user. When the user bites down on the top side 102, the top side outer layer 712 and the top side intermediate layer 706 may deform due to pressure applied by the plurality of upper teeth 722 on the top side outer layer 712. In some embodiments, the top side capacitive sensor array 716 generates a signal/input (e.g., a capacitive map) based on the deformation. The processor 310 may then receive the signal/input.

FIG. 24 provides a detailed view of the top side 102 and the bottom side 104 of the COPA device 100 according to embodiments of the present disclosure. In this regard, FIG. 24 is a cross-sectional view of the COPA device 100 according to embodiments of the present disclosure. The cross-sectional view is taken along section line 18-18 of FIG. 1.

In the embodiment shown in FIG. 24, the top side 102 and the bottom side 104 are each depicted in a state of deformation. The deformation of the top side 102 is caused by a plurality of upper teeth 722 of the user, and the deformation of the bottom side 104 is caused by a plurality of lower teeth 724 of the user. When the user bites down on the top side 102, the top side outer layer 712 and the top side intermediate layer 706 may deform due to pressure applied by the plurality of upper teeth 722 on the top side outer layer 712. When the user bites on the bottom side 104, the bottom side outer layer 714 and the bottom side intermediate layer 708 may deform due to pressure applied by the plurality of lower teeth 724 on the bottom side outer layer 714.

In some embodiments, the base layer 702 may not deform or may only deform a marginal amount. The base layer 702 may not deform to ensure the top side capacitive sensor array 716 and/or the bottom side capacitive sensor array 718 accurately detects any changes in capacitance. The top side capacitive sensor array 716 may detect changes in capacitance based on deformation of the top side intermediate layer 706 and/or the top side outer layer 712. The deformation may be caused by the user biting down on the top side 102 of the COPA device 100. The detected changes in capacitance may be in the form of a capacitive map, which includes capacitance readings for all or substantially all of the user's upper teeth (e.g., the plurality of upper teeth 722). The top side capacitance sensor array 716 may detect multiple capacitive maps based on multiple inputs (e.g., deformation of the top side intermediate layer 706 and/or the top side outer layer 712) in order to define a range of acceptable capacitive map matches associated with the intended user. This may require the user to bite down on the top side 102 of the COPA device 100 multiple times in order for the top side capacitive sensor array 716 to generate multiple capacitive maps.

The bottom side capacitive sensor array 718 may detect changes in capacitance based on deformation of the bottom side intermediate layer 708 and/or the bottom side outer layer 714. The deformation may be caused by the user biting on the bottom side 104 of the COPA device 100. The detected changes in capacitance may be in the form of a capacitive map, which includes capacitance readings for all or substantially all of the user's lower teeth (e.g., the plurality of lower teeth 724). The bottom side capacitance sensor array 718 may detect multiple capacitive maps based on multiple inputs (e.g., deformation of the bottom side intermediate layer 708 and/or the bottom side outer layer 714) in order to define a range of acceptable capacitive map matches associated with the intended user. This may require the user to bite on the bottom side 104 of the COPA device 100 multiple times in order for the bottom side capacitive sensor array 718 to generate multiple capacitive maps.

Figure 25A:
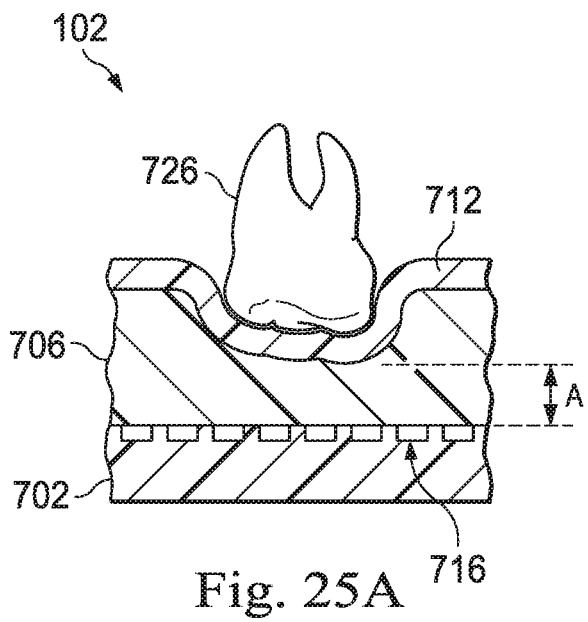
FIG. 25A is a cross-sectional view of a top side of a COPA device in a deformed state along section line 18-18 in FIG. 1 according to embodiments of the present disclosure.

FIG. 25A provides a detailed view of the top side 102 of the COPA device 100 according to embodiments of the present disclosure. In this regard, FIG. 25A is a cross-sectional view of the COPA device 100 according to embodiments of the present disclosure. The cross-sectional view is taken along section line 18-18 of FIG. 1. In the embodiment shown in FIG. 25A, the top side 102 is depicted in a state of deformation. The deformation of the top side 102 is caused by a plurality of upper teeth 722 of the user (see FIG. 24). FIG. 25A illustrates an upper tooth 726 (which may be part of the plurality of upper teeth 722), which is causing deformation of a portion of the top side 102 according to embodiments of the present disclosure. An amount of deformation in FIG. 25A is illustrated by distance A, which is a distance between a top surface of the top side capacitive sensor array 716 and a bottom surface of the top side outer layer 712.

In the embodiment shown in FIG. 25A, the top side 102 includes the top side outer layer 712. As discussed previously, the top side outer layer 712 may be made of a capacitive material. Therefore, when the top side outer layer 712 is deformed (e.g., when the user bites down on the top side 102), the processor 310 receives an input from the top side capacitive sensor array 716 based on the deformation. The top side outer layer 712 is included in the top side 102 in this embodiment because the upper tooth 726 does not have any capacitive structural features (e.g., prosthetics, such as a crown, a bridge, a metallic filling, etc.). Having the top side outer layer 712 allows for capacitance to be detected by the processor 310 even if the upper tooth 726 and/or top side intermediate layer 706 do not themselves have enough capacitance. When the top side outer layer 712 is included, the processor 310 will receive an input from the top side capacitive sensor array 716 based on deformation of the top side outer layer 712.

Figure 25B:
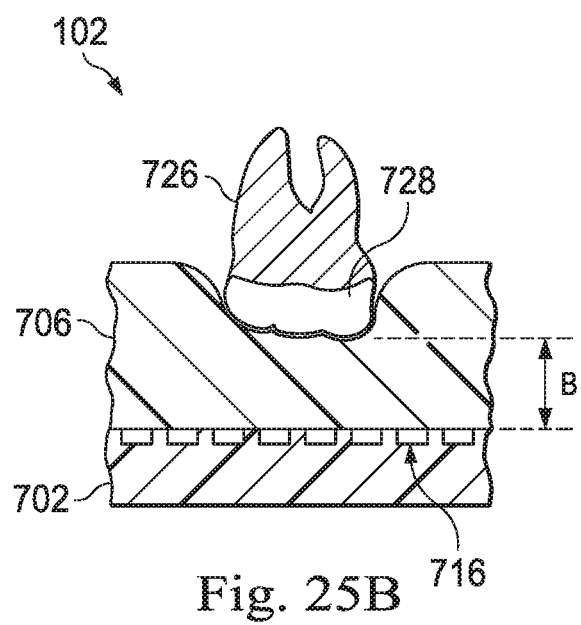
FIG. 25B is a cross-sectional view of a top side of a COPA device in a deformed state along section line 18-18 in FIG. 1 and with an upper tooth with a structural feature according to embodiments of the present disclosure.

FIG. 25B provides a detailed view of the top side 102 of the COPA device 100 according to embodiments of the present disclosure. In this regard, FIG. 25B is a cross-sectional view of the COPA device 100 according to embodiments of the present disclosure. The cross-sectional view is taken along section line 18-18 of FIG. 1. In the embodiment shown in FIG. 25B, the top side 102 is depicted in a state of deformation. The deformation of the top side 102 is caused by a plurality of upper teeth 722 of the user (see FIG. 24). FIG. 25B illustrates an upper tooth 726 (which may be part of the plurality of upper teeth 722), which is causing deformation of a portion of the top side 102 according to embodiments of the present disclosure. An amount of deformation in FIG. 25B is illustrated by distance B, which is a distance between a top surface of the top side capacitive sensor array 716 and a top surface of the top side intermediate layer 706.

Compared to FIG. 25A, the embodiment of FIG. 25B omits the top side outer layer 712. Thus, in the embodiment shown in FIG. 25B, the top side 102 includes only the top side intermediate layer 706 and the base layer 702 (which includes the top side capacitive sensor array 716). In this embodiment, though, the upper tooth 726 includes a structural feature 728 that is made of a capacitive material. The structural feature 728 may be a prosthetic, such as a crown, a bridge, a metallic filling, or any other dental prosthetic that is made of a capacitive material. The structural feature 728 provides enough capacitance to trigger the top side capacitive sensor array 716 when the user bites down on the top side 102. In some embodiments, if several of the user's teeth have structural features (e.g., structural features similar to the structural feature 728), then a capacitive map that is sufficient to identify the user may be detected by the top side capacitive sensor array 716. If the capacitive map detected from the structural features of the user's teeth is sufficient to identify the user, then the top side outer layer 712 may be removed from the top side 102 (as shown in FIG. 25B). The processor 310 may determine whether the capacitive map detected from structural features of the user's teeth is sufficient to identify the user. For example, if the processor does not receive an input from the top side capacitive sensor array 716, then the processor may determine that the capacitive map, if any, detected by the top side capacitive sensor array 716 is insufficient to identify the user.

In operation, a user may place the user's finger on the biometric sensor 550 on the housing 500. The biometric sensor 550 may detect a fingerprint model, and the processor 310 may record and store the fingerprint model in the memory 370 in the COPA device 100. The processor 310 may determine whether the scanned fingerprint model of the current user matches the stored fingerprint model of the intended user. Then, the COPA device 100 may be inserted into the mouth of the user while the user is holding the housing 500. The environmental sensor may detect a difference between the environmental attributes inside the user's mouth and the environmental attributes outside the user's mouth. For example, the environmental sensor 560 may detect a higher temperature within the user's mouth than outside of the user's mouth. The processor 310 may determine whether the COPA device 100 is positioned inside the user's mouth based on the detected environmental attributes inside the user's mouth. The user may then close the user's mouth around the COPA device 100 and bite into the COPA device 100, which may trigger the top side capacitive sensor array 716 and/or the bottom side capacitive sensor array 718 to perform capacitance measurements. The processor 310 may determine whether the COPA device 100 is correctly positioned within the user's mouth based on the capacitive map detected by the top side capacitive sensor array 716 and/or the bottom side capacitive sensor array 718. In some embodiments, a capacitive map of the user's mouth may be recorded and stored in the memory 370 when the COPA device 100 is created. The processor 310 may compare the current capacitive map to the original capacitive map to determine whether there is a match between the current user of the COPA device 100 and the intended user of the COPA device 100. The processor 310 may also compare the current capacitive map to the original capacitive map to determine whether the COPA device 100 is correctly positioned within the intended user's mouth. The processor 310 may verify the intended user by either of, or both of, the COPA device 100 (specifically, the top side and/or bottom side capacitive sensor arrays 716, 718) and the housing 500 (specifically, the biometric sensor 550). Additionally, the prescribed substance 720 may be dispensed to the intended user after verification of any one, two, or three of: (1) the scanned fingerprint model of the current user matches the stored fingerprint model of the intended user; (2) the COPA device 100 is positioned inside the user's mouth; and/or (3) the detected capacitive map of the current user matches the stored capacitive map of the intended user.

When the user is verified as the intended user and the COPA device 100 is correctly positioned within the intended user's mouth, the processor 310 may send an activation instruction to the actuator 330 and open the exit valves 340 to administer one or more of the prescribed substances 720 stored in the micro-pump unit 300 in accordance with dosage instructions for the intended user. The activation of the actuator 330 and the opening of the exit valves 340 may be based on dosage instructions or prescriptions stored in the memory 370 when the prescribed substance 720 is filled.

In some embodiments, the COPA device 100 may include one or more indicators that can provide feedback and/or alerts to the user when the COPA device 100 is in use. The indicator(s) may include a vibrating component, a sound generation component (e.g., a speaker), and/or a visual indicator component. For example, the vibrating component can cause the COPA device 100 to vibrate with different pulsing patterns to indicate the different statuses of the COPA device (e.g., one vibration to indicate proper user authentication and initiation of dispensing, two vibrations to indicate completion of dispensing, patterned or repeated vibrations to indicate an error with the COPA device, etc.). Similarly, the sound generation component can generate various tones and/or patterns to indicate the different statuses of the COPA device. Likewise, the visual indicator component can include one or more LEDs that display different colors and/or patterns to indicate the different statuses of the COPA device. The current status of the COPA device 100 may be determined based on feedback from the processor 310, the biometric sensor 550, the environmental sensor 560, the top side capacitive sensor array 716, and/or the bottom side capacitive sensor array 718 (e.g., correct or incorrect positioning of the COPA device 100), sensors for monitoring the dispensing of the substance (e.g., volume and/or flow sensors), the docking station 400, and/or other sensors or monitoring devices associated with the COPA device 100 and/or the docking station 400 for determining the status of the COPA device 100.

FIG. 26 is a schematic diagram of a system 900 according to embodiments of the present disclosure. The system 900 includes the COPA device 100, the docking station 400, a doctor 910, a pharmacy 920, a patient/authorized caregiver portal 930, and a central management system 950 in communication with each other via a network 940. In some embodiments, the system 900 may also include the housing 500 in lieu of or in addition to the docking station 400. The housing 500, the doctor 910, the pharmacy 920, the patient/authorized caregiver portal 930, and the central management system 950 may be in communication with each other via the network 940. In some embodiments, the housing 500 can include network communication components, such as a wireless transceiver, a network interface device, and/or any other suitable communication components. In other embodiments, the housing 500 need not include such network communication components. The network 940 may include one or more wireless access networks and/or one or more wireline networks that may connect to a backbone network or the Internet. The network 940 may include network encryption and security policies for protecting patients' privacy. The network 940 may include cloud storage for data storage and retrieval across the network 940 based on the encryption and security policies. The doctor 910 may be a registered doctor for the prescription management system. The pharmacy 920 may be an approved pharmacy and/or a COPA device (e.g., the mouthpiece) fabricator. A COPA fabricator may be individuals or organizations trained in procuring standardized dental impressions (e.g., the COPA device 100) that capture varying individual elements of the intended recipients' dentition. The system 900 may provide an identification system for tracking the path of prescription administration and management to prevent misuse and mismanagement.

At a high level, the doctor 910 may prescribe a medication to a patient and the pharmacy 920 may create the mouthpiece for the patient and fill the mouthpiece according to the prescription(s) provided by the doctor 910. The pharmacy 920 may program the micro-pump unit of the mouthpiece to deliver an exact dosage of the prescribed medication and/or a dosage intake time. In this regard, dosage instructions for the patient may be stored in memory of the micro-pump unit. The patient may insert the mouthpiece into the patient's mouth and the micro-pump unit will, upon verification that the user is the intended recipient, dispense the prescribed medication as programmed. The patient may dock the mouthpiece at the docking station when the mouthpiece is not in use. The docking station may charge the mouthpiece and/or communicate with the doctor 910 and/or the pharmacy 920 via wireless and/or wired connections. The doctor 910 and/or the pharmacy 920 may monitor and retrieve information associated with the dispensing of the prescribed medication from the docking station 400. The doctor 910 may provide instructions to adjust the dosage instructions based on the monitoring and/or the retrieval information, and/or based on evaluations of the patient's progress. The pharmacy 920 may send instructions to the docking station 400 to adjust the dosage instructions stored in the memory of the micro-pump unit based on the order from the doctor 910. For example, when the mouthpiece is docked at the docking station, the dosage instructions stored in the memory can be updated or re-programmed accordingly. Alternatively, the dosage instructions stored in the memory can be updated or re-programmed at the pharmacy 920. Similarly, the doctor 910 may prescribe new medication based on the monitoring and/or the retrieval information, and/or based on evaluations of the patient's progress. The pharmacy 920 may refill the micro-pump unit 300 accordingly. In some embodiments, the doctor 910 and/or the pharmacy 920 may monitor and retrieve information associated with the dispensing of the prescribed substance from the housing 500. The pharmacy 920 may refill the housing 500 with a medication bottle filled with a prescribed substance based on the monitoring and/or the retrieval information, and/or based on evaluations of the patient's progress.

The patient/authorized caregiver portal 930 may be stored on a computer server or in cloud storage on the network 940. The management system 950 may be hosted on the network 940. The management system 950 may include a master database that stores information associated with the patient and all COPA activities. For example, the management system 950 may allow doctors (e.g., the doctor 910), assembly or fulfillment technicians, pharmacists (e.g., the pharmacy 920), and any healthcare personnel that partake in the COPA process to access at least some portions of the master database, for example, based on logins. In an embodiment, different personnel may have different login profiles and the accesses to the master database may be based on login profiles. In some embodiments, the patient/authorized caregiver portal 930 may be hosted on the management system 950 and may have certain accesses to the master database. The patient information may include an identification of the patient, health history, prescription history, identification of the processor 310 within the COPA device 100, identification of the docking station 400 at which the COPA device 100 is charged, etc. The patient's identification may include a social security number (SSN) of the patient or other unique identifier. The prescription history may include identifications of doctors (e.g., the doctor 910) who prescribed medications to the patient, identifications of pharmacies (e.g., the pharmacy 920) at which the prescribed medications were filled or refilled, identifications of the prescribed medications, and an identification of the processor 310 within the micro-pump unit 300 where the medications were filled. The prescription history may also be stored and managed by the management system 950. The physicians' identifications may include national provider identifiers (NPIs) of the physicians. The NPIs are unique identification numbers for Health Insurance Portability and Accountability Act (HIPPA) covered physicians. The pharmacies' identifications may include an impression technician identifier (ID), an assembly technician ID, and a registered pharmacy ID. The impression technician ID identifies the technician who created the COPA device 100 for the patient. The assembly technician ID identifies the technician who assembled or filled the prescribed medication into the micro-pump unit 300 of the COPA device 100. The pharmacy ID identifies the pharmacy at which the prescribed medication was filled. The prescribed medications' identifications may include dosage IDs that identify each prescribed substance or formulation filled into the micro-pump unit 300 of the COPA device 100.

In an embodiment, the doctor 910 may examine a patient and determine whether alternative therapies may be helpful to the patient. When the doctor 910 determines that the patient is in need of a particular medication, for example, according to guidelines for drug formulations based on COPA dosing options, the doctor may order a prescription for the patient. The doctor 910 may electronically transmit the prescription to the pharmacy 920 via the network 940, for example, according to HIPPA standards of protection for data and electronic medical record (EMR) formats.

At a COPA fabricator, a technician may create a mold for the COPA device 100, for example, according to COPA guidelines and instructions. The mold may include a sealed sleeve similar to the sealed sleeve 124. For example, the technician may use a dental tray filled with bio friendly polymers to create the mold. COPA approved dentists, hygienists, and/or other trained professionals (e.g., a COPA device assembly technician) may complete the creation of the mold for the COPA device 100.

An assembly technician may prepare a pre-packaged micro-pump unit 300. Each micro-pump unit 300 may be identified based on an ID of the processor 310 embedded within the micro-pump unit 300. The assembly technician may record the ID of the micro-pump unit 300 in the management system 950. For example, the assembly technician may enter the ID into the management system 950, query a COPA device ID database of the management system 950 that stores and tracks IDs of COPA devices (e.g., the COPA device 100), and create a new record for the COPA device 100 created for the patient. The assembly technician may activate the processor 310 within the micro-pump unit 300, for example, wirelessly. The activation may include programming the processor 310 according to the order received from the doctor 910. The programming may include the dosage instructions for the patient (e.g., a dosage amount and the dosage timing for each prescribed medication). As described above, different chambers 322 may be filled with different formulations. Thus, the programming may include a release sequence, specific release times, and/or release durations for the different formulations, and/or intervals between releases. For example, some formulations may be programmed for instant release (IR) and some formulations may be programmed for extended release (ER).

After activating the micro-pump unit 300 or the processor 310, the assembly technician may place the activated micro-pump unit 300 into the top center of the mold where the sealed sleeve is positioned. The micro-pump unit 300 may be positioned such that the access cannulas 730 extend outside the sealed sleeve through the access ports 122 and the exit cannulas 740 extend through the base of the mold. The assembly technician may place a top side capacitive sensor array 716 into the base layer 702 of the COPA device 100. The assembly technician may also place an environmental sensor 560 onto the outer face 129 of the back wall portion 128 of the COPA device 100. The assembly technician may attach a hose from an air compressor to the access ports 122 on top of the mold such that pressurized air may be pumped through the access cannulas 730 into the micro-pump unit 300 to ensure that the flow channels 350 are not compressed during the filling of the mold. The assembly technician may pump a liquid polymer into the mold and allow the liquid polymer to set. After the liquid polymer is set, the COPA device 100 is complete.

Upon completion of the COPA device 100, the COPA device 100 can be transferred to the pharmacy 920. At the pharmacy 920, a pharmacy staff (e.g., a COPA fulfillment technician) may place the COPA device 100 on a pedestal or other structure configured to allow access to the micro-pump unit 300 for filling. The pedestal may be covered by a sterile sleeve each time prior to placing a COPA device on the pedestal. The pharmacy staff may retrieve a record of the COPA device 100 based on the ID of the processor 310 within the COPA device 100, for example, from the COPA management system 950 via the network 940. The pharmacy staff may procure the medications (e.g., vials, pouches, bottles, etc.) from a drug manufacturer based on the dosage specified in the order received from the doctor 910. The pharmacy staff may update the record for the COPA device 100. The pharmacy staff may activate or open control valves at the access ports 122 to inject or deposit the formulated prescription (e.g., the prescribed substance 720) into one or more chambers 322 of the reservoir 320 via the access ports 122. After completing the filling, the pharmacy staff may close the control valves. The pharmacy staff may repeat the same process for filling other chambers 322 in the reservoir 320. Subsequently, the releasing of the formulated prescription is based on matching of the intended recipient's teeth and the COPA device 100 as described above. It should be noted that in some embodiments, the pharmacy 920 and the COPA fabricator may be the same entity.

In other embodiments, at the pharmacy 920, a pharmacy staff (e.g., a COPA fulfillment technician) may place the COPA device 100 on the housing 500 to allow access to the medication bottle 590 for filling. The pharmacy staff may retrieve a record of the COPA device 100 based on the ID of the processor 310 within the COPA device 100, for example, from the COPA management system 950 via the network 940. The pharmacy staff may procure the medications (e.g., vials, pouches, bottles, etc.) from a drug manufacturer based on the dosage specified in the order received from the doctor 910. The pharmacy staff may update the record for the COPA device 100. The pharmacy staff may open one or more walls (e.g., the bottom wall 570) of the housing 500 to insert a medication bottle 590 containing the formulated prescription (e.g., the prescribed substance 720). After completing the insertion, the pharmacy staff may reattach the removed wall(s) of the housing. Subsequently, the releasing of the formulated prescription is based on any one, two, or three of matching of the intended recipient's fingerprint model with a currently detected fingerprint model, detection of environmental attributes within a pre-defined range, and/or matching of the intended recipient's capacitive map with a currently detected capacitive map as described above.

The initial ID (e.g., of the processor 310) created for the COPA device 100 can be a permanent ID for the COPA device 100. Information associated with the filled prescription may be associated with the ID of the COPA device 100 and recorded in the management system 950 and/or an internal tracking system of the pharmacy 920. Thus, the COPA device 100 is fully traceable through the creation and preparation path. In addition, the mold used to craft the COPA device 100 may be assigned with a mold ID and may be stored in the management system 950 in association with the ID of the processor 310. Protocols for the use of the stored molds may be documented and records of subsequent mouthpieces may be stored in association in the management system 950. As such, misuse or fraud may be traced via the management system 950.

The pharmacy staff may pair the COPA device 100 with the docking station 400. The pharmacy staff may record an ID of the docking station 400 in association with the COPA device 100 in the management system 950. The wireless transceiver 420 of the docking station 400 may be recorded and registered in the management system 950 for remote access to the processor 310 embedded in the COPA device 100. For example, a pharmacy staff may adjust the dosage of the filled prescribed medication based on the instructions or an order of the prescribing doctor 910 by accessing the processor 310 via the wireless transceiver 420 without the patient returning the mouthpiece to the pharmacy 920 prior to depletion of the active ingredient(s). The adjustment may allow for a limited number of revisions, for example, to the dosing amount per release, the timing of the release, and/or suspension of one or more of the chambers 322. While the embodiment in FIG. 26 illustrates the docking station 400 in association with the COPA device 100, in other embodiments, the housing 500 may be in association with the COPA device 100. For example, the pharmacy staff may pair the COPA device 100 with the housing 500, and the pharmacy staff may record an ID of the housing 500 in association with the COPA device 100 in the management system 950.

The patient may pick up the COPA device 100 and the docking station 400 from the pharmacy 920 and the pharmacy staff may provide instructions of usage to the patient. The patient may insert the COPA device 100 into the patient's mouth and close the mouth to bite on the COPA device 100 so that the prescription dispensing unit 120 or the micro-pump unit 300 may release the prescribed medication for ingestion. The patient may clean the COPA device 100 and dock the COPA device 100 at the docking station 400 after use.

The patient and/or the authorized care giver may have access to an online COPA account, for example, hosted on the management system 950 via the network 940. The wireless transceiver 420 may detect and transmit data such as activities recorded by the mouthpiece (e.g., dispensing dosages and timings for each medication) to the management system 950. The patient may view records of medications loaded into each chamber 322 of the COPA device 100. The patient may view records of the administration path of medications filled in the COPA device 100 including the initial prescription and any subsequent revisions. The patient may view records of an anticipated depletion timeline for the patient to pick up a second pre-filled COPA device (e.g., the COPA device 100) and drop off the depleted COPA device if the treatment is a recurring treatment.

In an embodiment, the refill process for the COPA device 100 may use similar policies as today's drug refill policies. The COPA device 100 may be used in prolonged treatment plans. A prescribing doctor 910 may adjust and revise the prescription based on the treatment results observed from the patient. The doctor 910 may electronically transfer the revised prescription to the pharmacy 920. The pharmacy staff or the fulfillment technician may send revised instructions to the processor 310 wirelessly through the wireless transceiver 420 of the docking station 400. The management system 950 may house a full record of all revisions. When the intended recipient has depleted the COPA as planned, or as revised, the COPA device 100 may be returned to the pharmacy 920 for refills, for example, as directed by the prescribing doctor 910. The pharmacy staff may flush saline solution into the COPA device 100 through the access ports 122 into the sealed prescription dispensing unit 120 and out the exit valves 222. After flushing the COPA device 100, the pharmacy staff may refill the COPA device 100 based on the order received from the doctor 910 and may update the record in the management system 950. For example, if a prescription is written for three refills, the record would indicate three dosage IDs in association with the ID of the processor 310 of the COPA device 100 and previous dosage IDs. By recording all information associated with the COPA device 100, the patient and the dosage information in the management system 950 may be retrieved at any time, including when the patient changes providers or pharmacies during a treatment plan.

In an embodiment, when the COPA device 100 is no longer needed, for example, at the end of a treatment plan or change of treatment plan, the COPA device 100 may be deactivated and the management system 950 may be updated to indicate the deactivation of the COPA device 100. In some embodiments, when deactivation time of the COPA device 100 is within a certain time limit, for example, X number of months, an assembly technician may reuse the original impression to build a new COPA device 100. The ID of the processor 310 within the new COPA device 100 may be stored in the management system 950 in association with the old ID of the old COPA device 100. In an embodiment, when a COPA device 100 needs to be recast due to actual change in the dentition of a recipient, the creation and preparation processes described above may be repeated. Information associated with the new mold may be stored on the management system 950 in association with the patient and the prescribed medications. By tracking all COPA devices 100 associated with a particular patient or a particular prescription, it may be less likely for an unintended user to gain access to the prescribed medications or for an intended user to provide false information for misuse of prescribed substances.

Figure 27:
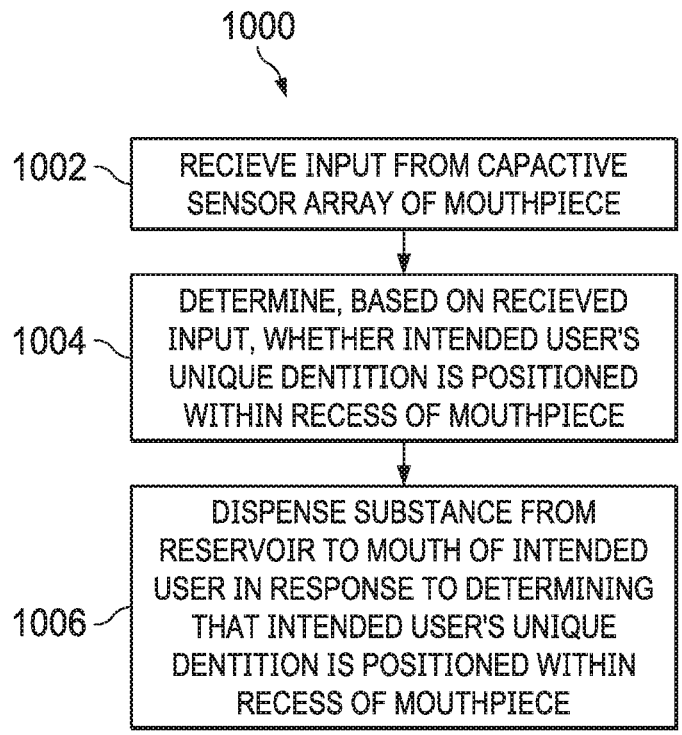
FIG. 27 is a flow diagram of a method of dispensing a substance to an intended user according to embodiments of the present disclosure.

FIG. 27 is a flow diagram of a method 1000 of dispensing a substance to an intended user according to embodiments of the present disclosure. The method 1000 can be better understood with reference to FIGS. 23 and 24. As illustrated, the method 1000 includes a number of enumerated steps, but embodiments of the method 1000 may include additional steps before, after, and in between the enumerated steps. In some embodiments, one or more of the enumerated steps may be omitted or performed in a different order.

At step 1002, the method 1000 includes receiving an input from a capacitive sensor array of a mouthpiece. The capacitive sensor array may be the top side capacitive sensor array 716 and/or the bottom side capacitive sensor array 718. The mouthpiece may be the COPA device 100. In some embodiments, the input may be generated by the top side capacitive sensor array 716 and/or the bottom side capacitive sensor array 718, and then the input may be received by the processor 310.

At step 1004, the method 1000 includes determining, based on the received input, whether an intended user's unique dentition is positioned within a recess of the mouthpiece. In some embodiments, the processor 310 may determine whether an intended user's unique dentition is positioned within a recess (e.g., the recess 110) of the mouthpiece (e.g., the COPA device 100). For example, the processor 310 may compare a capacitive map associated with the input to a predetermined capacitive map associated with the intended user's unique dentition to determine whether there is a match between the current user of the COPA device 100 and the intended user of the COPA device 100.

At step 1006, the method 1000 includes dispensing a substance from a reservoir to a mouth of the intended user in response to determining that the intended user's unique dentition is positioned within the recess of the mouthpiece. In some embodiments, the reservoir (e.g., the reservoir 320) may be positioned outside the mouth. Therefore, the substance may be dispensed from outside the mouth. In other embodiments, the reservoir (e.g., the reservoir 320) may be positioned within the mouth. Therefore, the substance may be dispensed from inside the mouth.

Figure 28:
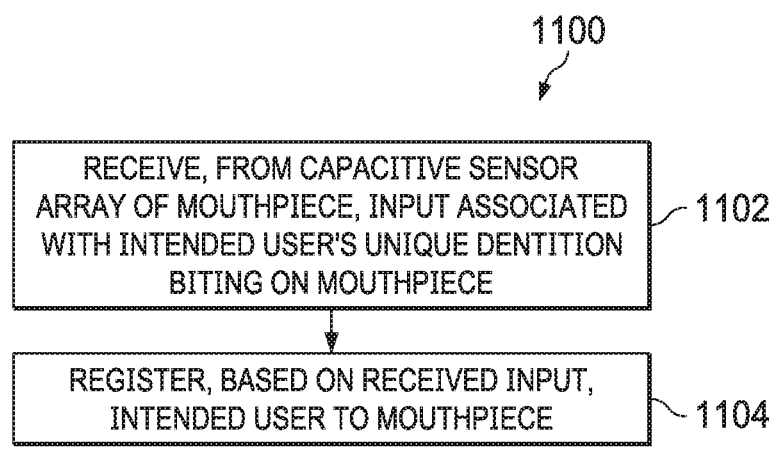
FIG. 28 is a flow diagram of a method of registering a substance dispensing apparatus to an intended user according to embodiments of the present disclosure.

FIG. 28 is a flow diagram of a method 1100 of registering a substance dispensing apparatus to an intended user. The method 1100 can be better understood with reference to FIGS. 3, 23, and 24. As illustrated, the method 1100 includes a number of enumerated steps, but embodiments of the method 1100 may include additional steps before, after, and in between the enumerated steps. In some embodiments, one or more of the enumerated steps may be omitted or performed in a different order.

At step 1102, the method 1100 includes receiving, from a capacitive sensor array of a mouthpiece, an input associated with an intended user's unique dentition biting on the mouthpiece. The capacitive sensor array may be the top side capacitive sensor array 716 and/or the bottom side capacitive sensor array 718. The mouthpiece may be the COPA device 100. In some embodiments, the received input is representative of a capacitive map of the intended user's unique dentition. Therefore, in an exemplary embodiment, the method 1100 may comprise receiving, from a capacitive sensor array of the mouthpiece, a capacitive map of the intended user's unique dentition, wherein the capacitive map may be generated based on the intended user's unique dentition biting on the mouthpiece. Additionally, in some embodiments, multiple inputs may be received to define a range of acceptable matches associated with the intended user's unique dentition.

In some embodiments, the method 1100 may further include a step of storing the received input in memory integrated in the substance dispensing apparatus. The memory may be memory 370 (which is discussed in greater detail above with respect to FIG. 7).

At step 1104, the method 1100 includes registering, based on the received input, the intended user to the mouthpiece. In some embodiments, the processor 310 may register the intended user to the mouthpiece (e.g., the COPA device 100). In some embodiments, the step of registering the intended user to the mouthpiece may be the first action taken after the mouthpiece is manufactured. In other embodiments, the intended user may be the first person to wear the mouthpiece after the mouthpiece is manufactured.

Figure 29:
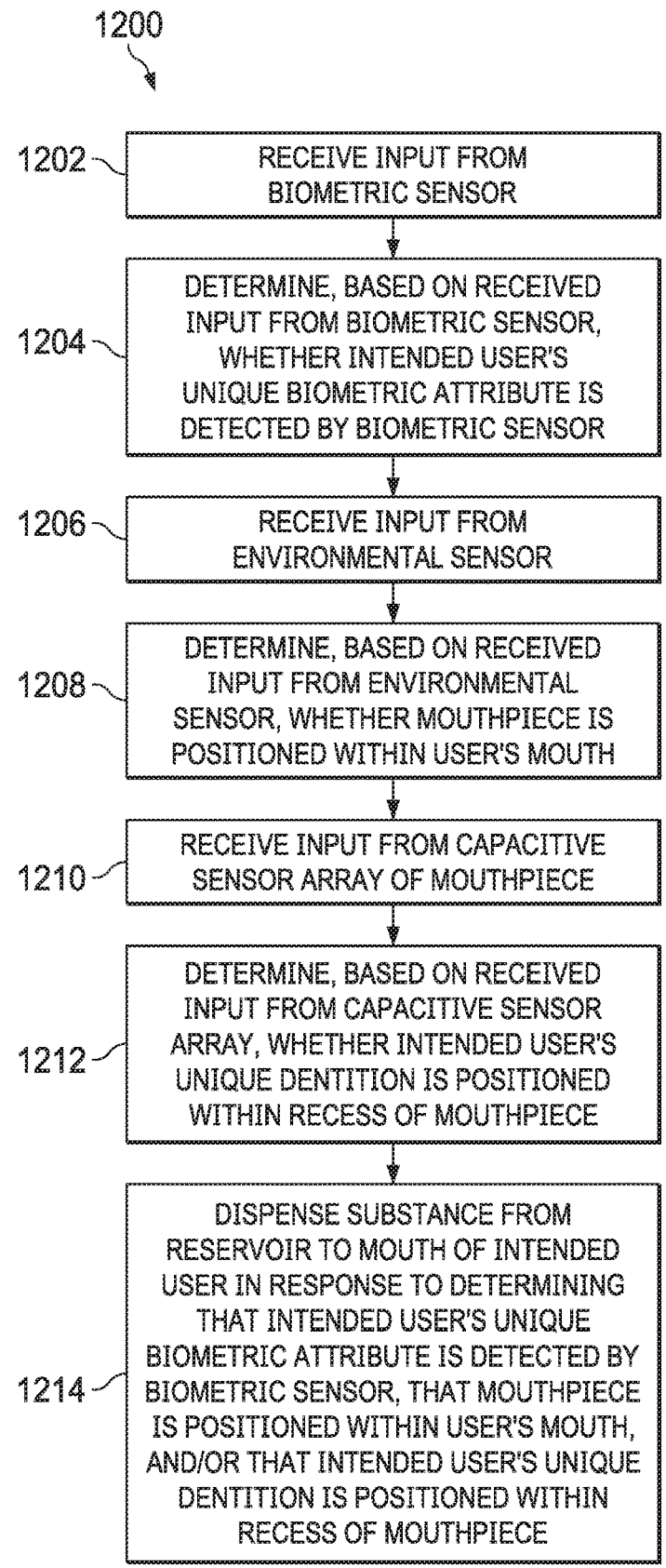
FIG. 29 is a flow diagram of a method of dispensing a substance to an intended user according to embodiments of the present disclosure.

FIG. 29 is a flow diagram of a method 1200 of dispensing a substance to an intended user according to embodiments of the present disclosure. The method 1200 can be better understood with reference to FIGS. 9, 12, 23, and 24. As illustrated, the method 1200 includes a number of enumerated steps, but embodiments of the method 1200 may include additional steps before, after, and in between the enumerated steps. In some embodiments, one or more of the enumerated steps may be omitted or performed in a different order.

At step 1202, the method 1200 includes receiving an input from a biometric sensor. The biometric sensor may be the biometric sensor 550. In some embodiments, the input may be generated by the biometric sensor 550, and then the input may be received by the processor 310. In some instances, the input may be received when the intended user places at least one of the intended user's fingers on the biometric sensor 550.

At step 1204, the method 1200 includes determining, based on the received input from the biometric sensor, whether the intended user's unique biometric attribute is detected by the biometric sensor. In some embodiments, the processor 310 may determine whether an intended user's unique fingerprint model is positioned on a biometric sensor (e.g., the biometric sensor 550) of the housing 500. For example, the processor 310 may compare a fingerprint model associated with the input to a predetermined fingerprint model associated with the intended user to determine whether there is a match between the current user of the housing 500 and the intended user of the housing 500. In some instances, the user's unique biometric attribute is detected by the biometric sensor 550 when the user's unique biometric attribute is positioned on the biometric sensor 550. In other examples, the user's unique biometric attribute is detected by the biometric sensor 550 when the user's unique biometric attribute is spaced from the biometric sensor 550.

At step 1206, the method 1200 includes receiving an input from an environmental sensor. The environmental sensor may be the environmental sensor 560. In some embodiments, the input may be generated by the environmental sensor 560, and then the input may be received by the processor 310.

At step 1208, the method 1200 includes determining, based on the received input from the environmental sensor, whether the mouthpiece is positioned within the user's mouth. In some embodiments, the processor 310 may determine whether the mouthpiece (e.g., the COPA device 100), is positioned within the user's mouth. For example, the processor 310 may compare an environmental attribute associated with the input to a pre-defined range of environmental attributes to determine whether the current environmental attribute is within the pre-defined range of environmental attributes. In some embodiments, when the current environmental attribute is within the pre-defined range of environmental attributes, the processor 310 may determine that the mouthpiece (e.g., the COPA device 100) is positioned within the user's mouth.

At step 1210, the method 1200 includes receiving an input from a capacitive sensor array of a mouthpiece. The capacitive sensor array may be the top side capacitive sensor array 716 and/or the bottom side capacitive sensor array 718. The mouthpiece may be the COPA device 100. In some embodiments, the input may be generated by the top side capacitive sensor array 716 and/or the bottom side capacitive sensor array 718, and then the input may be received by the processor 310.

At step 1212, the method 1200 includes determining, based on the received input from the capacitive sensor array, whether the intended user's unique dentition is positioned within a recess of the mouthpiece. In some embodiments, the processor 310 may determine whether the intended user's unique dentition is positioned within a recess (e.g., the recess 110) of the mouthpiece (e.g., the COPA device 100). For example, the processor 310 may compare a capacitive map associated with the input to a predetermined capacitive map associated with the intended user's unique dentition to determine whether there is a match between the current user of the COPA device 100 and the intended user of the COPA device 100.

At step 1214, the method 1200 includes dispensing a substance from a reservoir to a mouth of the intended user in response to determining that the intended user's unique biometric attribute is detected by the biometric sensor, that the mouthpiece is positioned within the user's mouth, and/or that the intended user's unique dentition is positioned within the recess of the mouthpiece. In some embodiments, the method 1200 can include any one, two, and/or three of the steps described above. Thus, step 1214 may be performed by any combination of steps 1202/1204, steps 1206/1208, and/or steps 1210/1212. In some embodiments, the reservoir (e.g., the reservoir 320) may be positioned outside the mouth. Therefore, the substance may be dispensed from outside the mouth. In other embodiments, the reservoir (e.g., the reservoir 320) may be positioned within the mouth. Therefore, the substance may be dispensed from inside the mouth.

Figure 30:
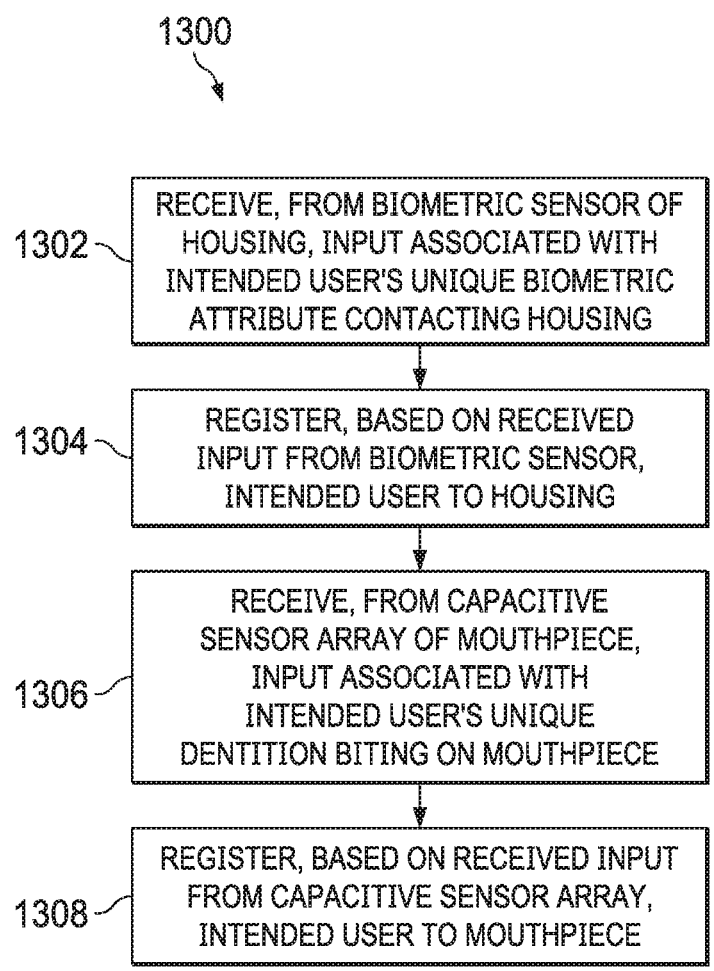
FIG. 30 is a flow diagram of a method of registering a substance dispensing apparatus and/or registering a housing to an intended user according to embodiments of the present disclosure.

FIG. 30 is a flow diagram of a method 1300 of registering a substance dispensing apparatus and/or a housing to an intended user. The method 1300 can be better understood with reference to FIGS. 3, 9, 23, and 24. As illustrated, the method 1300 includes a number of enumerated steps, but embodiments of the method 1300 may include additional steps before, after, and in between the enumerated steps. In some embodiments, one or more of the enumerated steps may be omitted or performed in a different order.

At step 1302, the method 1300 includes receiving, from a biometric sensor of a housing, an input associated with an intended user's unique biometric attribute contacting the housing. The biometric sensor may be the biometric sensor 550, and the housing may be the housing 500. In some embodiments, the received input is representative of the intended user's unique fingerprint model. Therefore, in an exemplary embodiment, the method 1300 may comprise receiving, from a biometric sensor of the housing, the intended user's fingerprint model, wherein the intended user's fingerprint model may be generated based on the intended user's fingerprint contacting the biometric sensor. Additionally, in some embodiments, multiple inputs from the biometric sensor may be received to define a range of acceptable matches associated with the intended user's unique fingerprint model. In some embodiments, the method 1300 may further include a step of storing the received input from the biometric sensor in memory integrated in the housing. In some embodiments, the biometric attribute may not contact the housing 500.

At step 1304, the method 1300 includes registering, based on the received input from the biometric sensor, the intended user to the housing. In some embodiments, the processor 310 may register the intended user to the housing (e.g., the housing 500). In some embodiments, the step of registering the intended user to the housing may be the first action taken after the housing is manufactured. In other embodiments, the intended user may be the first person to touch the biometric sensor after the housing is manufactured.

At step 1306, the method 1300 includes receiving, from a capacitive sensor array of a mouthpiece, an input associated with an intended user's unique dentition biting on the mouthpiece. The capacitive sensor array may be the top side capacitive sensor array 716 and/or the bottom side capacitive sensor array 718. The mouthpiece may be the COPA device 100. In some embodiments, the received input is representative of a capacitive map of the intended user's unique dentition. Therefore, in an exemplary embodiment, the method 1300 may comprise receiving, from a capacitive sensor array of the mouthpiece, a capacitive map of the intended user's unique dentition, wherein the capacitive map may be generated based on the intended user's unique dentition biting on the mouthpiece. Additionally, in some embodiments, multiple inputs may be received to define a range of acceptable matches associated with the intended user's unique dentition. In some embodiments, the received input from the capacitive sensor array of the mouthpiece is associated with an intended user's unique dentition being within the mouthpiece.

In some embodiments, the method 1300 may further include a step of storing the received input in memory integrated in the substance dispensing apparatus. The memory may be memory 370 (which is discussed in greater detail above with respect to FIG. 7).

At step 1308, the method 1300 includes registering, based on the received input from the capacitive sensor array, the intended user to the mouthpiece. In some embodiments, the processor 310 may register the intended user to the mouthpiece (e.g., the COPA device 100). In some embodiments, the step of registering the intended user to the mouthpiece may be the first action taken after the mouthpiece is manufactured. In other embodiments, the intended user may be the first person to wear the mouthpiece after the mouthpiece is manufactured. In still other instances, the step of registering the intended user to the mouthpiece may occur simultaneously with the step of registering the intended user to the housing. In various other examples, the step of registering the intended user to the mouthpiece may occur separately from the step of registering the intended user to the housing. For example, the method 1300 may include performing steps 1302/1304 and then later performing steps 1306/1308. In other examples, the method 1300 may include performing steps 1306/1308 and then later performing steps 1302/1304. In some embodiments, the step of registering the intended user to the mouthpiece and the step of registering the intended user to the housing may occur as part of the process of a patient being prescribed medication, which is discussed above with respect to FIG. 29.

The following table lists reference numerals and corresponding reference names:

TABLE 1

Reference Numerals and Corresponding Reference Names.

| Reference Numerals | Reference Names |
| --- | --- |
| 100 | COPA device |
| 102 | top side |
| 104 | bottom side |
| 110 | recess |
| 114 | compartment |
| 120 | prescription dispensing unit |
| 122 | access ports |
| 124 | sleeve |
| 126 | front wall portion |
| 127 | outer face of front wall |
| 128 | back wall portion |
| 129 | outer face of back wall |
| 130 | cutout portion |
| 134 | access opening |
| 210 | recess |
| 222 | exit valves |
| 300 | micro-pump unit |
| 310 | processor |
| 320 | reservoir |
| 322 | chambers |
| 330 | actuator |
| 340 | exit valves |
| 350 | flow channels |
| 360 | component |
| 370 | memory |
| 380 | wireless transceiver |
| 400 | docking station |
| 410 | docking compartment |
| 420 | wireless transceiver |
| 430 | component |
| 440 | indicators |
| 450 | COPA device sensing component |
| 500 | housing |
| 510 | upper portion |
| 520 | lower portion |
| 522 | front face |
| 524 | front wall |
| 530 | docking port |
| 532 | exit port |
| 540 | tubular member |
| 550 | biometric sensor |
| 560 | environmental sensor |
| 570 | bottom wall |
| 580 | tubular connector |
| 590 | medication bottle |
| 591 | base of medication bottle |
| 592 | cap |
| 594 | dip tube |
| 596 | valve |
| 598 | pump |
| 600 | distal end of dip tube |
| 602 | proximal end of dip tube |
| 604 | distal end of valve |
| 606 | proximal end of valve |
| 608 | distal end of tubular connector |
| 610 | proximal end of tubular connector |

TABLE 1-continued

Reference Numerals and Corresponding Reference Names.

| Reference Numerals | Reference Names |
| --- | --- |
| 612 | distal end of pump |
| 614 | proximal end of pump |
| 616 | distal end of tubular member |
| 618 | proximal end of tubular member |
| 702 | base layer |
| 706 | top side intermediate layer |
| 708 | bottom side intermediate layer |
| 710 | wire |
| 712 | top side outer layer |
| 714 | bottom side outer layer |
| 716 | top side capacitive sensor array |
| 718 | bottom side capacitive sensor array |
| 720 | prescribed substance |
| 722 | upper teeth |
| 724 | lower teeth |
| 726 | upper tooth |
| 728 | structural feature |
| 730 | access cannulas |
| 740 | exit cannulas |
| 900 | system |
| 910 | doctor |
| 920 | pharmacy |
| 930 | patient/authorized caregiver portal |
| 940 | network |
| 950 | COPA management system |

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of dispensing a substance to an intended user, the method comprising:
receiving an input from a biometric sensor;
determining, based on the received input from the biometric sensor, whether an intended user's unique biometric attribute is detected by the biometric sensor;
receiving an input from an environmental sensor;
determining, based on the received input from the environmental sensor, whether a mouthpiece is positioned within a user's mouth;
receiving an input from a capacitive sensor array of the mouthpiece;
determining, based on the received input from the capacitive sensor array, whether an intended user's unique dentition is positioned within a recess of the mouthpiece; and
dispensing a substance from a reservoir to a mouth of the intended user in response to determining that the intended user's unique biometric attribute is detected by the biometric sensor.

2. The method of claim 1, wherein the received input from the biometric sensor is representative of a fingerprint model of the intended user.

3. The method of claim 2, wherein the determining whether the intended user's unique biometric attribute is detected by the biometric sensor includes comparing a fingerprint model associated with the input received from the biometric sensor to a predetermined fingerprint model associated with the intended user's unique biometric attribute.

4. The method of claim 1, wherein the dispensing a substance further comprises dispensing the substance from the reservoir to the mouth of the intended user in response to determining that the mouthpiece is positioned within the user's mouth.

5. The method of claim 4, wherein the dispensing a substance further comprises dispensing the substance from the reservoir to the mouth of the intended user in response to determining that the intended user's unique dentition is positioned within the recess of the mouthpiece.

6. The method of claim 1, further comprising registering, based on the received input from the biometric sensor, the intended user to a housing coupled to the biometric sensor.

7. The method of claim 6, further comprising storing the received input from the biometric sensor in memory coupled to the housing.

8. The method of claim 6, wherein the receiving an input from the biometric sensor includes receiving a plurality of inputs to define a range of acceptable matches associated with the intended user's unique biometric attribute contacting the housing.

9. The method of claim 1, further comprising registering, based on the received input from the capacitive sensor array, the intended user to the mouthpiece.

10. The method of claim 9, wherein the receiving an input from the capacitive sensor array includes receiving a plurality of inputs to define a range of acceptable matches associated with the intended user's unique dentition being positioned within the recess of the mouthpiece.

11. The method of claim 1, wherein the dispensing the substance from the reservoir to the mouth of the intended user includes dispensing the substance from the reservoir to the mouth of the intended user automatically in response to determining that the intended user's unique biometric attribute is detected by the biometric sensor.

12. The method of claim 1, wherein the dispensing the substance from the reservoir to the mouth of the intended user is further based on determining that the intended user's unique dentition is positioned within the recess of the mouthpiece.

13. The method of claim 1, wherein the dispensing the substance from the reservoir to the mouth of the intended user is further based on:
determining that the mouthpiece is positioned within the user's mouth; and
determining that the intended user's unique dentition is positioned within the recess of the mouthpiece.

14. A method of dispensing a substance to an intended user, the method comprising:
receiving an input from a biometric sensor coupled to at least one wall of a housing defining a cavity sized and shaped to receive at least a portion of a reservoir, the housing sized and shaped for handheld use;
determining, based on the received input from the biometric sensor, whether an intended user's unique biometric attribute is detected by the biometric sensor;
receiving an input from a dentition sensing element of a mouthpiece, the mouthpiece coupled to the housing;
determining, based on the received input from the dentition sensing element, whether an intended user's unique dentition is positioned within a recess of the mouthpiece; and
dispensing, by a pump coupled to the mouthpiece, a substance from the reservoir to a mouth of the intended user in response to determining that the intended user's unique biometric attribute is detected by the biometric sensor.

15. The method of claim 14, further comprising:
receiving an input from an environmental sensor; and
determining, based on the received input from the environmental sensor, whether the mouthpiece is positioned within a user's mouth.

16. The method of claim 15, wherein the dispensing a substance further comprises dispensing the substance from the reservoir to the mouth of the intended user in response to determining that the mouthpiece is positioned within the user's mouth.

17. The method of claim 16, wherein the dispensing a substance further comprises dispensing the substance from the reservoir to the mouth of the intended user in response to determining that the intended user's unique dentition is positioned within the recess of the mouthpiece.

18. The method of claim 14, further comprising:
registering, based on the received input from the biometric sensor, the intended user to the housing; and
storing the received input from the biometric sensor in memory coupled to the housing.

19. The method of claim 14, wherein the dispensing a substance further comprises dispensing the substance from the reservoir, through a cap positioned within the cavity of the housing, and to the mouth of the intended user.

20. The method of claim 14, further comprising registering, based on the received input from the dentition sensing element, the intended user to the mouthpiece.

21. The method of claim 14, wherein the dentition sensing element comprises a capacitive sensor array.

22. The method of claim 21, further comprising registering, based on the received input from the capacitive sensor array, the intended user to the mouthpiece.

23. The method of claim 14, wherein the dispensing the substance from the reservoir to the mouth of the intended user includes dispensing the substance from the reservoir to the mouth of the intended user automatically in response to determining that the intended user's unique biometric attribute is detected by the biometric sensor.

24. The method of claim 14, wherein the dispensing the substance from the reservoir to the mouth of the intended user is further based on determining that the intended user's unique dentition is positioned within the recess of the mouthpiece.

25. The method of claim 14, wherein the dispensing the substance from the reservoir to the mouth of the intended user is further based on:
determining that the mouthpiece is positioned within a user's mouth; and
determining that the intended user's unique dentition is positioned within the recess of the mouthpiece.

* * * * *